(12) United States Patent
Amit et al.

(10) Patent No.: US 12,391,918 B2
(45) Date of Patent: Aug. 19, 2025

(54) MEDIA FOR CULTURING STEM CELLS

(71) Applicant: Technion Research & Development Foundation Limited, Haifa (IL)

(72) Inventors: Michal Amit, Yuvalim (IL); Joseph Itskovitz-Eldor, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 372 days.

(21) Appl. No.: 17/971,677

(22) Filed: Oct. 24, 2022

(65) Prior Publication Data

US 2023/0060616 A1 Mar. 2, 2023

Related U.S. Application Data

(60) Division of application No. 16/454,168, filed on Jun. 27, 2019, now Pat. No. 11,512,283, which is a division of application No. 15/209,776, filed on Jul. 14, 2016, now Pat. No. 10,385,312, which is a continuation of application No. 13/909,128, filed on Jun. 4, 2013, now Pat. No. 9,404,079, which is a division of application No. 11/991,077, filed as application No. PCT/IL2006/000998 on Aug. 29, 2006, now Pat. No. 8,476,070.

(60) Provisional application No. 60/834,795, filed on Aug. 2, 2006, provisional application No. 60/711,668, filed on Aug. 29, 2005.

(51) Int. Cl.
| | |
|---|---|
| C12N 5/074 | (2010.01) |
| C12N 5/00 | (2006.01) |
| C12N 5/071 | (2010.01) |
| C12N 5/073 | (2010.01) |
| C12N 5/0735 | (2010.01) |

(52) U.S. Cl.
CPC ......... *C12N 5/0606* (2013.01); *C12N 5/0018* (2013.01); *C12N 5/0037* (2013.01); *C12N 5/0043* (2013.01); *C12N 5/0056* (2013.01); *C12N 5/0602* (2013.01); *C12N 5/0603* (2013.01); *C12N 2500/90* (2013.01); *C12N 2500/98* (2013.01); *C12N 2501/115* (2013.01); *C12N 2501/15* (2013.01); *C12N 2501/23* (2013.01); *C12N 2501/2306* (2013.01); *C12N 2506/02* (2013.01); *C12N 2533/52* (2013.01)

(58) Field of Classification Search
None
See application file for complete search history.

(56) References Cited

U.S. PATENT DOCUMENTS

| | | | |
|---|---|---|---|
| 5,418,159 A | 5/1995 | Gough et al. | |
| 6,107,543 A | 8/2000 | Sims et al. | |
| 6,245,566 B1 | 6/2001 | Gearhart et al. | |
| 6,576,464 B2 | 6/2003 | Gold et al. | |
| 7,250,294 B2 | 7/2007 | Carpenter et al. | |
| 7,413,902 B2 | 8/2008 | Bodnar et al. | |
| 7,413,904 B2 | 8/2008 | Gold et al. | |
| 7,432,104 B2 | 10/2008 | Mitalipova et al. | |
| 7,452,718 B2 | 11/2008 | Gold et al. | |
| 7,455,983 B2 | 11/2008 | Xu et al. | |
| 7,473,555 B2 | 1/2009 | Mandalam et al. | |
| 7,504,257 B2 | 3/2009 | Reubinoff et al. | |
| 7,560,281 B2 | 7/2009 | Carpenter et al. | |
| 7,638,328 B2 | 12/2009 | Eriksson et al. | |
| 7,641,897 B2 | 1/2010 | Weissman et al. | |
| 7,824,670 B2 | 11/2010 | Haggiag et al. | |
| 7,851,167 B2 | 12/2010 | Xu | |
| 7,892,835 B2 | 2/2011 | Akaike et al. | |
| 7,897,389 B2 | 3/2011 | Gold et al. | |
| 7,951,591 B2 | 5/2011 | Robl et al. | |
| 8,067,233 B2 | 11/2011 | Totey et al. | |
| 8,252,585 B2 | 8/2012 | Carpenter | |
| 8,252,586 B2 | 8/2012 | Carpenter et al. | |
| 8,318,486 B2 | 11/2012 | Amit et al. | |
| 8,563,311 B2 | 10/2013 | Amit et al. | |
| 8,597,947 B2 | 12/2013 | Reubinoff | |
| 8,637,311 B2 | 1/2014 | Mandalam et al. | |
| 8,697,444 B2 | 4/2014 | Schoonjans | |
| 8,722,405 B2 | 5/2014 | Tryggvason et al. | |
| 9,040,297 B2 | 5/2015 | Amit et al. | |
| 9,404,079 B2 | 8/2016 | Amit et al. | |

(Continued)

FOREIGN PATENT DOCUMENTS

| | | |
|---|---|---|
| AU | 2000072431 | 5/2001 |
| AU | 2001011128 | 7/2001 |

(Continued)

OTHER PUBLICATIONS

Official Action Dated Nov. 16, 2023 from the US Patent and Trademark Office Re. U.S. Appl. No. 17/178,279. (82 pages).

(Continued)

*Primary Examiner* — Marcia S Noble

(57) ABSTRACT

Well-defined, xeno-free culture media which comprise a TGF-beta isoform or the chimera formed between IL6 and the soluble IL6 receptor (IL6RIL6), which are capable of maintaining stem cells, and particularly, human embryonic stem cells, in an undifferentiated state are provided. Also provided are cell cultures comprising the culture media and the stem cells and methods of expanding and deriving embryonic stem cells in such well-defined, xeno-free culture media. In addition, the present invention provides methods of differentiating ESCs or EBs formed therefrom for the generation of lineage specific cells.

17 Claims, 13 Drawing Sheets
(12 of 13 Drawing Sheet(s) Filed in Color)
Specification includes a Sequence Listing.

(56) References Cited

U.S. PATENT DOCUMENTS

| | | |
|---|---|---|
| 9,834,749 B2 | 12/2017 | Amit et al. |
| 10,385,312 B2 | 8/2019 | Amit et al. |
| 10,968,427 B2 | 4/2021 | Amit et al. |
| 2002/0127715 A1 | 9/2002 | Benvenisty et al. |
| 2002/0168763 A1 | 11/2002 | Yan et al. |
| 2003/0064503 A1 | 4/2003 | Abujadayel |
| 2003/0119107 A1 | 6/2003 | Dang et al. |
| 2003/0153082 A1 | 8/2003 | Bhatia |
| 2003/0166272 A1 | 9/2003 | Abujadayel |
| 2003/0211603 A1 | 11/2003 | Earp et al. |
| 2003/0224411 A1 | 12/2003 | Stanton et al. |
| 2004/0009593 A1 | 1/2004 | Keirstead et al. |
| 2004/0014211 A1 | 1/2004 | Ogle et al. |
| 2004/0077985 A1 | 4/2004 | Rudd |
| 2004/0110286 A1 | 6/2004 | Bhatia |
| 2004/0137612 A1 | 7/2004 | Baksh et al. |
| 2004/0180347 A1 | 9/2004 | Stanton et al. |
| 2004/0191901 A1 | 9/2004 | Assady et al. |
| 2004/0229350 A1 | 11/2004 | Strelchenko et al. |
| 2005/0032207 A1 | 2/2005 | Wobus et al. |
| 2005/0054093 A1 | 3/2005 | Haas |
| 2005/0095703 A1 | 5/2005 | Semb et al. |
| 2005/0095708 A1 | 5/2005 | Pera et al. |
| 2005/0101014 A1 | 5/2005 | Keirstead et al. |
| 2005/0118713 A1 | 6/2005 | Strelchenko et al. |
| 2005/0153444 A1 | 7/2005 | Mandalam et al. |
| 2005/0153445 A1 | 7/2005 | Mandalam et al. |
| 2005/0164383 A1 | 7/2005 | Reubinoff et al. |
| 2005/0210537 A1 | 9/2005 | Dominko et al. |
| 2005/0214938 A1 | 9/2005 | Gold et al. |
| 2005/0220761 A1 | 10/2005 | Haggiag et al. |
| 2005/0227352 A1 | 10/2005 | Xie |
| 2005/0227353 A1 | 10/2005 | Mummery |
| 2005/0260591 A1 | 11/2005 | Ward et al. |
| 2006/0030040 A1 | 2/2006 | Yang et al. |
| 2006/0057720 A1 | 3/2006 | Xu et al. |
| 2006/0063253 A1 | 3/2006 | Maciag et al. |
| 2006/0134636 A1 | 6/2006 | Stanton et al. |
| 2006/0182724 A1 | 8/2006 | Riordan |
| 2006/0223179 A1 | 10/2006 | Thomson et al. |
| 2006/0252150 A1 | 11/2006 | Cheng |
| 2006/0286544 A1 | 12/2006 | Mandal et al. |
| 2007/0053890 A1 | 3/2007 | Rosic-Kablar et al. |
| 2007/0111306 A1 | 5/2007 | Salli et al. |
| 2007/0231898 A1 | 10/2007 | Keirstead et al. |
| 2007/0248945 A1 | 10/2007 | McLaughlin et al. |
| 2007/0249044 A1 | 10/2007 | Desai et al. |
| 2007/0280989 A1 | 12/2007 | Shahar et al. |
| 2007/0298453 A1 | 12/2007 | Murdoch et al. |
| 2008/0070303 A1 | 3/2008 | West et al. |
| 2008/0076176 A1 | 3/2008 | Dominko et al. |
| 2008/0171385 A1 | 7/2008 | Bergendahl et al. |
| 2008/0182328 A1 | 7/2008 | Snyder et al. |
| 2008/0193421 A1 | 8/2008 | Kruse et al. |
| 2008/0241919 A1 | 10/2008 | Parsons et al. |
| 2008/0274125 A1 | 11/2008 | Guehenneux |
| 2008/0311607 A1 | 12/2008 | Geng et al. |
| 2009/0029461 A1 | 1/2009 | Choo et al. |
| 2009/0104695 A1 | 4/2009 | Shushan et al. |
| 2009/0136559 A1 | 5/2009 | Athanasiou et al. |
| 2009/0148876 A1 | 6/2009 | Dodge |
| 2009/0155218 A1 | 6/2009 | Hayek et al. |
| 2009/0291496 A1 | 11/2009 | Racey et al. |
| 2010/0047906 A1 | 2/2010 | Totey et al. |
| 2010/0068806 A1 | 3/2010 | Laine et al. |
| 2010/0069251 A1 | 3/2010 | Kim et al. |
| 2010/0093091 A1 | 4/2010 | Reubinoff et al. |
| 2010/0120145 A1 | 5/2010 | Brunner et al. |
| 2010/0221829 A1 | 9/2010 | Amit et al. |
| 2011/0039332 A1 | 2/2011 | Sakurada et al. |
| 2011/0300114 A1 | 12/2011 | Priller et al. |
| 2011/0311977 A1 | 12/2011 | Mandal et al. |
| 2012/0122209 A1 | 5/2012 | Reubinoff et al. |
| 2012/0148537 A1 | 6/2012 | Chan et al. |
| 2012/0282691 A1 | 11/2012 | Qian et al. |
| 2012/0322146 A1 | 12/2012 | Carpenter et al. |
| 2013/0084563 A1 | 4/2013 | Amit et al. |
| 2013/0102023 A1 | 4/2013 | Smith et al. |
| 2013/0130375 A1 | 5/2013 | Rudy-Reil |
| 2013/0252329 A1 | 9/2013 | Amit et al. |
| 2013/0316445 A1 | 11/2013 | Beardsley et al. |
| 2015/0252326 A1 | 9/2015 | Amit et al. |
| 2016/0319241 A1 | 11/2016 | Amit et al. |
| 2018/0066227 A1 | 3/2018 | Amit et al. |
| 2019/0316082 A1 | 10/2019 | Amit et al. |
| 2021/0189331 A1 | 6/2021 | Amit et al. |

FOREIGN PATENT DOCUMENTS

| | | | |
|---|---|---|---|
| AU | 2002237681 | 6/2002 | |
| AU | 2002313670 | 1/2003 | |
| AU | 2004294835 | 6/2005 | |
| AU | 2009213101 | 10/2009 | |
| AU | 2014201623 | 5/2014 | |
| CA | 2248555 | 9/1997 | |
| CA | 2409698 | 11/2001 | |
| CA | 2434760 | 5/2002 | |
| CA | 2447015 | 11/2002 | |
| CA | 2451486 | 1/2003 | |
| CA | 2453068 | 1/2003 | |
| CA | 2453438 | 1/2003 | |
| CA | 2468335 | 6/2003 | |
| CA | 2469483 | 6/2003 | |
| CA | 2470539 | 6/2003 | |
| CA | 2508880 | 7/2004 | |
| CA | 2524611 | 11/2004 | |
| CA | 2559854 | 9/2005 | |
| CA | 2573437 | 2/2006 | |
| CA | 2640644 | 11/2013 | |
| EP | 1809739 | 7/2007 | |
| EP | 2267116 | 12/2010 | |
| GB | 2379447 | 3/2003 | |
| GB | 2392674 | 3/2004 | |
| GB | 2393733 | 4/2004 | |
| GB | 2393734 | 4/2004 | |
| GB | 2394723 | 5/2004 | |
| GB | 2427873 | 1/2007 | |
| GB | 2431165 | 4/2007 | |
| HK | 1075673 | 2/2009 | |
| HK | 1103106 | 7/2009 | |
| HK | 1055765 | 9/2010 | |
| IL | 141742 | 3/2002 | |
| IL | 152741 | 6/2003 | |
| IL | 159324 | 6/2004 | |
| IL | 159578 | 6/2004 | |
| IL | 159580 | 6/2004 | |
| IL | 160403 | 7/2004 | |
| IL | 177324 | 12/2006 | |
| IL | 178006 | 12/2006 | |
| IL | 180447 | 6/2007 | |
| WO | WO 97/33995 | 9/1997 | |
| WO | WO 99/01763 | 1/1999 | |
| WO | WO 99/02552 | 1/1999 | |
| WO | WO 99/20740 | 4/1999 | |
| WO | WO 99/20741 | 4/1999 | |
| WO | WO 00/070021 | 11/2000 | |
| WO | WO 02/31123 | 4/2002 | |
| WO | WO 02/44343 | 6/2002 | |
| WO | WO 02/086104 | 10/2002 | |
| WO | WO 03/000868 | 1/2003 | |
| WO | WO 03/004605 | 1/2003 | |
| WO | WO 03/006950 | 1/2003 | |
| WO | WO 03/014359 | 2/2003 | |
| WO | WO 03/020920 | 3/2003 | |
| WO | WO 03/050249 | 6/2003 | |
| WO | WO 03/050250 | 6/2003 | |
| WO | WO 03/095628 | 11/2003 | |
| WO | WO 2004/031369 | 4/2004 | |
| WO | WO 2004/044158 | 5/2004 | |
| WO | WO 2004/050826 | 6/2004 | |
| WO | WO 2004/055155 | 7/2004 | |
| WO | WO-2004055155 A2 * | 7/2004 | ........... C12N 5/0606 |
| WO | WO 2004/111210 | 12/2004 | |
| WO | WO 2005/065354 | 7/2005 | |

(56) References Cited

FOREIGN PATENT DOCUMENTS

| WO | WO 2006/017370 | 2/2006 | | |
|---|---|---|---|---|
| WO | WO 2006/020889 | 2/2006 | | |
| WO | WO-2006029198 A2 * | 3/2006 | ............... | C12N 5/00 |
| WO | WO 2006/070370 | 7/2006 | | |
| WO | WO 2007/002086 | 1/2007 | | |
| WO | WO 2007/002210 | 1/2007 | | |
| WO | WO 2007/026353 | 3/2007 | | |
| WO | WO 2007/122233 | 11/2007 | | |
| WO | WO 2008/007082 | 1/2008 | | |
| WO | WO 2008/015682 | 2/2008 | | |
| WO | WO 2008/054819 | 5/2008 | | |
| WO | WO 2008/148105 | 12/2008 | | |

OTHER PUBLICATIONS

Kassem et al. "Mesenchymal Stem Cells: Cell Biology and Potential Use in Therapy", Basic & Clinical Pharmacology & Toxicology, 95(5): 209-214, 2004.
Pan et al. "Stem Cell Pluripotency and Trascription Factor Oct4", Cell Research, 12(5-6):321-329, 2002.
St. John et al. "Analysis and Isolation of Embryonic Mammalian Neurons by Fluorescence-Activated Cell Sorting", The Journal of Neuroscience, 6(5): 1492-1512, May 1986.
University of Michigan Medical School "Embryonic Period (Weeks 3-8)", Anatomy, University of Michigan Medical School, pp. 1-5, 1999.
Notice of Allowance Dated Apr. 8, 2024 from the US Patent and Trademark Office Re. U.S. Appl. No. 17/178,279. (8 pages).
Advisory Action Before the Filing of an Appeal Brief Dated Jul. 6, 2017 From the US Patent and Trademark Office Re. U.S. Appl. No. 14/720,853. (4 pages).
Advisory Action Before the Filing of an Appeal Brief Dated Jul. 9, 2012 From the US Patent and Trademark Office Re. U.S. Appl. No. 12/309,817.
Applicant-Initiated Interview Summary Dated Jan. 11, 2016 From the US Patent and Trademark Office Re. U.S. Appl. No. 13/909,128.
Communication of a Notice of Opposition Dated Dec. 11, 2018 From the European Patent Office Re. Application No. 13185969.6. (4 Pages).
Communication Pursuant to Article 101(1) and Rule 81(2) to (3) EPC Dated Dec. 5, 2019 From the European Patent Office Re. Application No. 13185969.6. (4 Pages).
Communication Pursuant to Article 94(3) Dated Jan. 15, 2020 From the European Patent Office Re. Application No. 18186556.9. (4 Pages).
Communication Pursuant to Article 94(3) EP Dated Feb. 21, 2022 From the European Patent Office Re. Application No. 17197313.4. (4 Pages).
Communication Pursuant to Article 94(3) EPC Dated Mar. 2, 2016 From the European Patent Office Re. Application No. 13185969.6.
Communication Pursuant to Article 94(3) EPC Dated Apr. 11, 2017 From the European Patent Office Re. Application No. 06766237.9. (5 Pages).
Communication Pursuant to Article 94(3) EPC Dated Jul. 23, 2013 From the European Patent Office Re. Application No. 07790025.6.
Communication Pursuant to Article 94(3) EPC Dated Sep. 25, 2015 From the European Patent Office Re. Application No. 07790025.6.
Communication Pursuant to Article 94(3) EPC Dated Mar. 27, 2017 From the European Patent Office Re. Application No. 13185969.6. (4 Pages).
Communication Pursuant to Article 94(3) EPC Dated Jul. 28, 2014 From the European Patent Office Re. Application No. 07790025.6.
Communication Pursuant to Article 94(3) EPC Dated Sep. 28, 2011 From the European Patent Office Re. Application No. 07790025.6.
Communication Pursuant to Rule 70(2) and 70a(2) EPC and Reference to Rule 39(1) EPC Dated Oct. 20, 2014 From the European Patent Office Re. Application No. 13185969.6.
Communication Pursuant to Rules 70(2) and 70a(2) EPC Dated Aug. 10, 2010 From the European Patent Office Re. Application No. 06766237.9.
Communication Pursuant to Rules 70(2) and 70a(2) EPC of May 25, 2011 From the European Patent Office Re. Application No. 06766237.9.
Communication Pursuant to Rules 70(2) and 70a(20 EPC and Reference to Rule 39(1) EPC Dated Aug. 6, 2018 From the European Patent Office Re. Application No. 17197313.4. (2 Pages).
Communication Relating to the Results of the Partial International Search Dated Jan. 9, 2008 From the International Searching Authority Re.: Application No. PCT/IL2007/000970.
Communication Under Rule 71(3) EPC Dated May 2, 2016 From the European Patent Office Re. Application No. 07790025.6.
Communication Under Rule 71(3) EPC Dated Apr. 12, 2018 From the European Patent Office Re. Application No. 13185969.6. (7 Pages).
European Search Report and the European Search Opinion Dated Sep. 12, 2014 From the European Patent Office Re. Application No. 13185969.6.
European Search Report and the European Search Opinion Dated Nov. 13, 2018 From the European Patent Office Re. Application No. 18186556.9. (10 Pages).
European Search Report and the European Search Opinion Dated Apr. 18, 2018 From the European Patent Office Re. Application No. 17197313.4. (7 Pages).
Examination Report Dated Mar. 27, 2012 From the Intellectual Property Office of Singapore Issued by the Austrian Patent Office, Service and Information Center (TRF) on Feb. 20, 2012 Re. Application No. 200801730-3.
Examination Report Dated Jan. 30, 2014 From the Intellectual Property Office of Singapore Issued by the Austrian Patent Office Re. Application No. 201200039-4.
Examiner's Report Dated Jan. 27, 2012 From the Australian Government IP Australia Re. Application No. 2006286149.
Examiner's Report Dated Aug. 29, 2011 From the Australian Government IP Australia Re. Application No. 2006286149.
Final Official Action Dated Aug. 20, 2020 from the US Patent and Trademark Office Re. U.S. Appl. No. 15/814,432. (5 pages).
International Preliminary Report on Patentability Dated Feb. 3, 2009 From the International Bureau of WIPO Re. Application No. PCT/IL2007/000970.
International Preliminary Report on Patentability Dated Apr. 9, 2009 From the International Bureau of WIPO Re. Application No. PCT/IL2006/000998.
International Search Report Dated Jun. 13, 2008 From the International Searching Authority Re. Application No. PCT/IL2007/000970.
International Searching Report and the Written Opinion Dated Jun. 4, 2008 From the International Searching Authority Re. Application No. PCT/IL2006/00998.
Invitation to Remedy Deficiencies Pursuant to Rule 30(3) EPC / Rule 163(3) EPC Dated Nov. 26, 2013 From the European Patent Office Re. Application No. 13185969.6.
Notice of Allowance Dated Feb. 1, 2013 From the US Patent and Trademark Office Re. U.S. Appl. No. 11/991,077.
Notice Of Allowance Dated Apr. 5, 2019 From the US Patent and Trademark Office Re. U.S. Appl. No. 15/209,776. (10 pages).
Notice of Allowance Dated Aug. 5, 2022 from US Patent and Trademark Office Re. U.S. Appl. No. 16/454,168. (6 pages).
Notice of Allowance Dated Oct. 9, 2014 From the US Patent and Trademark Office Re. U.S. Appl. No. 12/309,817.
Notice Of Allowance Dated Mar. 14, 2016 From the US Patent and Trademark Office Re. U.S. Appl. No. 13/909,128.
Notice of Allowance Dated Dec. 18, 2020 From the US Patent and Trademark Office Re. U.S. Appl. No. 15/814,432. (5 Pages).
Notice of Allowance Dated Jan. 26, 2015 From the US Patent and Trademark Office Re. U.S. Appl. No. 12/309,817.
Notice Of Allowance Dated Jul. 28, 2017 From the US Patent and Trademark Office Re. U.S. Appl. No. 14/720,853. (9 pages).
Notice of Non-Compliant Amendment Dated Sep. 2, 2015 From the US Patent and Trademark Office Re. U.S. Appl. No. 13/909,128.

(56) References Cited

OTHER PUBLICATIONS

Official Action Dated Sep. 5, 2018 From the US Patent and Trademark Office Re. U.S. Appl. No. 15/209,776. (19 pages).
Official Action Dated Apr. 6, 2020 From the US Patent and Trademark Office Re. U.S. Appl. No. 15/814,432. (14 Pages).
Official Action Dated Dec. 6, 2012 From the US Patent and Trademark Office Re. U.S. Appl. No. 12/309,817.
Official Action Dated May 9, 2013 From the US Patent and Trademark Office Re. U.S. Appl. No. 12/309,817.
Official Action Dated Aug. 11, 2011 From the US Patent and Trademark Office Re. U.S. Appl. No. 11/991,077.
Official Action Dated Jan. 12, 2022 from US Patent and Trademark Office Re. U.S. Appl. No. 16/454,168. (44 pages).
Official Action Dated Mar. 13, 2012 From the US PAtent and Trademark Office Re. U.S. Appl. No. 11/991,077.
Official Action Dated Feb. 14, 2014 From the US Patent and Trademark Office Re. U.S. Appl. No. 12/309,817.
Official Action Dated Oct. 15, 2015 From the US Patent and Trademark Office Re. U.S. Appl. No. 13/909,128.
Official Action Dated Apr. 17, 2017 from the US Patent and Trademark Office Re. U.S. Appl. No. 14/720,853. (7 pages).
Official Action Dated Oct. 18, 2011 From the US Patent and Trademark Office Re. U.S. Appl. No. 12/309,817.
Official Action Dated Mar. 22, 2018 From the US Patent and Trademark Office Re. U.S. Appl. No. 15/209,776. (97 pages).
Official Action Dated Oct. 24, 2012 From the US PAtent and Trademark Office Re. U.S. Appl. No. 11/991,077.
Official Action Dated May 25, 2011 From the US PAtent and Trademark Office Re. U.S. Appl. No. 11/991,077.
Official Action Dated Aug. 26, 2016 From the US Patent and Trademark Office Re. U.S. Appl. No. 14/720,853.
Official Action Dated Mar. 26, 2012 From the US Patent and Trademark Office Re. U.S. Appl. No. 12/309,817.
Official Action Dated Sep. 26, 2019 From the US Patent and Trademark Office Re. U.S. Appl. No. 15/814,432. (33 pages).
Partial European Search Report Dated Mar. 20, 2014 From the European Patent Office Re. Application No. 13185969.6.
Patent Examination Report Dated Jan. 15, 2014 From the Australian Government, IP Australia Re. Application No. 2012262726.
Patent Examination Report Dated Aug. 22, 2014 From the Australian Government, IP Australia Re. Application No. 2012262726.
Patent Examination Report Dated Nov. 25, 2016 From the Australian Government, IP Australia Re. Application No. 2015203310. (4 Pages).
Response Dated Jan. 2, 2012 to Second Written Opinion of Aug. 5, 2011 From the Austrian Patent Office on Behalf of the Intellectual Property Office of Singapore Re. Application No. 200801730-3.
Response Dated Feb. 8, 2011 to Communication Pursuant to Rules 70(2) and 70a(2) EPC of Aug. 10, 2010 From the European Patent Office Re. Application No. 06766237.9.
Response Dated Nov. 14, 2011 to Official Action of Aug. 11, 2011 From the US Patent and Trademark Office Re. U.S. Appl. No. 11/991,077.
Response Dated Dec. 23, 2010 to Communication Pursuant to Rules 70(2) and 70a(2) EPC of Aug. 10, 2010 From the European Patent Office Re. Application No. 06766237.9.
Response Dated Jun. 23, 2011 to Official Action of May 25, 2011 From the US PAtent and Trademark Office Re. U.S. Appl. No. 11/991,077.
Response Dated Nov. 24, 2011 to Communication Pursuant to Rules 70(2) and 70a(2) EPC of May 25, 2011 From the European Patent Office Re. Application No. 06766237.9.
Response Dated Dec. 28, 2011 to Examiner's Report of Aug. 29, 2011 From the Australian Government IP Australia Re. Application No. 2006286149.
Restriction Official Action Dated Oct. 7, 2021 from US Patent and Trademark Office Re. U.S. Appl. No. 16/454,168. (9 pages).
Restriction Official Action Dated Jun. 11, 2015 From the US Patent and Trademark Office Re. U.S. Appl. No. 13/909,128.
Restriction Official Action Dated Sep. 20, 2017 From the US Patent and Trademark Office Re. U.S. Appl. No. 15/209,776.(7 pages).
Search Report and Written Opinion Dated Apr. 3, 2013 From the Intellectual Property Office of Singapore Issued by the Austrian Patent Office on Mar. 1, 2013 Re. Application No. 201200039-4.
Search Report and Written Opinion Dated Jan. 26, 2010 Received From the Intellectual Property Office of Singapore on Aug. 16, 2010 Issued by the Austrian Patent Office, Service and Information Center (TRF) Re. Application No. 200801730-3.
Second Supplementary European Search Report and the European Search Opinion Dated Apr. 20, 2011 From the European Patent Office Re. Application No. 06766237.9.
Second Written Opinion Dated Aug. 5, 2011 From the Austrian Patent Office on Behalf of the Intellectual Property Office of Singapore Re. Application No. 200801730-3.
Supplementary European Search Report and the European Search Opinion Dated Jul. 23, 2010 From the European Patent Office Re. Application No. 06766237.9.
Written Opinion Dated Jun. 13, 2008 From the International Searching Authority Re. Application No. PCT/IL2007/000970.
Amit et al. "Clonally Derived Human Embryonic Stem Cell Lines Maintain Pluripotency and Proliferative Potential for Prolonged Periods of Culture", Developmental Biology, 227: 271-278, 2000.
Amit et al. "Dynamic Suspension Culture for Scalable Expansion of Undifferentiated Human Pluripotent Stem Cells", Nature Protocols, XP008146753, 6(5): 572-579, May 1, 2011.
Amit et al. "Feeder Layer- and Serum-Free Culture of Human Embryonic Stem Cells", Biology of Reproduction, XP002466324, 70(3): 837-845, Jan. 1, 2004. Abstract, p. 837-838, ES Cell Culture.
Amit et al. "Feeder-Free Culture of Human Embryonic Stem Cells", Methods in Enzymology, XP009105807, 420(3): 37-49, Jan. 1, 2006.
Amit et al. "Human Feeder Layers for Human Embryonic Stem Cells", Biology of Reproduction, 68: 2150-2156, 2003.
Amit et al. "Suspension Culture of Undifferentiated Human Embryonic and Induced Pluripotent Stem Cells", Stem Cell Reviews and Reports, 6(2): 248-259, Apr. 30, 2010.
Cheng et al. "Human Adult Marrow Cells Support Prolonged Expansion of Human Embryonic Stem Cells in Culture", Stem Cells, 21: 131-142, 2003.
Cowan et al. "Derivation of Embryonic Stem-Cell Lines From Human Blastocysts", The New England Journal of Medicine, 350(13): 1353-1356, 2004.
Daheron et al. "LIF/STAT3 Signaling Fails to Maintain Self-Renewal of Human Embryonic Stem Cells", Stem Cells, 22: 770-778, 2004.
GenBank GenBnak Overview, Printed from Website, 2, 2022.
Hovatta et al. "A Culture System Using Human Foreskin Fibroblasts as Feeder Cells Allows Production of Human Embryonic Stem Cells".
Humphrey et al. "Maintenance of Pluripotency in Human Embryonic Stem Cells Is STAT3 Independent", Stem Cells, XP002463152, 22(4): 522-530, Jan. 1, 2004.
Klimanskaya et al. "Human Embryonic Stem Cells Derived Without Feeder Cells", The Lancet, 365: 1636-1641, Mar. 7, 2005. p. 1636, Methods.
Kollet et al. "The Soluble Interleukin-6 (IL-6) Receptor/IL-6 Fusion Protein Enhances In Vitro Maintenance and Proliferation of Human CD34+CD38−/Low Cells Capable of Repopulating Severe Combined Immunodeficiency Mice", Blood, 94(3): 923-931, Aug. 1, 1999.
Levenstein et al. "Basic FGF Support of Human Embryonic Stem Cell Self-Renewal", Stem Cells, 24(3): 568-574, Mar. 2006.
Ludwig et al. "Derivation of A Human Embryonic Stem Cells in Defined Conditions", Nature Biotechnology, 24(2): 185-187, Feb. 2006.
Mallon et al. "Toward Xeno-Free Culture of Human Embryonic Stem Cells", International Journal of Biochemistry and Cell Biology, 38: 1063-1075, Jan. 23, 2006.
Nichols et al. "Derivation of Germline Competent Embryonic Stem Cells With a Combination of Interleukin-6 and Soluble Interleukin-6 Receptor", Experimental Cell Research, 215(1): 237-239, Nov. 1994.

(56) References Cited

OTHER PUBLICATIONS

Niwa et al. "Self-Renewal of Pluripotent Embryonic Stem Cells Is Mediated via Activation of STAT3", Genes & Development, 12: 2048-2060, 1998.
Ueda et al. "Establishment of Rat Embryonic Stem Cells and Making of Chimera Rats", PLoS one 3(7):2 e2800, 1-9, Jul. 2008.
Van der Jeught et al. "Application of Small Molecules Favoring Naive Pluripotency During Human Embryonic Stem Cell Derivation", Cellular Reprogramming, XP055224755, 17(3): 170-180, Jun. 1, 2015.
Xu et al. "Basic Fibroblast Growth Factor Supports Undifferentiated Human Embryonic Stem Cell Growth Without Conditioned Medium", Stem Cells, 23: 315-323, 2005. Abstract, p. 316, hES Culture.
Xu et al. "Feeder-Free Growth of Undifferentiated Human Embryonic Stem Cells", Nature Biotechnology, XP002672078, 19(10): 971-974, Oct. 2001.
Yamanishi et al. "Roles of Transforming Growth Factor Beta in Inhibition of Androgen-Induced Growth of Shionogi Carcinoma Cells in Serum-Free Medium", Cancer Research, 50: 6179-6183, Oct. 1, 1990.
Yoshida et al. "Maintenance of the Pluripotential Phenotype of Embryonic Stem Cells Through Direct Activation of GP130 Signalling Pathways", Mechanisms of Development, 45: 163-171, 1994.
Zhang et al. "Enhacement of Oligodendrocyte Differentiation from Murine Embryonic Stem Cells by an Activator of gp 130 Signaling", Stem Cells, 22(3): 344-354, May 2004.
Zur Nieden et al. "Embryonic Stem Cells Remain Highly Pluripotent Following Long Term Expansion as Aggregates in Suspension Bioreactors", Journal of Biotechnology, 129: 421-432, 2007.

\* cited by examiner

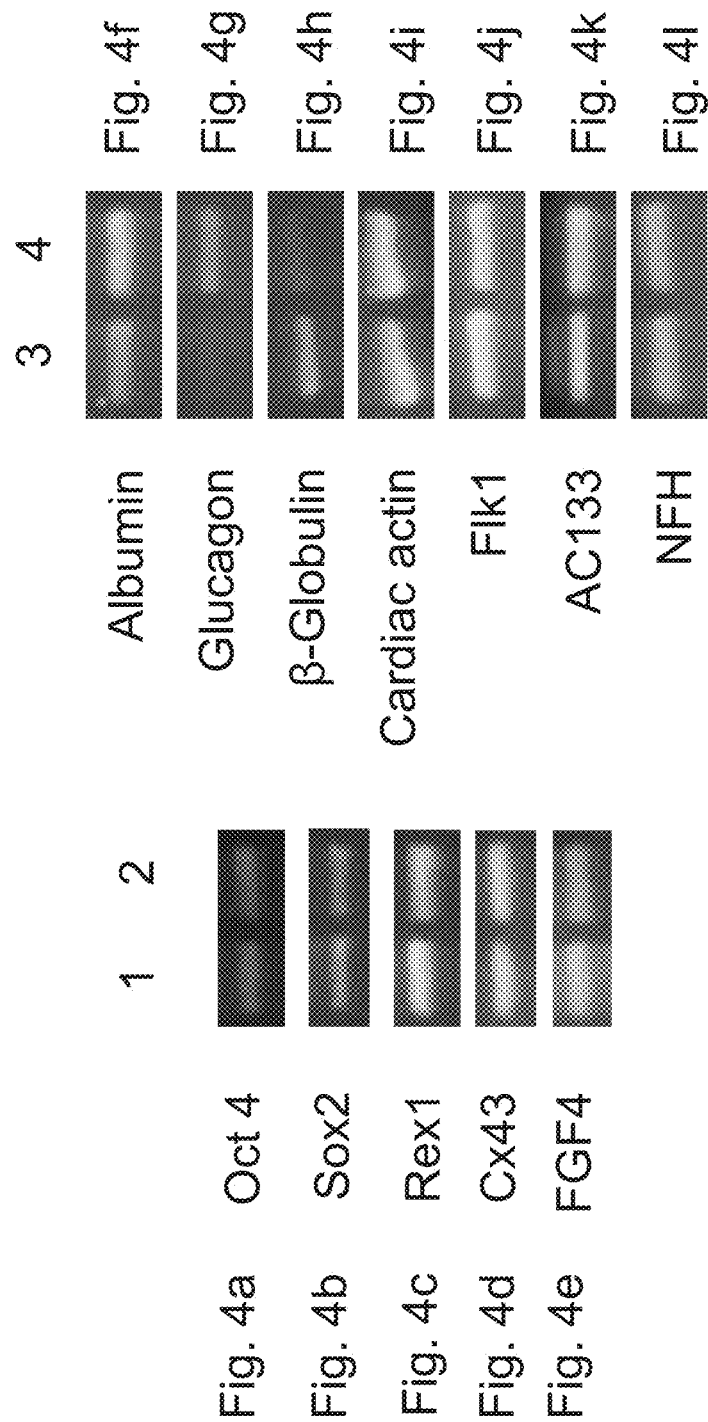

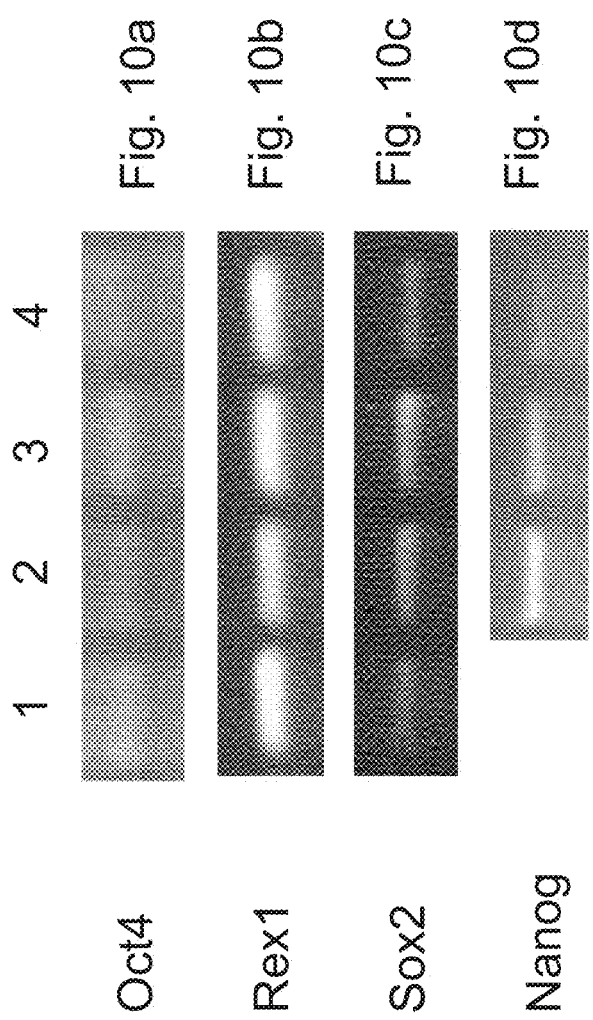

MEDIA FOR CULTURING STEM CELLS

RELATED APPLICATIONS

This application is a division of U.S. patent application Ser. No. 16/454,168 filed on Jun. 27, 2019, which is a division of U.S. patent application Ser. No. 15/209,776 filed on Jul. 14, 2016, now U.S. Pat. No. 10,385,312, which is a continuation of U.S. patent application Ser. No. 13/909,128 filed on Jun. 4, 2013, now U.S. Pat. No. 9,404,079, which is a division of U.S. patent application Ser. No. 11/991,077 filed on Feb. 27, 2008, now U.S. Pat. No. 8,476,070, which is a National Phase of PCT Patent Application No. PCT/IL2006/000998 having International Filing Date of Aug. 29, 2006, which claims the benefit of priority of U.S. Provisional Patent Application Nos. 60/834,795 filed on Aug. 2, 2006 and 60/711,668 filed on Aug. 29, 2005. The contents of the above Applications are all incorporated herein by reference.

SEQUENCE LISTING STATEMENT

The XML file, entitled 94187SequenceListing.xml, created on Oct. 24, 2022, comprising 42,278 bytes, submitted concurrently with the filing of this application is incorporated herein by reference.

FIELD AND BACKGROUND OF THE INVENTION

The present invention relates to culture media, cell cultures and methods of culturing stem cells such as under defined and xeno-free culturing conditions.

Human Embryonic stem cells (hESCs) were traditionally cultured and derived using the conventional methods employed for mouse ESCs, i.e., in the presence of a medium supplemented with fetal bovine serum (FBS) and feeder-layers consisting of inactivated mouse embryonic fibroblasts (MEFs) (Thomson et al, 1998). However, for use in cell-based therapy, hESC cultures should be well-defined and xeno-free (i.e., devoid of any animal contaminant) in terms of culture components. In recent years, extensive investigation into improving the culture systems for hESCs has yielded the following advances: the ability to grow cells in serum-free conditions (Amit et al, 2000); maintenance of the cells in an undifferentiated state on a Matrigel™ matrix with 100% MEF-conditioned medium (Xu et al, 2001); and the use of either human embryonic fibroblasts, adult Fallopian tube epithelium (Richards et al, 2002) or foreskin fibroblasts (Amit et al, 2003; Hovatta et al, 2003) as feeder layers. However, while the use of MEF-conditioned medium or a Matrigel™ matrix (which contains components from animal cells) may expose the hESCs to animal pathogens, the batch-specific variations may affect the quality of the culture. On the other hand, although human feeder-layer-based culture systems are xeno-free, they require the simultaneous growth of both feeder cell layers and hESCs, which limits the potential of large-scale culturing of hESCs. Moreover, culture systems based on feeder cells or conditioned medium are not well-defined and thus cannot be accurately repeated due to differences between the various lines of feeder-cells.

To overcome such limitations, attempts have been made to culture hESCs in feeder-layer-free culture systems devoid of conditioned medium. Xu C., et al. (Stem Cells, 2005, 23:315-23) developed a culture system based on a Matrigel™ matrix and a medium supplemented with Serum Replacement™ (SR), basic fibroblast growth factor (bFGF), with or without the addition of the Flt-3 ligand to the culture medium. However, under these conditions, the background differentiation of the ESCs was 20 or 28%, respectively, which is higher than observed for hESCs when cultured on MEFs. Another culturing system based a Matrigel™ matrix and a medium supplemented with bFGF and Noggin, an antagonist of bone morphogenetic proteins (BMPs), resulted in a background differentiation of 10% (Xu R H., et al., 2005, Nat Methods. 2: 185-190). However, since both of these systems rely on Matrigel™ as a culturing matrix, their use for cell-based therapy is limited. To avoid animal contaminants, the present inventors have previously developed a culture system based on a fibronectin matrix and a medium supplemented with 20% SR, transforming growth factor β1 (TGFβ$_1$) and bFGF (Amit et al, 2004). Under these conditions, the cells maintained hESC features for more than 32 passages. A further step towards defined culture conditions for hESCs culture was recently achieved by Ludwig and colleague (Ludwig et al, 2006) when using a matrix consisted of the combination of human collagen IV, fibronectin, laminin and vitronectin and a medium supplemented with human serum albumin, bFGF and TGFβ$_1$. Such conditions enabled the derivation and culturing of hESCs under defined and feeder layer-free culture conditions. However, hESCs cultured in these conditions exhibited chromosomal instability of the cells following extended periods in culture. For example, one of the isolated hESC lines was reported to harbor a karyotype of 47,XXY after 4 months of continuous culturing and a second line, which was initially normal, converted to trisomy 12 between 4 and 7 months of culturing. Thus, improvements of the feeder-free, xeno-free culturing systems of hESCs are highly needed.

Recent studies discussed the possible involvement of several intracellular transduction pathways in hESC renewal and maintenance of "stemness" identity, but the mechanism underlining hESC self-maintenance is still unrevealed. Sato and colleagues (Sato et al, 2004) suggested that the Wnt pathway is involved in hESC self-renewal. A later publication by the same group indicates that the TGFβ pathway plays a crucial role in cell-fate determination and holds interconnections with the Wnt signaling pathway in maintaining hESC features (James, D., et al., 2005). These results are consistent with the feeder layer-free culture method suggested by the present inventors (Amit et al, 2004), which is based on the addition of TGFβ$_1$, bFGF and/or LIF to a culture medium which includes serum or serum replacement. In addition, the mechanism by which bFGF involves in hESC' self-maintenance has yet to be proven. Another candidate for the role of maintaining hESC properties is Noggin—an inhibitor of the BMPs signaling pathway (Xu R H., et al, 2005). However, to date, not Noggin itself or any Noggin analog were found in MEF-conditioned media.

Mouse ESCs can be continuously cultured without feeder layers provided that leukemia inhibitory factor (LIF) is added to the culture medium. However, accumulating data regarding hESCs suggest that LIF has no effect on preventing hESC differentiation (Thomson et al, 1998; Reubinof et al, 2000). In addition, activation of key proteins of the LIF cellular pathway, such as signal transducer and activator of transcription 3 (STAT3) was found to be weak or absent in hESCs (Daheron et al, 2004; Humphrey et al, 2004; Sato et al, 2004). The gp130 receptor, which is activated by ligands such as LIF, interleukin 6 (IL-6) and a chimera made of IL-6 and its soluble IL6 receptor (the IL6RIL6 chimera; Chebath et al, 1997), was shown to positively affect the mouse ESCs self-maintenance via STAT3 (Williams et al, 1988; Niwa et al, 1998; Smith et al, 1988). In hematopoietic stem cells, the IL6RIL6 chimera exhibited a much higher affinity for human gp130 and was found to be more potent in increasing proliferation of progenitor cells than the mixture of IL-6 and the soluble IL6 receptor (Kollet et al, 1999). On the other hand, the IL6RIL6 chimera induced differentiation of ESC-derived oligodendrocyte precursors (Zhang P L., et al., 2006, Mol. Cell Neurosci. 31: 387-398). In a recent study, Nichols et al., (1994) demonstrated that the IL6RIL6 chimera is capable of supporting mouse ESC culturing and derivation. On the other hand, Daheron et al. (2004) showed that although the LIFRβ and the signaling subunit gp130 are expressed in hESCs and that human LIF can induce STAT3 phosphorylation and nuclear translocation in hESCs, human LIF is unable to maintain the pluripotent state of hESCs. In addition, Humphrey et al. (2004) found that hESCs rapidly differentiate when cultured in a medium containing members of the IL-6 family of cytokines such as LIF, IL-6 or a complex of the soluble IL-6 receptor and IL-6 (the "hyper-IL-6") and concluded that maintenance of pluropotency in human ESCs is STAT independent. Thus, it is currently accepted that in contrast to mouse ESCs which can be maintained in the undifferentiated state in the presence of activators of the gp130 receptor, culturing of human ESCs in the presence of LIF, IL6 or the hyper-IL-6 results in differentiation of the hESCs.

There is thus a widely recognized need for, and it would be highly advantageous to have, a defined, xeno-free medium suitable for maintaining stable, undifferentiated and pluripotent hESCs devoid of the above limitations.

SUMMARY OF THE INVENTION

According to one aspect of the present invention there is provided a culture medium being serum-free, xeno-free, feeder-free and protein carrier-free and capable of maintaining stem cells in an undifferentiated state.

According to another aspect of the present invention there is provided a cell culture comprising a stem cell and a culture medium, said culture medium being serum-free, xeno-free, feeder-free and protein carrier-free and capable of maintaining said stem cells in an undifferentiated state.

According to yet another aspect of the present invention there is provided a method of expanding and maintaining stem cells in an undifferentiated state, the method comprising culturing the stem cells in a culture medium being serum-free, xeno-free, feeder-free and protein carrier-free and capable of maintaining the stem cells in an undifferentiated state, thereby expanding and maintaining the stem cells in the undifferentiated state.

According to still another aspect of the present invention there is provided a method of deriving an embryonic stem cell line, the method comprising: (a) obtaining an embryonic stem cell from a pre-implantation stage blastocyst, post-implantation stage blastocyst and/or a genital tissue of a fetus; and (b) culturing said embryonic stem cell in a culture medium being serum-free, xeno-free, feeder-free and protein carrier-free and capable of maintaining said embryonic stem cell in an undifferentiated state; thereby deriving the embryonic stem cell line.

According to an additional aspect of the present invention there is provided a method of generating lineage-specific cells from embryonic stem cells, the method comprising: (a) culturing the embryonic stem cells in a culture medium being serum-free, xeno-free, feeder-free and protein carrier-free and capable of maintaining the embryonic stem cells in an undifferentiated state, to thereby obtain expanded, undifferentiated embryonic stem cells; (b) subjecting said expanded, undifferentiated embryonic stem cells to culturing conditions suitable for differentiating and/or expanding lineage specific cells; thereby generating the lineage-specific cells from the embryonic stem cells.

According to yet an additional aspect of the present invention there is provided a method of generating embryoid bodies from embryonic stem cells, the method comprising: (a) culturing the embryonic stem cells in a culture medium being serum-free, xeno-free, feeder-free and protein carrier-free and capable of maintaining the embryonic stem cells in an undifferentiated state, to thereby obtain expanded, undifferentiated embryonic stem cells; and (b) subjecting said expanded, undifferentiated embryonic stem cells to culturing conditions suitable for differentiating said embryonic stem cells to embryoid bodies; thereby generating the embryoid bodies from the embryonic stem cells.

According to still an additional aspect of the present invention there is provided a method of generating lineage-specific cells from embryonic stem cells, the method comprising: (a) culturing the embryonic stem cells in a culture medium being serum-free, xeno-free, feeder-free and protein carrier-free and capable of maintaining the embryonic stem cells in an undifferentiated state, to thereby obtain expanded, undifferentiated embryonic stem cells; (b) subjecting said expanded, undifferentiated embryonic stem cells to culturing conditions suitable for differentiating said expanded, undifferentiated embryonic stem cells to embryoid bodies; and (c) subjecting cells of said embryoid bodies to culturing conditions suitable for differentiating and/or expanding lineage specific cells; thereby generating the lineage-specific cells from the embryonic stem cells.

According to a further aspect of the present invention there is provided a culture medium comprising a TGFβ isoform and being devoid of serum, serum replacement and protein carrier, wherein the culture medium is capable of maintaining stem cells in an undifferentiated state.

According to yet a further aspect of the present invention there is provided a cell culture comprising a stem cell and a culture medium, said culture medium comprising a TGFβ isoform and being devoid of serum, serum replacement and protein carrier, wherein said culture medium is capable of maintaining said stem cell in an undifferentiated state.

According to still a further aspect of the present invention there is provided a method of expanding and maintaining stem cells in an undifferentiated state, the method comprising culturing the stem cells in a culture medium which comprises a TGFβ isoform and being devoid of serum, serum replacement and protein carrier, said culture medium is capable of maintaining the stem cells in an undifferentiated state, thereby expanding and maintaining the stem cells in the undifferentiated state.

According to still a further aspect of the present invention there is provided a method of deriving an embryonic stem cell line, the method comprising: (a) obtaining an embryonic stem cell from a pre-implantation stage blastocyst, post-implantation stage blastocyst and/or a genital tissue of a fetus; and (b) culturing said embryonic stem cell in a culture medium which comprises a TGFβ isoform and being devoid of serum, serum replacement and protein carrier, said culture medium is capable of maintaining the embryonic stem cells in an undifferentiated state, thereby deriving the embryonic stem cell line.

According to still a further aspect of the present invention there is provided a method of generating lineage-specific cells from embryonic stem cells, the method comprising: (a) culturing the embryonic stem cells in a culture medium which comprises a TGFβ isoform and being devoid of serum, serum replacement and protein carrier, said culture medium is capable of maintaining the embryonic stem cells in an undifferentiated state, to thereby obtain expanded, undifferentiated embryonic stem cells; and (b) subjecting said expanded, undifferentiated embryonic stem cells to culturing conditions suitable for differentiating and/or expanding lineage specific cells; thereby generating the lineage-specific cells from the embryonic stem cells.

According to still a further aspect of the present invention there is provided a method of generating embryoid bodies from embryonic stem cells, the method comprising: (a) culturing the embryonic stem cells in a culture medium which comprises a TGFβ isoform and being devoid of serum, serum replacement and protein carrier, said culture medium is capable of maintaining the embryonic stem cells in an undifferentiated state, to thereby obtain expanded, undifferentiated embryonic stem cells; and (b) subjecting said expanded, undifferentiated embryonic stem cells to culturing conditions suitable for differentiating said embryonic stem cells to embryoid bodies; thereby generating the embryoid bodies from the embryonic stem cells.

According to still a further aspect of the present invention there is provided a method of generating lineage-specific cells from embryonic stem cells, the method comprising: (a) culturing the embryonic stem cells in a culture medium which comprises a TGFβ isoform and being devoid of serum, serum replacement and protein carrier, said culture medium is capable of maintaining the embryonic stem cells in an undifferentiated state, to thereby obtain expanded, undifferentiated embryonic stem cells; (b) subjecting said expanded, undifferentiated embryonic stem cells to culturing conditions suitable for differentiating said expanded, undifferentiated embryonic stem cells to embryoid bodies; and (c) subjecting cells of said embryoid bodies to culturing conditions suitable for differentiating and/or expanding lineage specific cells; thereby generating the lineage-specific cells from the embryonic stem cells.

According to still a further aspect of the present invention there is provided a culture medium comprising an IL6RIL6 chimera, wherein the culture medium is capable of maintaining human embryonic stem cells in an undifferentiated state.

According to still a further aspect of the present invention there is provided a cell culture comprising a human embryonic stem cell and a culture medium, said culture medium comprising an IL6RIL6 chimera, wherein said culture medium is capable of maintaining said human embryonic stem cell in an undifferentiated state.

According to still a further aspect of the present invention there is provided a method of expanding and maintaining human embryonic stem cells in an undifferentiated state, the method comprising culturing the human embryonic stem cells in a culture medium which comprises an IL6RIL6 chimera, said culture medium is capable of maintaining the human embryonic stem cells in an undifferentiated state, thereby expanding and maintaining the embryonic stem cells in the undifferentiated state.

According to still a further aspect of the present invention there is provided a method of deriving a human embryonic stem cell line, the method comprising: (a) obtaining a human embryonic stem cell from a pre-implantation stage blastocyst, post-implantation stage blastocyst and/or a genital tissue of a fetus; and (b) culturing said human embryonic stem cell in a culture medium which comprises an IL6RIL6 chimera, said culture medium is capable of maintaining the human embryonic stem cells in an undifferentiated state, thereby deriving the embryonic stem cell line.

According to still a further aspect of the present invention there is provided a method of generating lineage-specific cells from embryonic stem cells, the method comprising: (a) culturing the embryonic stem cells in a culture medium which comprises an IL6RIL6 chimera, said culture medium is capable of maintaining the embryonic stem cells in an undifferentiated state, to thereby obtain expanded, undifferentiated embryonic stem cells; and (b) subjecting said expanded, undifferentiated embryonic stem cells to culturing conditions suitable for differentiating and/or expanding lineage specific cells; thereby generating the lineage-specific cells from the embryonic stem cells.

According to still a further aspect of the present invention there is provided a method of generating embryoid bodies from embryonic stem cells, the method comprising: (a) culturing the embryonic stem cells in a culture medium which comprises an IL6RIL6 chimera, said culture medium is capable of maintaining the embryonic stem cells in an undifferentiated state, to thereby obtain expanded, undifferentiated embryonic stem cells; and (b) subjecting said expanded, undifferentiated embryonic stem cells to culturing conditions suitable for differentiating said embryonic stem cells to embryoid bodies; thereby generating the embryoid bodies from the embryonic stem cells.

According to still a further aspect of the present invention there is provided a method of generating lineage-specific cells from embryonic stem cells, the method comprising: (a) culturing the embryonic stem cells in a culture medium which comprises an IL6RIL6 chimera, said culture medium is capable of maintaining the embryonic stem cells in an undifferentiated state, to thereby obtain expanded, undifferentiated embryonic stem cells; (b) subjecting said expanded, undifferentiated embryonic stem cells to culturing conditions suitable for differentiating said expanded, undifferentiated embryonic stem cells to embryoid bodies; and (c) subjecting cells of said embryoid bodies to culturing conditions suitable for differentiating and/or expanding lineage specific cells; thereby generating the lineage-specific cells from the embryonic stem cells.

According to further features in preferred embodiments of the invention described below, the embryonic stem cells are human embryonic stem cells.

According to still further features in the described preferred embodiments the culture medium comprising a TGFβ isoform.

According to still further features in the described preferred embodiments the culture medium being serum replacement-free.

According to still further features in the described preferred embodiments the culture medium comprising IL6RIL6 chimera.

According to still further features in the described preferred embodiments the culture medium comprising IL6RIL6 chimera and whereas said stem cells are human embryonic stem cells.

According to still further features in the described preferred embodiments the culture medium comprising IL6RIL6 chimera and whereas said embryonic stem cells are human embryonic stem cells.

According to still further features in the described preferred embodiments the stem cells are embryonic stem cells.

According to still further features in the described preferred embodiments the culture medium is capable of expanding said stem cells in an undifferentiated state.

According to still further features in the described preferred embodiments the protein carrier is albumin.

According to still further features in the described preferred embodiments culturing is effected in suspension.

According to still further features in the described preferred embodiments the suspension is devoid of substrate adherence.

According to still further features in the described preferred embodiments culturing is effected on a feeder-layer free matrix.

According to still further features in the described preferred embodiments the feeder-layer free matrix is a fibronectin matrix.

According to still further features in the described preferred embodiments the culturing is effected on feeder cells.

According to still further features in the described preferred embodiments the culture medium is xeno-free.

According to still further features in the described preferred embodiments culturing is effected in xeno-free culturing conditions.

According to still further features in the described preferred embodiments the TGFβ isoform is a TGFβ isoform 1 (TGFβ$_1$).

According to still further features in the described preferred embodiments the TGFβ isoform is a TGFβ isoform 3 (TGFβ$_3$).

According to still further features in the described preferred embodiments the TGFβ$_1$ is provided at a concentration of at least 0.06 ng/ml.

According to still further features in the described preferred embodiments the TGFβ$_1$ is provided at a concentration of 0.12 ng/ml.

According to still further features in the described preferred embodiments the TGFβ$_3$ is provided at a concentration of at least 0.5 ng/ml.

According to still further features in the described preferred embodiments the TGFβ$_3$ is provided at a concentration of 2 ng/ml.

According to still further features in the described preferred embodiments the culture medium comprises basic fibroblast growth factor (bFGF).

According to still further features in the described preferred embodiments the bFGF is provided at a concentration of at least 2 ng/ml.

According to still further features in the described preferred embodiments the bFGF is provided at a concentration of at least 4 ng/ml.

According to still further features in the described preferred embodiments the IL6RIL6 chimera is provided at a concentration of at least 25 ng/ml.

According to still further features in the described preferred embodiments the culture medium comprises serum or serum replacement.

According to still further features in the described preferred embodiments the culture medium is devoid of serum or serum replacement.

According to still further features in the described preferred embodiments the serum or serum replacement is provided at a concentration of at least 10%.

According to still further features in the described preferred embodiments the method further comprising isolating lineage specific cells following step (b).

According to still further features in the described preferred embodiments isolating lineage specific cells is effected by a mechanical separation of cells, tissues and/or tissue-like structures contained within said embryoid bodies.

According to still further features in the described preferred embodiments isolating lineage specific cells is effected by subjecting said embryoid bodies to differentiation factors to thereby induce differentiation of said embryoid bodies into lineage specific differentiated cells.

According to still further features in the described preferred embodiments the embryonic stem cell is a human embryonic stem cell.

According to still further features in the described preferred embodiments the embryonic stem cell is a primate embryonic stem cell.

The present invention successfully addresses the shortcomings of the presently known configurations by providing a well-defined, xeno-free culture media which comprise a TGFβ isoform or the IL6RIL6 chimera, which are capable of maintaining stem cells in an undifferentiated state.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings executed in color. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
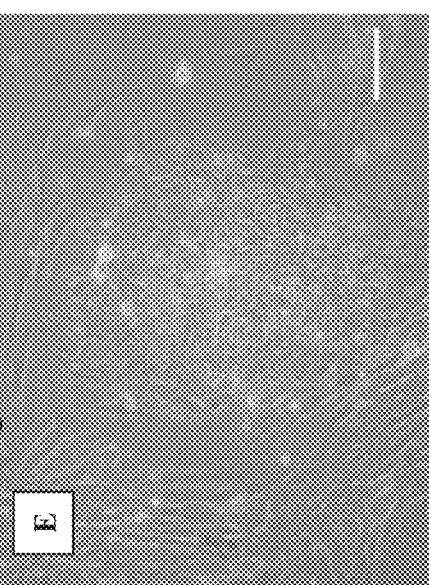
Figure 1B:
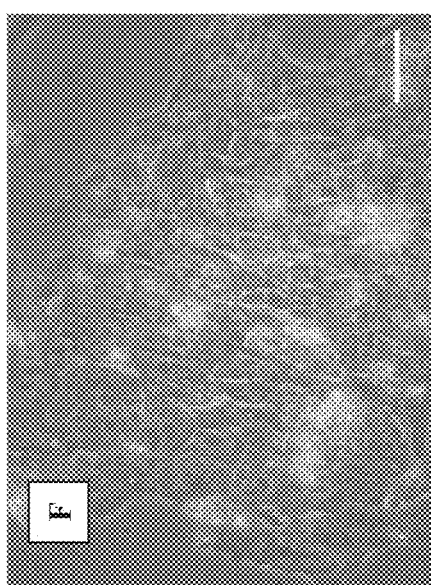
Figure 1C:
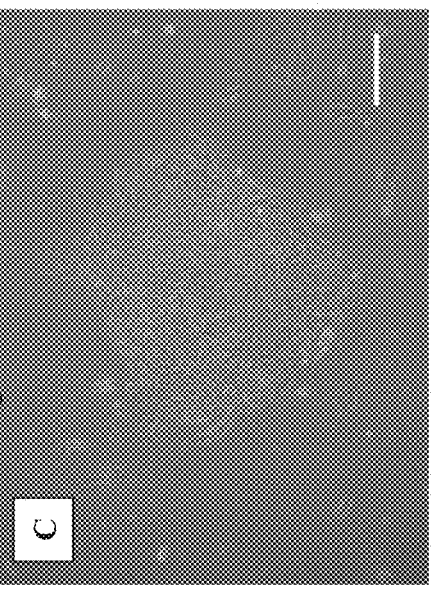
Figure 1D:
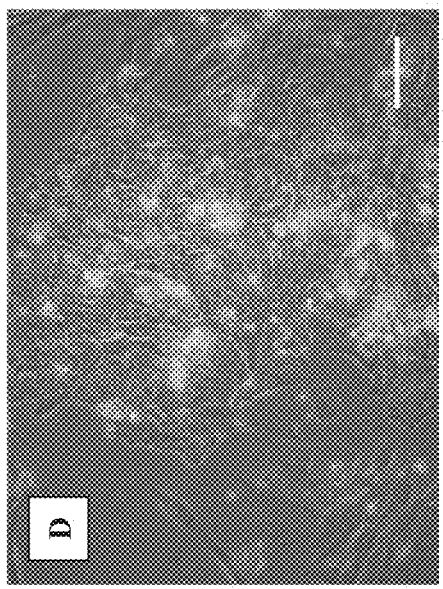
Figure 1E:
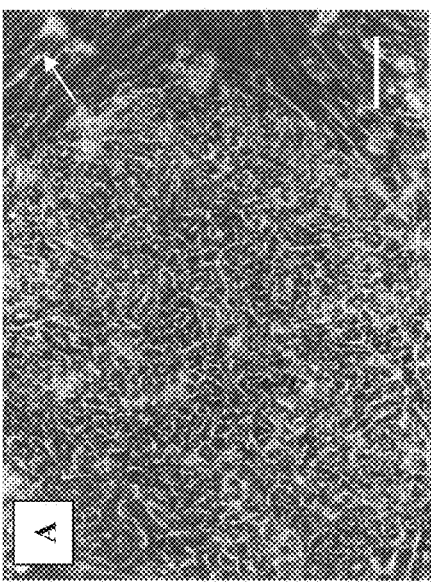
Figure 1F:
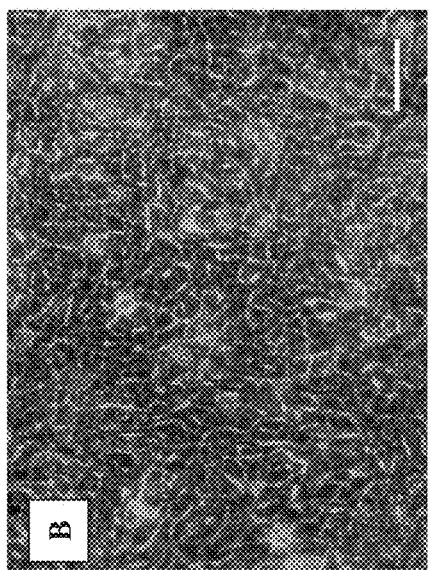

FIGS. 1a-1f are photomicrographs depicting examples of the morphology of undifferentiated ESC colonies and ESC single cells grown in various feeder-free culture systems. FIGS. 1a-1b—Undifferentiated I-3 colony cultured on a fibronectin-based feeder layer free culture system for 12 passages in the presence of a culture medium supplemented with 100 ng/ml of the IL6RIL6 chimera. Note the "auto-feeders" formed at the periphery of the colony (FIG. 1a, arrow). FIG. 1c—Undifferentiated I-3 colony cultured on a mouse laminin-based feeder layer free culture system for 7 passages in the presence of a culture medium supplemented with 100 ng/ml of the IL6RIL6 chimera. Note the absence of "auto-feeders". FIGS. 1d-1f—undifferentiated I-4 colonies cultured on a fibronectin-based feeder free culture system for 28 passages in the presence of a culture medium supplemented with 100 ng/ml of the IL6RIL6 chimera. Size bar for FIGS. 1a, 1c, 1d, 1e, 1f—20 µM; Size bar for FIG. 1b—50 µM.

Figure 2:
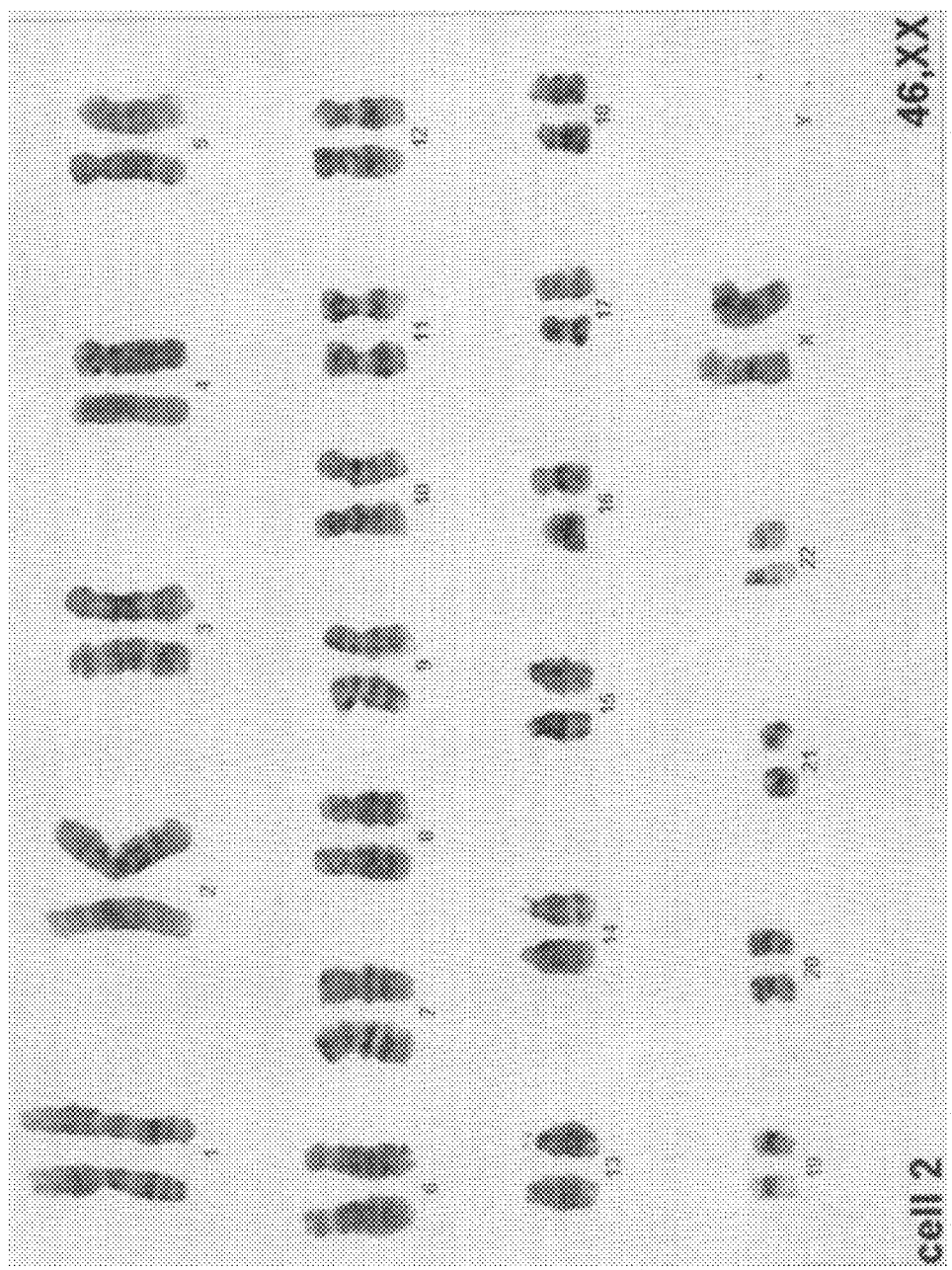

FIG. 2 depicts a normal karyotype of an exemplary hESC. The karyotype was examined after 7 passages of culturing in the presence of a culture medium containing 300 ng/ml of the IL6RIL6 chimera on a fibronectin feeder-free culture system. Note the presence of a normal 46,XX karyotype. Normal karyotype was also detected when the hESCs were cultured for 7 passages in the presence of a culture medium containing 100 ng/ml of the IL6RIL6 chimera on a fibronectin feeder-free culture system (not shown). Repeated test at passage 23 was found to be normal (not shown). 40 metaphases were examined from each sample.

Figure 3A:
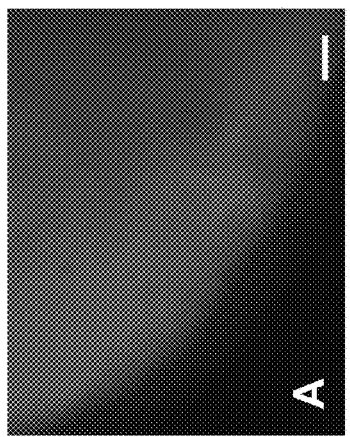
Figure 3B:
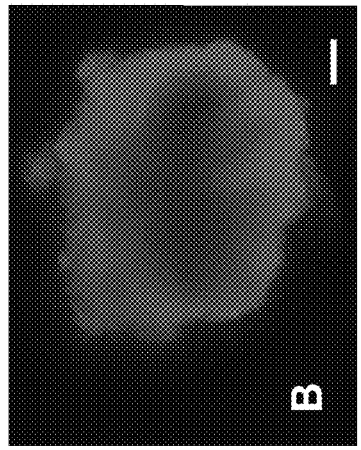
Figure 3C:
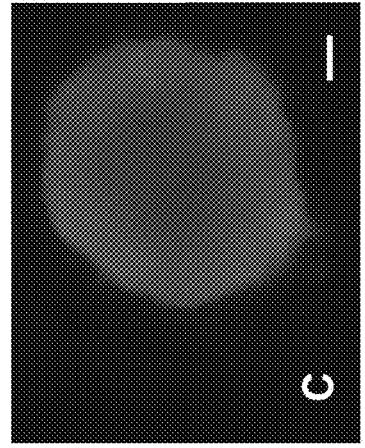

FIGS. 3a-3c are photomicrographs depicting immunofluorescence staining of undifferentiated colonies stained with surface markers specific to the hESC undifferentiated stage. Undifferentiated I-4 hESCs were cultured on a fibronectin feeder-free culture system for 27 passages in the presence of 100 ng/ml of the IL6RIL6 chimera and were subjected to immunostaining with Tra-1-60 (FIG. 3a), Oct 4 (FIG. 3b) or SSEA-4 (FIG. 3c). Size bar=20 μM.

FIGS. 4a-4l are RT-PCR analyses depicting the expression of representative genes of the undifferentiated stage and of the three embryonic germ layers in hESCs grown on human fibronectin feeder free culture system or in embryoid bodies (EBs) derived therefrom. Lane 1—Cell line I-3 cultured for 12 passages in CM100 (100 ng/ml of the IL6RIL6 chimera). Lane 2—Cell line I-3 cultured for 12 passages in 300 ng/ml of the IL6RIL6 chimera. Lane 3—10-day-old EBs derived from I-3 cells which were cultured for 10 passages in CM100. Lane 4—EBs derived from I-3 cells which were cultured for 10 passages in 300 ng/ml of the IL6RIL6 chimera. FIG. 4a—Oct4; FIG. 4b—Sox2; FIG. 4c—Rex1; FIG. 4d—Cx43; FIG. 4e—FGF4; FIG. 4f—Albumin; FIG. 4g—Glucagon; FIGS. 4h—β-Globulin; FIG. 4i—Cardiac actin; FIG. 4j—Flk1; FIGS. 4k—AC133; FIG. 4l—NFH.

Figure 5A:
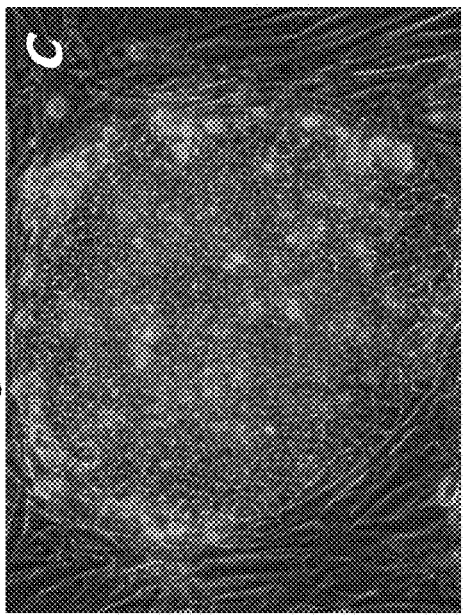
Figure 5C:
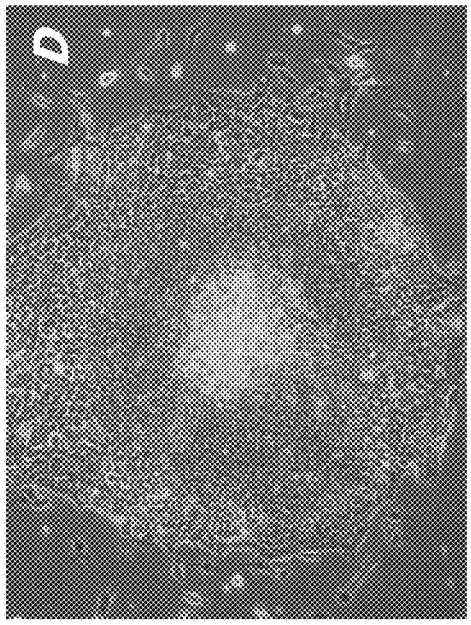
Figure 5B:
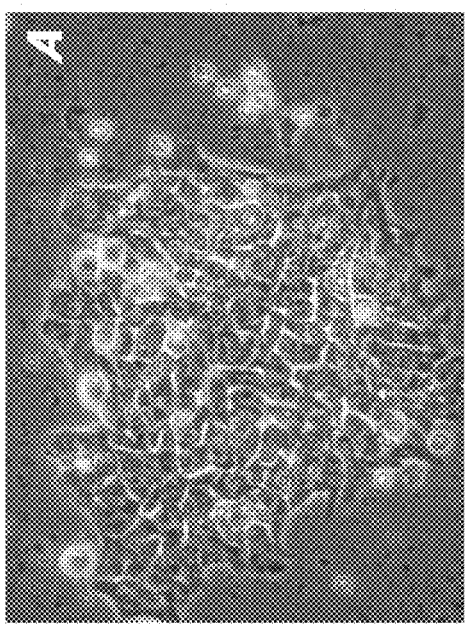
Figure 5D:
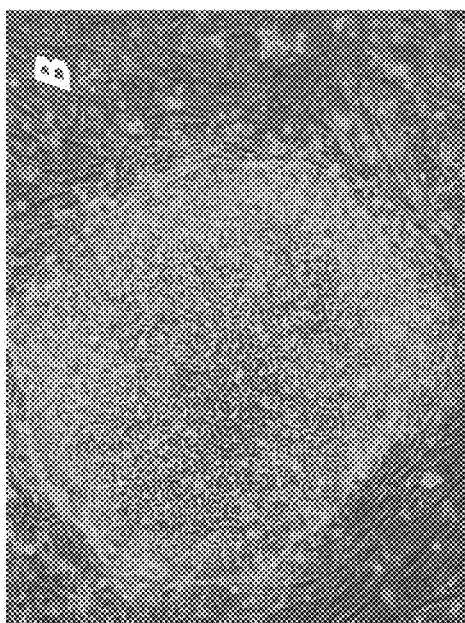

FIGS. 5a-5d are photomicrographs depicting the morphology of undifferentiated hES colonies and hES single cells cultured in various culture systems in the presence of the TGFβ-containing culture media. FIGS. 5a—I4 ESCs cultured for 28 passages on a Matrigel™ matrix with the D1 medium; FIGS. 5b—I4 hESCs cultured for 9 passages on MEFs with the HA16 medium; FIGS. 5c—I4 hESCs cultured for 20 passages on foreskins fibroblasts with the D2 medium; FIGS. 5d—I4 hESCs cultured for 11 passages on a human fibronectin matrix with the D2 medium. Note the undifferentiated morphology after prolonged culturing with the unique TGFβ-containing media types. Magnifications are ×15 for FIGS. 5a-5d.

Figures 6A, 6B, 6C:
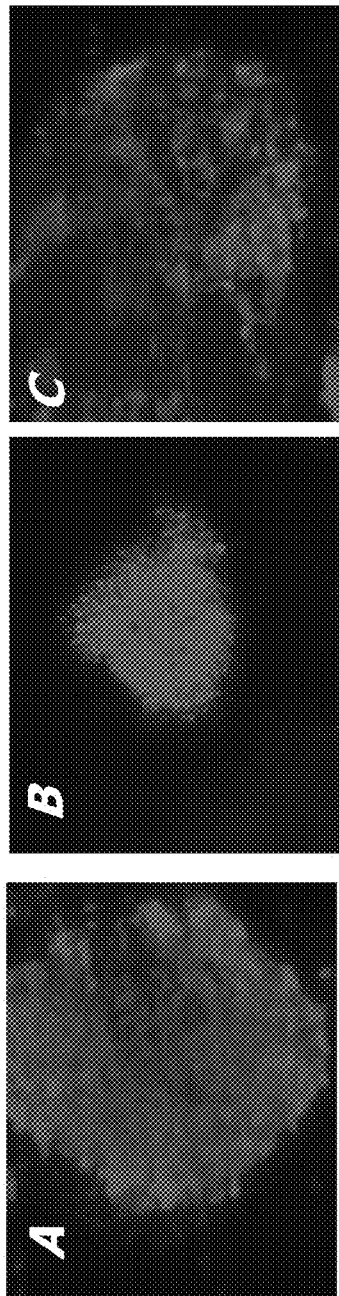

FIGS. 6a-6c are photomicrographs depicting undifferentiated colonies stained with surface markers specific to the hESC undifferentiated stage. I4 hESCs cultured for 36 passages on a Matrigel™ matrix with the medium D1 and stained with TRA-1-60 (FIG. 6a), SSEA4 (FIG. 6b) and TRA-1-81 (FIG. 6c); Magnifications are ×20 for FIGS. 6a-6c.

Figure 7B:
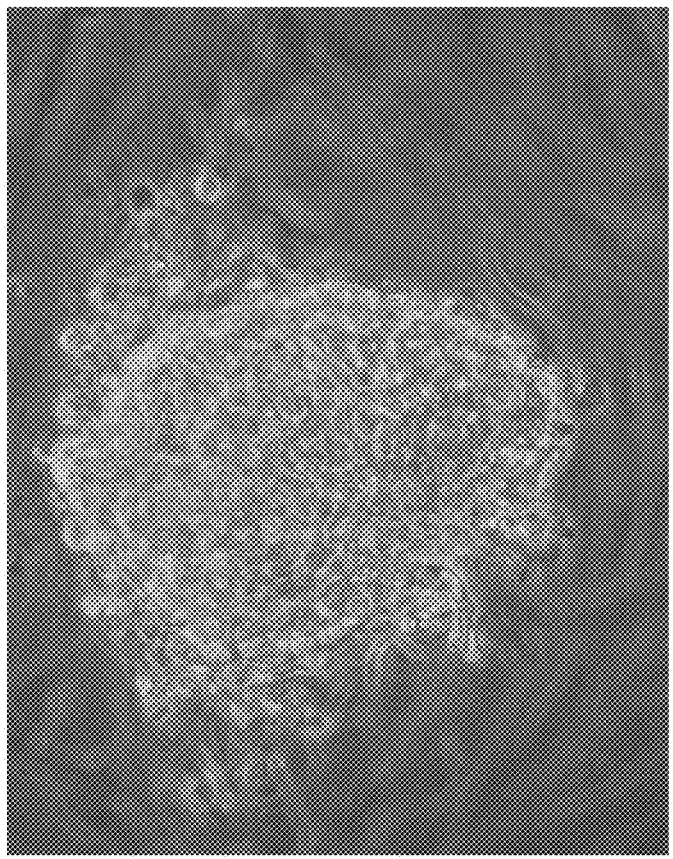
Figure 7A:
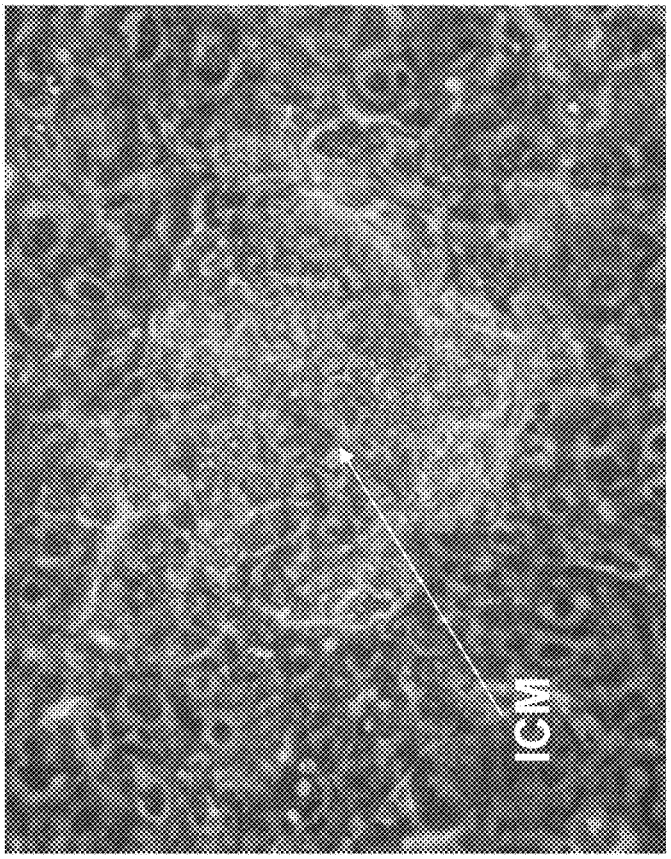

FIGS. 7a-7b are photomicrographs depicting the derivation of a new hESC line under xeno-free conditions on foreskin fibroblasts using the HA16 medium. FIG. 7a—the cultured embryo at first passage (p-1), arrow points at the inner cell mass (ICM); FIG. 7b—the isolated ICM at passage 2 (p-2). Magnifications are ×20 for FIGS. 7a-7b.

Figure 8C:
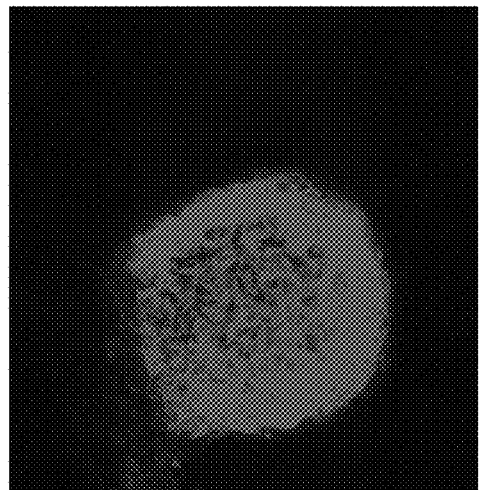
Figure 8B:
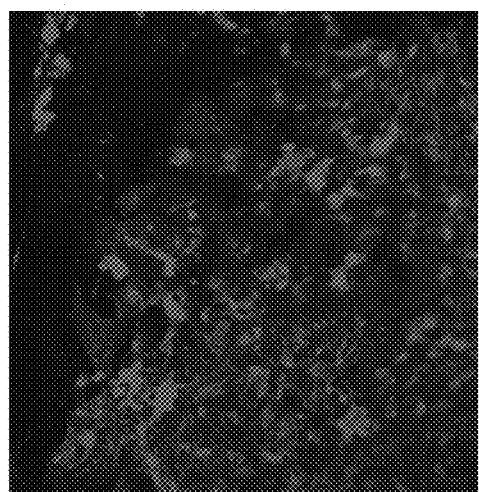
Figure 8A:
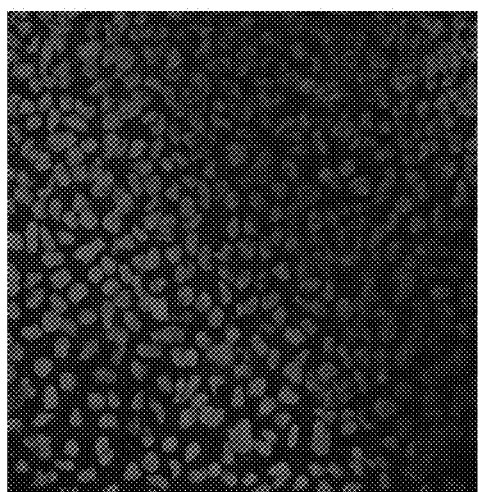

FIGS. 8a-8c are photomicrograph depicting immunostaining of hESCs cultured for 3 passages in suspension in the presence of the D2 medium. Shown are immunostaining analyses of Oct4 (FIG. 8a), TRA-1-60 (FIG. 8b) and TRA-1-81 (FIG. 8c); Magnifications are ×63 for FIGS. 8a-8c.

Figure 9A:
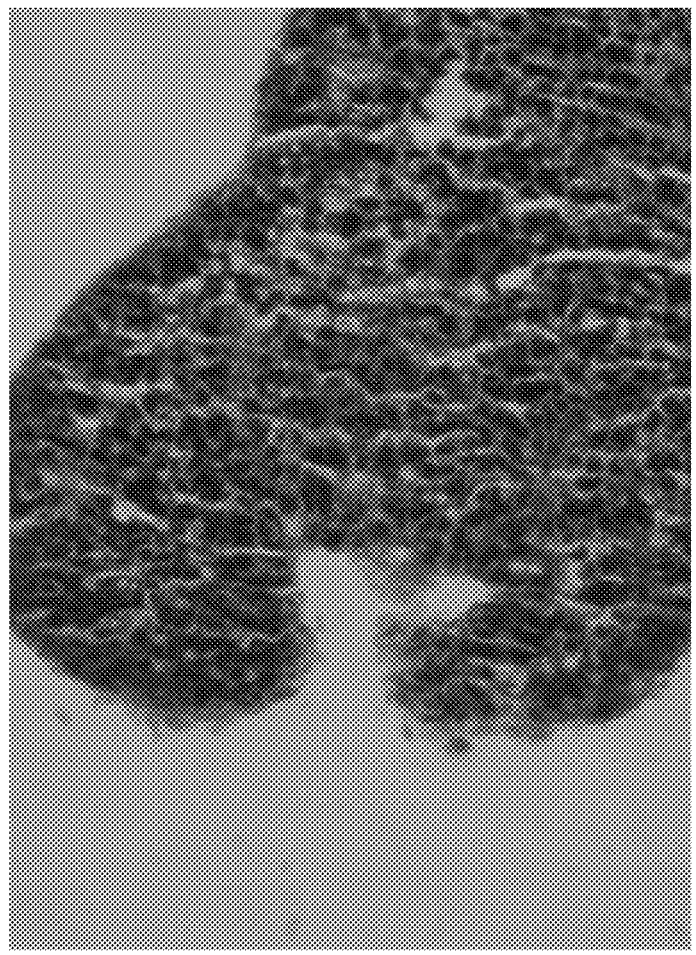
Figure 9C:
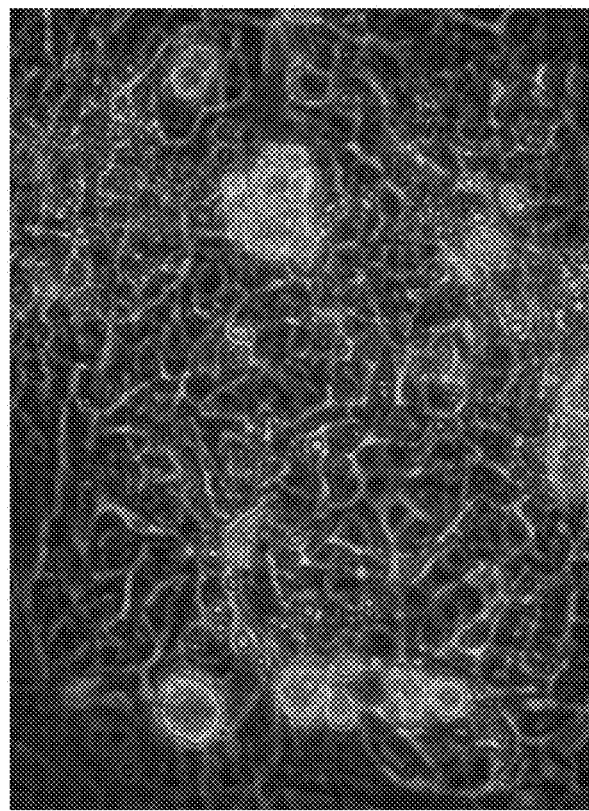
Figure 9B:
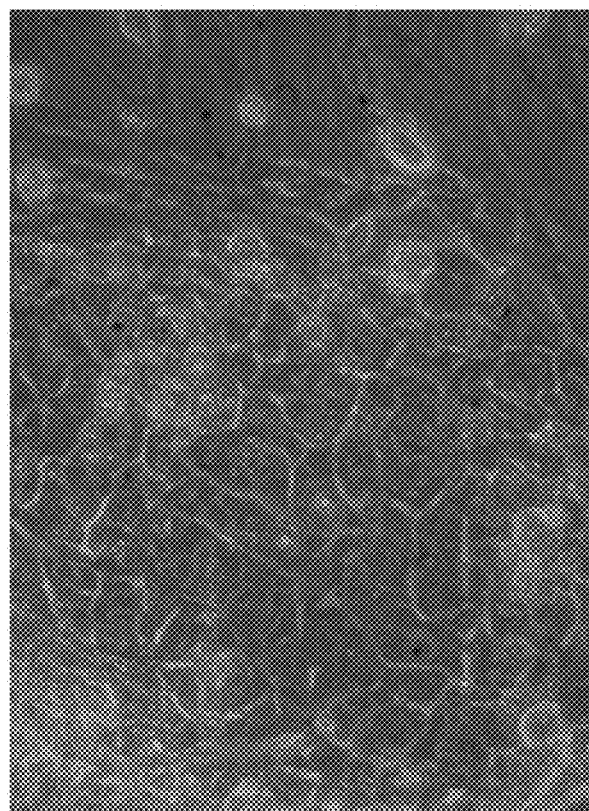
Figure 9D:
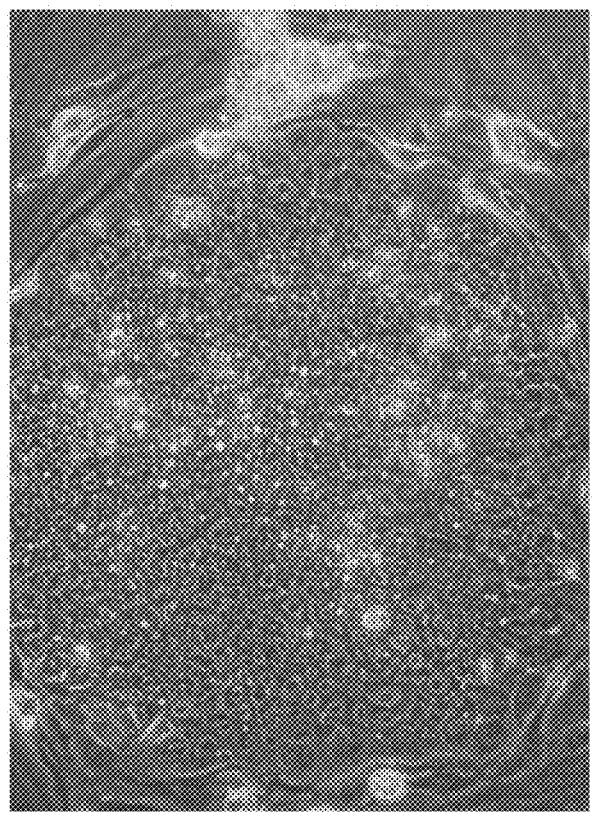
Figure 9E:
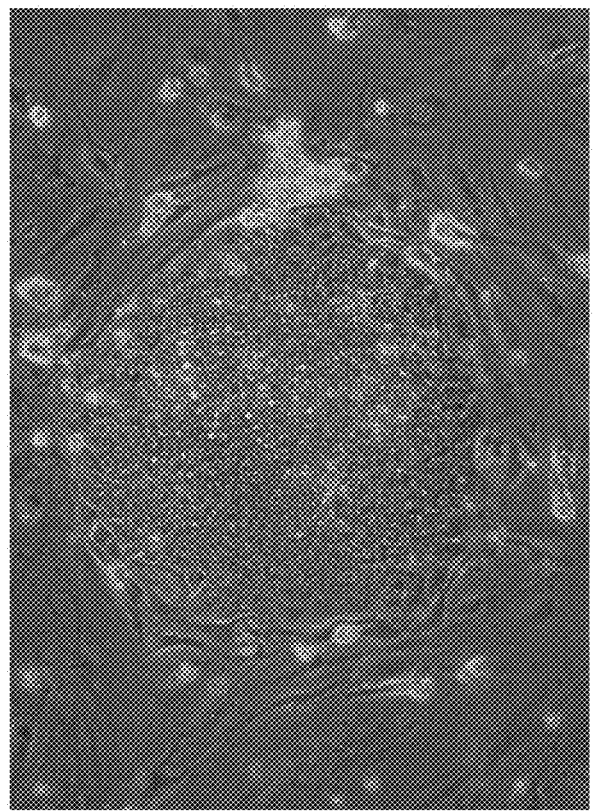
Figure 9G:
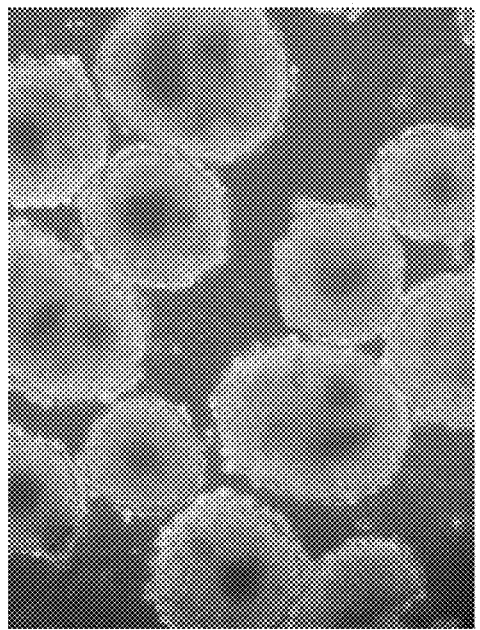
Figure 9F:
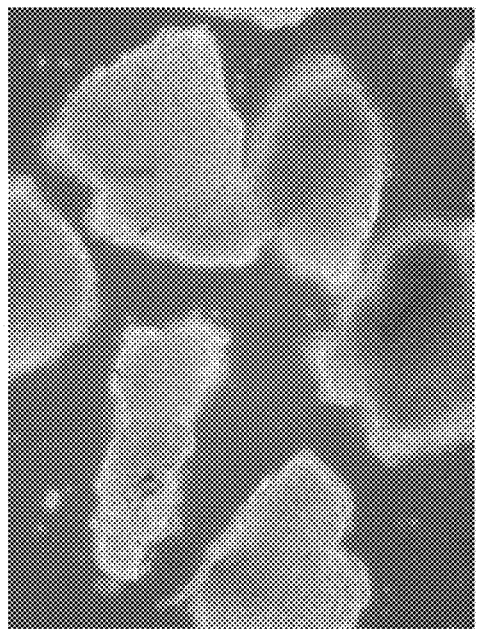

FIGS. 9a-9g are photomicrographs depicting histological sections and morphology of suspended hESCs culture. FIG. 9a—Histology of a hESC clump (I4 hESC line) cultured for 3 passages in suspension in the presence of the D1 medium and stained with H&E. Note that the hESC clump is homogeneous, containing small cells with large nuclei typical for hESCs morphology. FIGS. 9b-9c—I4 hESCs were cultured for 3 passages in suspension in the presence of the D2 medium and were then re-cultured on MEFs. Shown is the morphology of the colonies after re-culturing on MEFs using an inverted microscope. Note the typical undifferentiated morphology of the hESCs. FIGS. 9d-9e—I4 hESCs were cultured for 16 passages in suspension in the presence of the CM100F medium and were then re-cultured on MEFs. Shown is the morphology of colonies after re-culturing on MEFs. Note the typical undifferentiated morphology of the hESCs. FIGS. 9f-9g—I4 hESCs were cultured for 7 passages in suspension in the presence of the HA19 medium (FIG. 9f) or for 10 passages in the presence of the CM100F medium (FIG. 9g); Magnifications are ×20 for FIG. 9a and ×15 for FIGS. 9b-9g, and FIGS. 10a-10d are RT-PCR analyses depicting the expression of representative genes of the undifferentiated state of hESCs cultured in suspension in the presence of the HACM100, CM100F or the HA19 medium. Lane 1—I-4 hESCs cultured for 1 passage in suspension in the presence of the HACM100 medium (serum or serum replacement-free, IL6RIL6-containing medium). Lane 2—I-4 hESCs cultured for 1 passage in suspension in the presence of the CM100F medium (IL6RIL6 and serum replacement-containing medium). Lane 3—I-4 hESCs cultured for 7 passages in suspension in the presence of the HA19 medium (serum or serum replacement-free, protein carrier-free, TGFβ$_3$-containing medium). Lane 4—I-4 hESCs cultured for 2 passages in suspension in the presence of the HA19 medium and then re-cultured on MEFs for additional 6 passages. FIG. 10a—Oct4; FIG. 10b—Rex1; FIG. 10c—Sox2; FIG. 10d—Nanog; RT mix were tested and found negative for all tested genes. All samples were tested for β-actin and were found evenly positive.

DESCRIPTION OF THE PREFERRED EMBODIMENTS

The present invention is of well-defined, xeno-free culture media which comprise a TGFβ isoform or the IL6RIL6 chimera, which are capable of maintaining stem cells in an undifferentiated state. In addition, the present invention is of cell cultures comprising the culture media and the stem cells and of methods of expanding and deriving embryonic stem cells in such well-defined, xeno-free culture media. Moreover, the present invention is of methods of differentiating ESCs or EBs formed therefrom for the generation of lineage specific cells. Specifically, the present invention can be used to generate highly reproducible, xeno-free cultures of hESCs which can be used for both cell-based therapy, pharmaceutical screening, identification of drug targets and cell-based compound delivery.

The principles and operation of the culture medium, cell culture and methods according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Human embryonic stem cells (hESCs) are proliferative, undifferentiated, stem cells capable of differentiating into cells of all three embryonic germ layers. As such, hESCs are employed as a research model for early human development and hold promise for various applications including cell-based therapy, pharmaceutical screening, identification of drug targets and cell-based compound delivery which require almost indefinite amounts of proliferating, yet pluripotent hESCs. For use in human therapy and for the production of large amounts of hESCs, hESCs need to be cultured in complete animal-free (xeno-free), well-defined culture systems, where exposure to animal (e.g., retroviruses) or human pathogens and batch-dependent variations are avoided.

Attempts to achieve defined and/or xeno-free hESCs culture systems include the development of a culture system which is based on a fibronectin matrix and a medium supplemented with 20% SR, transforming growth factor $\beta_1$ (TGF$\beta_1$) and bFGF [Amit et al, 2004] or the culture system based on a matrix consisted of the combination of human collagen IV, fibronectin, laminin and vitronectin and a medium supplemented with human serum albumin, bFGF and TGF$\beta_1$ (Ludwig et al, 2006). However, a major drawback of the latter culture system is the chromosomal instability of the cells associated with extended periods in culture. Thus, improvements of the feeder-free, xeno-free culturing systems of hESCs are highly desirable.

One attractive approach of achieving a defined, xeno-free culture system is using a culture medium which is based on isolated, recombinant factors. For example, mouse ESCs can be continuously cultured without feeder layers provided that leukemia inhibitory factor (LIF) is added to the culture medium. However, accumulating data regarding hESCs suggest that LIF has no effect on preventing hESC differentiation [Thomson et al, 1998; Reubinof et al, 2000]. A recombinant polypeptide, which includes the IL-6 and the soluble IL-6 receptor (the IL6RIL6 chimera, Chebath J, et al., 1997), was shown to support mouse ESC culturing and derivation (Nichols et al., 1994). However, a complex of the soluble hIL-6R and hIL-("hyper IL6") failed to maintain human ESCs in the undifferentiated state when provided with a DMEM/serum replacement (DSR)/FGF2 medium on a laminin matrix (Humphrey et al, 2004). Thus, the common knowledge is that in contrast to mouse ESCs which can be maintained in the undifferentiated state in the presence of activators of the gp130 receptor, culturing of human ESCs in the presence of LIF, IL6 or the "hyper IL6" results in differentiation of the hESCs.

While reducing the present invention to practice, the present inventors have uncovered through laborious experimentations, a well-defined, xeno-free, serum or serum replacement-free and protein carrier-free culture medium which comprises a TGF$\beta$ isoform and which can be used for maintaining hESCs in a pluripotent and undifferentiated state. As is shown in FIGS. 5a-5d and 6a-6c and is described in Example 2 of the Examples section which follows, hESCs cultured on a human fibronectin matrix in the presence of a well-defined TGF$\beta$-containing culture medium which is devoid of serum, serum replacement and a protein carrier (e.g., albumin) exhibited the morphology of undifferentiated ESC colonies and ESC single cells (FIGS. 5a-5d) and expressed typical hESC surface markers specific to the undifferentiated state (FIGS. 6a-6c). In addition, the present inventors have uncovered that the new TGF$\beta$-containing culture medium is suitable for the successful derivation of new hESC lines (FIGS. 7a-7b, Example 3 of the Examples section which follows) on a complete xeno-free culture system.

Thus, according to one aspect of the present invention, there is provided a culture medium. The culture medium comprises a TGF$\beta$ isoform and being devoid of serum, serum replacement and protein carrier, wherein the culture medium is capable of maintaining stem cells in an undifferentiated state.

As used herein the phrase "culture medium" refers to a solid or a liquid substance used to support the growth of stem cells and maintain them in an undifferentiated state. Preferably, the phrase "culture medium" as used herein refers to a liquid substance capable of maintaining the stem cells in an undifferentiated state. The culture medium used by the present invention can be a water-based medium which includes a combination of substances such as salts, nutrients, minerals, vitamins, amino acids, nucleic acids, proteins such as cytokines, growth factors and hormones, all of which are needed for cell proliferation and are capable of maintaining the stem cells in an undifferentiated state. For example, a culture medium according to this aspect of the present invention can be a synthetic tissue culture medium such as Ko-DMEM (Gibco-Invitrogen Corporation products, Grand Island, NY, USA), DMEM/F12 (Biological Industries, Biet Haemek, Israel), Mab ADCB medium (HyClone, Utah, USA) or DMEM/F12 (Biological Industries, Biet Haemek, Israel) supplemented with the necessary additives as is further described hereinunder. Preferably, all ingredients included in the culture medium of the present invention are substantially pure, with a tissue culture grade.

As used herein the phrase "stem cells" refers to cells which are capable of differentiating into other cell types or remaining in an undifferentiated state. Preferably, the phrase "stem cells" encompasses embryonic stem cells (ESCs), adult stem cells and hematopoietic stem cells.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation (i.e., a pre-implantation blastocyst), extended blastocyst cells (EBCs) which are obtained from a post-implantation/pre-gastrulation stage blastocyst (see WO2006/040763 to the present inventors] and embryonic germ (EG) cells which are obtained from the genital tissue of a fetus any time during gestation, preferably before 10 weeks of gestation. Adult stem cells (also called "tissue stem cells") include stem cells derived from any adult or fetal tissue such as adipose tissue, skin, kidney, liver, prostate, pancreas, intestine and bone marrow. Hematopoietic stem cells, which may also referred to as adult tissue stem cells, include stem cells obtained from blood or bone marrow tissue of an individual at any age or from cord blood of a newborn individual. Preferred stem cells according to this aspect of the present invention are embryonic stem cells, preferably of a human or primate (e.g., monkey) origin.

The embryonic stem cells of the present invention can be obtained using well-known cell-culture methods. For example, human embryonic stem cells can be isolated from human blastocysts. Human blastocysts are typically obtained from human in vivo preimplantation embryos or from in vitro fertilized (IVF) embryos.

Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used with this aspect of the present invention. Human ES cells can be purchased from the NIH human embryonic stem cells registry (http://escr(dot)nih(dot)gov). Non-limiting examples of commercially available embryonic stem cell lines are BG01, BG02, BG03, BG04, CY12, CY30, CY92, CY10, TE03 and TE32.

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, MO, USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Adult tissue stem cells can be isolated using various methods known in the art such as those disclosed by Alison, M. R. [J Pathol. 2003 200(5): 547-50], Cal, J. et al., [Blood Cells Mol Dis. 2003 31(1): 18-27], Collins, A. T. et al., [J Cell Sci. 2001; 114(Pt 21): 3865-72], Potten, C. S. and Morris, R. J. [Epithelial stem cells in vivo. 1988. J. Cell Sci. Suppl. 10, 45-62], Dominici, M et al., [J. Biol. Regul. Homeost. Agents. 2001, 15: 28-37], Caplan and Haynesworth [U.S. Pat. No. 5,486,359] Jones E. A. et al., [Arthritis Rheum. 2002, 46(12): 3349-60]. Fetal stem cells can be isolated using various methods known in the art such as those disclosed by Eventov-Friedman S, et al., PLoS Med. 2006, 3: e215; Eventov-Friedman S, et al., Proc Natl Acad Sci USA. 2005, 102: 2928-33; Dekel B, et al., 2003, Nat Med. 9: 53-60; and Dekel B, et al., 2002, J. Am. Soc. Nephrol. 13: 977-90. Hematopoietic stem cells can be isolated using various methods known in the arts such as those disclosed by "Handbook of Stem Cells" edit by Robert Lanze, Elsevier Academic Press, 2004, Chapter 54, pp609-614, isolation and characterization of hematopoietic stem cells, by Gerald J Spangrude and William B Stayton.

It will be appreciated that stem cells in an undifferentiated state are of a distinct morphology, which is clearly distinguishable by the skilled in the art from that of differentiated cells of embryo or adult origin. Typically, undifferentiated stem cells have high nuclear/cytoplasmic ratios, prominent nucleoli and compact colony formation with poorly discernable cell junctions. Additional features of the undifferentiated state of the stem cells are further described hereinunder.

The culture medium according to this aspect of the present invention comprises a TGFβ isoform and being devoid of serum, serum replacement and protein carrier.

As used herein the phrase "TGFβ isoform" refers to any isoform of the transforming growth factor beta (β) including TGFβ$_1$ (e.g., *Homo sapiens* TGFβ$_1$, GenBank Accession No. NP_000651), TGFβ$_2$ (e.g., *Homo sapiens* TGFβ$_2$, GenBank Accession No. NP_003229) and TGFβ$_3$ (e.g., *Homo sapiens* TGFβ$_3$, GenBank Accession No. NP_003230) which function through the same receptor signaling system in the control of proliferation, differentiation, and other functions in many cell types. TGFβ$_3$ acts in inducing transformation and also acts as a negative autocrine growth factor. According to preferred embodiments of the present invention the TGFβ isoform which is included in the culture medium of the present invention is TGFβ$_1$ or TGFβ$_3$. Such TGFβ isoforms can be obtained from various commercial sources such as R&D Systems Minneapolis MN, USA.

As is shown in Example 2 of the Examples section which follows, the present inventors have used various culture media which contain TGFβ$_1$ (e.g., the D1 medium which contains 0.12 ng/ml TGFβ$_1$) or TGFβ$_3$ (e.g., the D2 medium, the HA16 medium or the HA19 medium which contain 2 ng/ml TGFβ$_3$) to successfully culture hESCs and maintain them in the undifferentiated state.

Preferably, TGFβ$_1$ which is included in the culture medium of this aspect of the present invention is provided at a concentration of at least 0.06 ng/ml, more preferably, at least 0.07 ng/ml, more preferably, at least 0.08 ng/ml, more preferably, at least 0.09 ng/ml, more preferably, at least 0.1 ng/ml, more preferably, at least 0.11 ng/ml, even more preferably, at least 0.12 ng/ml.

Preferably, TGFβ$_3$ which is included in the culture medium of this aspect of the present invention is provided at a concentration of at least 0.5 ng/ml, more preferably, at least 0.6 ng/ml, more preferably, at least 0.8 ng/ml, more preferably, at least 0.9 ng/ml, more preferably, at least 1 ng/ml, more preferably, at least 1.2 ng/ml, more preferably, at least 1.4 ng/ml, more preferably, at least 1.6 ng/ml, more preferably, at least 1.8 ng/ml, even more preferably, at least 2 ng/ml.

Preferably, the TGFβ-containing culture medium of this aspect of the present invention further includes other growth factors such as basic fibroblast growth factor (bFGF). bFGF can be obtained from any commercial supplier of tissue culture ingredients such as Invitrogen Corporation products, Grand Island NY, USA.

As is shown in Example 2 of the Examples section which follows, a DMEM/F12—based culture medium (e.g., HA16 or HA19 medium which includes TGFβ$_3$ and 4 ng/ml bFGF) or Mab ADCB medium-based culture medium (e.g., D1 or D2 medium which includes TGFβ$_1$ or TGFβ$_3$, respectively, and 10 ng/ml bFGF) were capable of maintaining hESCs in the undifferentiated state in culture. It should be mentioned that a Mab ADCB medium-based culture medium which includes a TGFβ$_1$ or TGFβ$_3$ isoform and bFGF at a concentration of 8 ng/ml was also capable of maintaining hESCs in the undifferentiated state for at least 5 passages (data not shown).

Preferably, the bFGF which is included in TGFβ-containing culture medium of this aspect of the present invention is provided at a concentration of at least 2 ng/ml, at least 3 ng, at least 4 ng/ml, at least 5 ng/ml, at least 6 ng/ml, at least 7 ng, at least 8 ng/ml, at least 9 ng/ml, at least 10 ng/ml.

As mentioned, the culture medium of this aspect of the present invention is devoid of a protein carrier (i.e., protein carrier-free). A protein carrier refers to a protein which acts in the transfer of proteins or nutrients (e.g., minerals such as zinc) to the cells in the culture. Such protein carriers can be, for example, albumin (e.g., bovine serum albumin), Albumax (lipid enriched albumin) or plasmanate (human plasma isolated proteins). Since these carriers are derived from either human or animal sources their use in hESCs cultures is limited by batch-specific variations and/or exposure to pathogens. On the other hand, the recombinant human albumin, which is substantially pure and devoid of animal contaminants is highly expensive, thus not commonly used in hESCs cultures. Thus, a culture medium which is devoid of a protein carrier is highly advantageous since it enables a truly defined medium that can be manufacture from recombinant or synthetic materials.

In addition, as mentioned hereinabove, the culture medium of this aspect of the present invention is also devoid of serum (i.e., serum-free) or serum replacement (i.e., serum replacement-free). It should be noted that serum or serum replacement are added to most culture media which are designed for culturing stem cells, and particularly, embryonic stem cells, in order to provide the cells with the optimal environment, similar to that present in vivo (i.e., within the organism from which the cells are derived, e.g., a blastocyst of an embryo or an adult tissue of a postnatal individual). However, while the use of serum which is derived from either an animal source (e.g., bovine serum) or a human source (human serum) is limited by the significant variations in serum components between individuals and the risk of having xeno contaminants (in case of an animal serum is used), the use of the more defined composition such as the currently available Serum Replacement™ (Gibco-Invitrogen Corporation, Grand Island, NY USA) may be limited by the presence of Albumax (Bovine serum albumin enriched with lipids) which is from an animal source within the composition (International Patent Publication No. WO 98/30679 to Price, P. J. et al).

Thus, a culture medium which comprises a TGFβ isoform as described hereinabove and is devoid of serum, serum replacement and a protein carrier is highly desirable for both cell-based therapy and pharmaceutical industry, e.g., for pharmaceutical screening, identification of drug targets and cell-based compound delivery.

Preferably, the culture medium of this aspect of the present invention is capable of expanding the stem cells while maintaining them in the undifferentiated state. As used herein the term "expanding" refers to obtaining a plurality of cells from a single or a population of stem cells. Preferably, expanding embryonic stem cells refers also to increasing the number of embryonic stem cells over the culturing period. It will be appreciated that the number of stem cells which can be obtained from a single stem cell depends on the proliferation capacity of the stem cell. The proliferation capacity of a stem cell can be calculated by the doubling time of the cell (i.e., the time needed for a cell to undergo a mitotic division in the culture) and the period the stem cell culture can be maintained in the undifferentiated state (which is equivalent to the number of passages multiplied by the days between each passage).

For example, as described in Example 2 of the Examples section which follows, hESCs could be maintained in the undifferentiated state in the presence of the D1 TGFβ-containing culture medium for at least 53 passages. Given that each passage occurs every 4-7 days, the hESCs were maintained for 265 days (i.e., 6360 hours). Given that the hESCs doubling time was 36 hours, a single hESC cultured under these conditions could be expanded to give rise to $2^{176}$ (i.e., $9.57 \times 10^{52}$) hESCs.

Preferably the stem cells which are maintained and expanded in the culture medium of the present invention exhibit stable karyotype (chromosomal stability) while in culture. For example, hESCs cultured in the presence of an IL6RIL6-containing medium (e.g., CM100) or a TGFβ-containing medium (e.g., D1, D2 or HA16) exhibited normal karyotype following at least 23 or 15 passages, respectively.

While further reducing the present invention to practice, the present inventors have uncovered that a culture medium which includes the IL6RIL6 chimera is also capable of maintaining human ESCs in the undifferentiated state. This is in sharp contrast to the teachings of Humphrey R., et al., (2004) which failed to maintain hESCs in the undifferentiated state when using the "hyper IL6" complex and thus concluded that maintenance of pluripotency in human ESCs is STAT independent. Thus, Humphrey R., et al., (2004) teaches away the present invention.

As is shown in FIGS. 1a-1f, 2, 3a-3c and 4a-4l and described in Example 1 of the Examples section which follows, a culture system based on a fibronectin or laminin feeder layer-free matrix and a culture medium which includes the IL6RIL6 chimera, serum replacement and bFGF was capable of maintaining hESCs in the undifferentiated state for at least 43 (on a fibronectin matrix) or 7 (on a laminin matrix) passages while preserving all hESCs characteristics and pluripotency. On the other hand, as is further shown in Example 1 of the Examples section which follows, a medium containing serum replacement, bFGF and the unconjugated chimera components, i.e., IL-6 (GenBank Accession No. CAG29292) and soluble IL-6 receptor (GenBank Accession No. AAH89410), failed to support hESC prolonged culture and resulted in differentiation of hESCs within 3-5 passages. In addition, hESCs cultured in a medium containing the IL6RIL6 chimera and serum replacement, in the absence of bFGF, exhibited low proliferation capacity and could not be maintained in culture beyond 1-2 passages. Thus, these results demonstrate, for the first time, that hESCs can be cultured and maintained in the undifferentiated state in a feeder-layer free culture system in the presence of a culture medium which comprises the IL6RIL6 chimera.

Thus, according to another aspect of the present invention there is provided a culture medium which comprises an IL6RIL6 chimera, wherein the culture medium is capable of maintaining human embryonic stem cells in an undifferentiated state.

As used herein the term "IL6RIL6" refers to a chimeric polypeptide which comprises the soluble portion of interleukin-6 receptor (IL-6-R, e.g., the human IL-6-R as set forth by GenBank Accession No. AAH89410) (e.g., a portion of the soluble IL6 receptors as set forth by amino acids 112-355 of GenBank Accession No. AAH89410) and the interleukin-6 (IL6) (e.g., human IL-6 as set forth by GenBank Accession No. CAG29292) or a biologically active fraction thereof (e.g., a receptor binding domain). Preferably, the IL6RIL6 chimera used by the method according to this aspect of the present invention is capable of supporting the undifferentiated growth of human embryonic stem cells, while maintaining their pluripotent capacity. It will be appreciated that when constructing the IL6RIL6 chimera the two functional portions (i.e., the IL6 and its receptor) can be directly fused (e.g., attached or translationally fused, i.e., encoded by a single open reading frame) to each other or conjugated (attached or translationally fused) via a suitable linker (e.g., a polypeptide linker). Preferably, the IL6RIL6 chimeric polypeptide exhibits a similar amount and pattern of glycosylation as the naturally occurring IL6 and IL6 receptor. For example, a suitable IL6RIL6 chimera is as set forth in SEQ ID NO:31 and in FIG. 11 of WO 99/02552 to Revel M., et al., which is fully incorporated herein by reference.

It will be appreciated that any of the proteinaceous factors used in the culture medium of the present invention (e.g., the IL6RIL6 chimera, bFGF, TGFβ$_1$, TGFβ$_3$) can be recombinantly expressed or biochemically synthesized. In addition, naturally occurring proteinaceous factors such as bFGF and TGFβ can be purified from biological samples (e.g., from human serum, cell cultures) using methods well known in the art.

Biochemical synthesis of the proteinaceous factors of the present invention (e.g., the IL6RIL6 chimera) can be performed using standard solid phase techniques. These methods include exclusive solid phase synthesis, partial solid phase synthesis methods, fragment condensation and classical solution synthesis.

Recombinant expression of the proteinaceous factors of the present invention (e.g., the IL6RIL6 chimera) can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463. Specifically, the IL6RIL6 chimera can be generated as described in PCT publication WO 99/02552 to Revel M., et al. and Chebath J, et al., 1997, which are fully incorporated herein by reference.

For example, to generate the IL6RIL6 chimera, a polynucleotide sequence encoding the IL6RIL6 chimera (e.g., the polypeptide set forth by SEQ ID NO:31) is preferably ligated into a nucleic acid construct suitable for expression in a host cell [i.e., a cell in which the polynucleotide encoding the polypeptide-of-choice (e.g., the IL6RIL6 chimera) is expressed]. Preferably, to generate an IL6RIL6 chimera with the amount and pattern of glycosylation as of the naturally occurring IL6 and IL6-R, the host cell employed is a eukaryotic host cell, more preferably a mammalian host cell such as human cell or CHO cell).

For expression in mammalian cells [e.g., CHO cells, human HEK 293 cells (ATCC CRL 1573)] a number of mammalian expression vectors can be used. Examples include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Various methods can be used to introduce the expression vector of the present invention into host cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of the recombinant polypeptide (e.g., the IL6RIL6 chimera). Following a predetermined time in culture, recovery of the recombinant polypeptide is effected. The phrase "recovery of the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

The polypeptide of the present invention (e.g., the IL6RIL6 chimera) is preferably retrieved in "substantially pure" form. As used herein, the phrase "substantially pure" refers to a purity that allows for the effective use of the polypeptide of the present invention (e.g., the IL6RIL6 chimera) in maintaining the human embryonic stem cells in an undifferentiated state while in culture.

As shown in FIGS. 1-4 and described in Example 1 of the Examples section which follows, a medium supplemented with the 100 or 300 ng/ml of the IL6RIL6 chimera enabled the prolonged culturing of hESCs in the undifferentiated state for at least 43 passages, while preserving normal karyotype and pluripotent capacity [as evidenced by the formation of embryoid bodies (EBs) which express markers of all three embryonic germ cells].

Preferably, the IL6RIL6 chimera which is included in the culture medium of this aspect of the present invention is provided at a concentration of at least 25 ng/ml, at least 50 ng/ml, at least 100 ng/ml, preferably, at least 200 ng/ml, preferably, at least 300 ng/ml. It should be noted that the concentration of the IL6RIL6 chimera can vary depending on the purity of the chimeric polypeptide following its synthesis or recombinant expression and those of skills in the art are capable of adjusting the optimal concentration depending on such purity.

Preferably, the IL6RIL6-containing culture medium of this aspect of the present invention includes at least 2 ng/ml bFGF, at least 3 ng/ml, at least 4 ng/ml, at least 5 ng/ml, at least 6 ng/ml, at least 7 ng, at least 8 ng/ml, at least 9 ng/ml, at least 10 ng/ml bFGF. For example, as shown in Example 1 of the Examples section which follows, a culture medium which includes 4 ng/ml bFGF along with 100 ng/ml of the IL6RIL6 chimera was capable of maintaining hESCs in an undifferentiated state for at least 43 passages.

As mentioned, the IL6RIL6-containing culture medium described in Example 1 of the Examples section which follows included serum replacement. It should be noted that such a culture medium can also include serum (e.g., such as human serum) instead of serum replacement and yet maintain hESCs in culture in the undifferentiated state. Thus, serum or serum replacement which are included in the IL6RIL-containing culture medium of this aspect of the present invention can be provided at various concentrations, such as a concentration of at least 10%, e.g., a concentration of at least 15%, at least 20%, at least 25% or at least 30%.

Alternatively and currently more preferred, in order to achieve more defined culture conditions of the hESCs, the IL6RIL6-containing culture medium of this aspect of the present invention is preferably devoid of serum or serum replacement. A non-limiting example of such a culture medium can be the HACM100 culture medium described in Examples 2 and 4 of the Examples section which follows.

Thus, any of the culture media described hereinabove, which are based on the TGFβ isoform or the IL6RIL6 chimera present, for the first time, a well-defined, xeno-free culture medium which is highly suitable for culturing hESCs for applications such as cell-based therapy and for use in the pharmaceutical industry.

Thus, according to yet another aspect of the present invention there is provided a culture medium which is devoid of serum (i.e., serum-free), xeno contaminant (i.e., xeno-free), feeder layers (i.e., feeder layer-free) and protein carrier (i.e., protein carrier-free) and yet capable of maintaining stem cells in an undifferentiated state.

As mentioned hereinabove and described in Examples 1 and 2 of the Examples section which follows, the present inventors have uncovered that stem cells such as human embryonic stem cells can be expanded using any of the culturing media described hereinabove and be maintained in the undifferentiated state while in culture.

Thus, according to an additional aspect of the present invention there is provided a cell culture which comprises the stem cell and any of the culture media described hereinabove, while the culture medium is capable of maintaining said stem cells in an undifferentiated state.

According to still an additional aspect of the present invention there is provided a method of expanding and maintaining stem cells in an undifferentiated state. The method is effected by culturing the stem cells in any of the culture media described hereinabove, thereby expanding and maintaining the stem cells in the undifferentiated state.

Culturing according to this aspect of the present invention is effected by plating the stem cells onto a matrix in a cell density which promotes cell survival and proliferation but limits differentiation. Typically, a plating density of between about 15,000 cells/cm$^2$ and about 3,000,000 cells/cm$^2$ is used.

It will be appreciated that although single-cell suspensions of stem cells are usually seeded, small clusters may also be used. To this end, enzymatic digestion (such as with type IV collagenase) utilized for cluster disruption (see Examples 1 and 2 of the Examples section which follows) is terminated before stem cells become completely dispersed and the cells are triturated with a pipette such that clumps (i.e., 10-200 cells) are formed. However, measures are taken to avoid large clusters which may cause cell differentiation.

As mentioned before, stem cells can be cultured on feeder cells or on feeder-layer free culturing systems using a matrix instead of a feeder cell layer. As used herein, the term "matrix" refers to any substance to which the stem cells can adhere and which therefore can substitute the cell attachment function of feeder cells. Such a matrix typically contains extracellular components to which the stem cells can attach and thus it provides a suitable culture substrate.

Particularly suitable for use with the present invention are extracellular matrix components derived from basement membrane or extracellular matrix components that form part of adhesion molecule receptor-ligand couplings. Non-limiting examples of suitable matrices which can be used by the method of this aspect of the present invention include Matrigel® (Becton Dickinson, USA), laminin, fibronectin, proteoglycan, entactin, heparan sulfate, and the like, alone or in various combinations. In cases where complete animal-free culturing conditions are desired, the matrix is preferably derived from a human source or synthesized using recombinant techniques. Such matrices include, for example, human-derived fibronectin, recombinant fibronectin, human-derived laminin, foreskin fibroblast matrix or a synthetic fibronectin matrix which can be obtained from Sigma, St. Louis, MO, USA or can be produced using known recombinant DNA technology. Preferred matrices of the present invention are fibronectin derived matrices.

Thus, stem cells cultured using the teachings of the present invention can be expanded while maintaining in the undifferentiated state. For example, as described in Example 2 of the Examples section which follows, culturing of hESCs on a Matrigel™ in the presence of the TGFβ-containing culture medium (the D1 medium) for at least 53 passages (8-9 months) resulted in an expansion factor of $2^{180}$ (i.e., $1.5 \times 10^{54}$) given that the hESC doubling time is 36 hours and that passaging occurs every 4-6 days.

Alternatively, as is shown in FIGS. 8a-8c, 9a-9g and 10a-10d and is described in Example 4 of the Examples section which follows and in U.S. provisional application No. 60/834,795 to the present inventors (filed Aug. 2, 2006), the present inventors have uncovered that human ESCs can be expanded in a suspension culture devoid of substrate adherence and as such can be maintained in the undifferentiated, pluripotent state.

As used herein the phrase "suspension culture" refers to a culture in which the embryonic stem cells are suspended in a medium rather than adhering to a surface.

Thus, the culture of the present invention is "devoid of substrate adherence" in which the stem cells (e.g., ESCs) are capable of expanding without adherence to an external substrate such as components of extracellular matrix, a glass microcarrier or beads.

Thus, hESCs cultured in a suspension culture devoid of substrate adherence can be expanded for at least 17 passages in the CM100F medium and maintain their undifferentiated, pluripotent state (Example 4 and data not shown).

When cultured according to the teachings of the present invention, stem cell growth is monitored to determine their differentiation state. The differentiation state can be determined using various approaches including, for example, morphological evaluation (e.g., as shown in FIGS. 1a-1f, 5a-5d and 9a-9g) and/or detection of the expression pattern of typical markers of the undifferentiated state using immunological techniques such as flow cytometry for membrane-bound markers, immunohistochemistry or immunofluorescence for extracellular and intracellular markers and enzymatic immunoassay, for secreted molecular markers. For example, immunofluorescence employed on hESCs cultured according to the method of this aspect of the present invention revealed the expression of Oct4, stage-specific embryonic antigen (SSEA) 4, the tumour-rejecting antigen (TRA)-1-60 and TRA-1-81 (FIGS. 3a-3c, 6a-6c and 8a-8c). Additionally, the level of transcripts of specific undifferentiation markers (e.g., Oct 4, Nanog, Sox2, Rex1, Cx43, FGF4) or differentiation markers (e.g., albumin, glucagons, α-cardiac actin, β-globulin, Flk1, AC133 and neurofilament) can be detected using RNA-based techniques such as RT-PCR analysis (as shown in FIGS. 4a-4l and 10a-10d) and/or cDNA microarray analysis.

Determination of ES cell differentiation can also be effected via measurements of alkaline phosphatase activity. Undifferentiated human ES cells have alkaline phosphatase activity which can be detected by fixing the cells with 4% paraformaldehyde and developing with the Vector Red substrate kit according to manufacturer's instructions (Vector Laboratories, Burlingame, California, USA).

As is further shown in FIGS. 7a-7b and described in Example 3 of the Examples section which follows, the present inventors were capable of deriving a new line of human ESCs in complete xeno-free culturing conditions using the TGFβ-based culture medium.

Thus, according to yet an additional aspect of the present invention there is provided a method of deriving an embryonic stem cell line. The method is effected by: (a) obtaining an embryonic stem cell from a pre-implantation stage blastocyst, post-implantation stage blastocyst and/or a genital tissue of a fetus; and (b) culturing the embryonic stem cell in any of the culture media described hereinabove, thereby deriving the embryonic stem cell line.

The term "deriving" as used herein refers to generating an embryonic stem cell line from at least one embryonic stem cell.

As used herein the phrase "embryonic stem cell line" refers to embryonic stem cells which are derived from a single or a group of embryonic stem cells of a single organism (e.g., a single human blastocyst), and which are characterized by the ability to proliferate in culture while maintaining the undifferentiated state and the pluripotent capacity.

Obtaining an embryonic stem cell from a pre-implantation stage blastocyst, post-implantation stage blastocyst and/or a genital tissue of a fetus can be performed using methods known in the art, as described hereinabove and in the "General Materials and Experimental Methods" of the Examples section which follows. Briefly, the zona pellucida is removed from a 5-7 day-old blastocyst using Tyrode's acidic solution (Sigma, St Louis MO, USA), the trophoblast layer is specifically removed either by immunosurgery or mechanically using 27 g needles and the exposed ICM is either directly cultured in a suitable culture system (e.g., feeder layers, feeder-free matrix or a suspension culture) in the presence of any of the culture media described hereinabove (e.g., the CM100F, HA16 or D2 medium) for 4-10 days (in case a preimplantation blastocyst is used) or subject to in vitro implantation by culturing the ICM for 6-8 days (to obtain cells of a 13 day-old blastocyst in case a post-implantation/pre-gastrulation blastocyst is used) on feeder layers or a feeder-free culturing system which allow implantation of the blastocyst to the surface, following which the implanted cells are isolated and can be further cultured on feeder layers, feeder-free matrix or a suspension culture in the presence of any of the culture media described hereinabove (e.g., the CM100F, HA16 or D2 medium) as described hereinunder. When using the genital tissue of a fetus, the genital ridges are dissociated and cut into small chunks which are thereafter disaggregated into cells by mechanical dissociation. The single cell EG cells are then cultured in any of the culture media described hereinabove for 4-10 days).

Once obtained the ESCs are further cultured in any of the culture media described hereinabove which allow expansion of the embryonic stem cells in the undifferentiated state, essentially as described hereinabove.

Preferably, the cell culture of the present invention is characterized by at least 40%, at least 50%, at least 60%, more preferably at least 70%, more preferably at least 80%, most preferably at least 85% of undifferentiated stem cells.

It will be appreciated that an established embryonic stem cell line can be subject to freeze/thaw cycles without hampering the proliferative capacity of the cells in the undifferentiated state while preserving their pluripotent capacity. For example, as is shown in the Examples section which follows, using 15% SR and 10% DMSO, hESCs were successfully frozen and thawed.

As is shown in FIGS. 4a-4l and is described in Examples 1, 2 and 4 of the Examples section which follows, hESCs which were expanded and maintained in any of the culture media described hereinabove are pluripotent (i.e., capable of differentiating into all cell types of the three embryonic germ layers, the ectoderm, the endoderm and the mesoderm) as evidenced in vitro (by the formation of EBs) and in vivo (by the formation of teratomas). Thus, hESCs cultured according to the teachings of the present invention can be used as a source for generating differentiated, lineage-specific cells. Such cells can be obtained directly from the ESCs by subjecting the ESCs to various differentiation signals (e.g., cytokines, hormones, growth factors) or indirectly, via the formation of embryoid bodies and the subsequent differentiation of cells of the EBs to lineage-specific cells.

Thus, according to yet an additional aspect of the present invention there is provided a method of generating embryoid bodies from embryonic stem cells. The method is effected by (a) culturing the embryonic stem cells in any of the culture media described hereinabove which is capable of maintaining the embryonic stem cells in an undifferentiated state, to thereby obtain expanded, undifferentiated embryonic stem cells; and (b) subjecting the expanded, undifferentiated embryonic stem cells to culturing conditions suitable for differentiating the embryonic stem cells to embryoid bodies; thereby generating the embryoid bodies from the embryonic stem cells.

As used herein the phrase "embryoid bodies" refers to morphological structures comprised of a population of ESCs, extended blastocyst cells (EBCs) and/or embryonic germ cells (EGCs) which have undergone differentiation. EBs formation initiates following the removal of differentiation blocking factors from ES cell cultures. In the first step of EBs formation, ESCs proliferate into small masses of cells which then proceed with differentiation. In the first phase of differentiation, following 1-4 days in culture for human ESCs, a layer of endodermal cells is formed on the outer layer of the small mass, resulting in "simple EBs". In the second phase, following 3-20 days post-differentiation, "complex EBs" are formed. Complex EBs are characterized by extensive differentiation of ectodermal and mesodermal cells and derivative tissues.

Thus, the method of this aspect of the present invention involves the culturing of ESCs in any of the culture media described hereinabove in order to obtain expanded, undifferentiated embryonic stem cells and then subjecting the expanded, undifferentiated ESCs to culturing conditions suitable for differentiating the ESCs to embryoid bodies. Such culturing conditions are substantially devoid of differentiation inhibitory factors which were employed during step (a), e.g., a TGFβ isoform or the IL6RIL6 chimera.

For EBs formation, the ESCs are removed from their feeder cell layers, feeder-free-culturing systems (e.g., the fibronectin or laminin matrix) or suspension cultures and are transferred to a suspension culture in the presence of a culture medium containing serum or serum replacement and being devoid of differentiation-inhibitory factors, essentially as described in Examples 1, 2 and 4 of the Examples section which follows. For example, a culture medium suitable for EBs formation may include a basic culture medium (e.g., Ko-DMEM or DMEM/F12) supplemented with 20% FBSd (HyClone, Utah, USA), 1 mM L-glutamine, 0.1 mM β-mercaptoethanol, and 1% non-essential amino acid stock.

Monitoring the formation of EBs can be effected by morphological evaluations (e.g., histological staining), determination of expression of differentiation-specific markers [e.g., using immunological techniques or RNA-based analysis (e.g., RT-PCR, cDNA microarray) as shown in FIGS. 4a-4l], essentially as described in the Examples section which follows.

Thus, as is shown in FIGS. 4f-4l, cells harvested from EBs according to the method of this aspect of the present invention exhibited markers of all three embryonic germ layers, such as albumin and glucagon (typical of the embryonic endoderm), α-cardiac actin, β-globulin and Flk1 (typical of the embryonic mesoderm), and AC133 and neurofilament (NFH) (typical of the embryonic ectoderm).

It will be appreciated that in order to obtain lineage-specific cells from the EBs, cells of the EBs can be further subjected to culturing conditions suitable for lineage-specific cells.

Preferably, the method of this aspect of the present invention further includes step (c) of subjecting cells of the embryoid bodies to culturing conditions suitable for differentiating and/or expanding lineage specific cells; thereby generating the lineage-specific cells from the embryonic stem cells.

As used herein the phrase "culturing conditions suitable for differentiating and/or expanding lineage specific cells" refers to a combination of culture system, e.g., feeder cell layers, feeder-free matrix or a suspension culture and a culture medium which are suitable for the differentiation and/or expansion of specific cell lineages derived from cells of the EBs. Non-limiting examples of such culturing conditions are further described hereinunder.

Preferably, the method of this aspect of the present invention further includes isolating lineage specific cells following step (b).

As used herein, the phrase "isolating lineage specific cells" refers to the enrichment of a mixed population of cells in a culture with cells predominantly displaying at least one characteristic associated with a specific lineage phenotype. It will be appreciated that all cell lineages are derived from the three embryonic germ layers. Thus, for example, hepatocytes and pancreatic cells are derived from the embryonic endoderm, osseous, cartilaginous, elastic, fibrous connective tissues, myocytes, myocardial cells, bone marrow cells, vascular cells (namely endothelial and smooth muscle cells), and hematopoietic cells are differentiated from embryonic mesoderm and neural, retina and epidermal cells are derived from the embryonic ectoderm.

According to one preferred embodiment of the present invention, isolating is effected by sorting of cells of the EBs via fluorescence activated cell sorter (FACS).

Methods of isolating EB-derived-differentiated cells via FACS analysis are known in the art. According to one method, EBs are disaggregated using a solution of Trypsin and EDTA (0.025% and 0.01%, respectively), washed with 5% fetal bovine serum (FBS) in phosphate buffered saline (PBS) and incubated for 30 min on ice with fluorescently-labeled antibodies directed against cell surface antigens characteristics to a specific cell lineage. For example, endothelial cells are isolated by attaching an antibody directed against the platelet endothelial cell adhesion molecule-1 (PECAM1) such as the fluorescently-labeled PECAM1 antibodies (30884X) available from PharMingen (PharMingen, Becton Dickinson Bio Sciences, San Jose, CA, USA) as described in Levenberg, S. et al., (Endothelial cells derived from human embryonic stem cells. Proc. Natl. Acad. Sci. USA. 2002. 99: 4391-4396). Hematopoietic cells are isolated using fluorescently-labeled antibodies such as CD34-FITC, CD45-PE, CD31-PE, CD38-PE, CD9O-FITC, CD117-PE, CD15-FITC, class I-FITC, all of which IgG1 are available from PharMingen, CD133/1-PE (IgG1) (available from Miltenyi Biotec, Auburn, CA), and glycophorin A-PE (IgG1), available from Immunotech (Miami, FL). Live cells (i.e., without fixation) are analyzed on a FACScan (Becton Dickinson Bio Sciences) by using propidium iodide to exclude dead cells with either the PC-LYSIS or the CELL-QUEST software. It will be appreciated that isolated cells can be further enriched using magnetically-labeled second antibodies and magnetic separation columns (MACS, Miltenyi) as described by Kaufman, D. S. et al., (Hematopoietic colony-forming cells derived from human embryonic stem cells. Proc. Natl. Acad. Sci. USA. 2001, 98: 10716-10721).

According to yet an additional preferred embodiment of the present invention, isolating is effected by a mechanical separation of cells, tissues and/or tissue-like structures contained within the EBs.

For example, beating cardiomyocytes can be isolated from EBs as disclosed in U.S. Pat. Appl. No. 20030022367 to Xu et al. Four-day-old EBs of the present invention are transferred to gelatin-coated plates or chamber slides and are allowed to attach and differentiate. Spontaneously contracting cells, which are observed from day 8 of differentiation, are mechanically separated and collected into a 15-mL tube containing low-calcium medium or PBS. Cells are dissociated using Collagenase B digestion for 60-120 minutes at 37° C., depending on the Collagenase activity. Dissociated cells are then resuspended in a differentiation KB medium (85 mM KCl, 30 mM $K_2HPO_4$, 5 mM $MgSO_4$, 1 mM EGTA, 5 mM creatine, 20 mM glucose, 2 mM $Na_2ATP$, 5 mM pyruvate, and 20 mM taurine, buffered to pH 7.2, Maltsev et al., Circ. Res. 75:233, 1994) and incubated at 37° C. for 15-30 min. Following dissociation cells are seeded into chamber slides and cultured in the differentiation medium to generate single cardiomyocytes capable of beating.

According to still an additional preferred embodiment of the present invention, isolating is effected by subjecting the EBs to differentiation factors to thereby induce differentiation of the EBs into lineage specific differentiated cells.

Following is a non-limiting description of a number of procedures and approaches for inducing differentiation of EBs to lineage specific cells.

To differentiate the EBs of the present invention into neural precursors, four-day-old EBs are cultured for 5-12 days in tissue culture dishes including DMEM/F-12 medium with 5 mg/ml insulin, 50 mg/ml transferrin, 30 nM selenium chloride, and 5 mg/ml fibronectin (ITSFn medium, Okabe, S. et al., 1996, Mech. Dev. 59: 89-102). The resultant neural precursors can be further transplanted to generate neural cells in vivo (Brüstle, O. et al., 1997. In vitro-generated neural precursors participate in mammalian brain development. Proc. Natl. Acad. Sci. USA. 94: 14809-14814). It will be appreciated that prior to their transplantation, the neural precursors are trypsinized and triturated to single-cell suspensions in the presence of 0.1% DNase.

EBs of the present invention can differentiate to oligodendrocytes and myelinate cells by culturing the cells in modified SATO medium, i.e., DMEM with bovine serum albumin (BSA), pyruvate, progesterone, putrescine, thyroxine, triiodothryonine, insulin, transferrin, sodium selenite, amino acids, neurotrophin 3, ciliary neurotrophic factor and Hepes (Bottenstein, J. E. & Sato, G. H., 1979, Proc. Natl. Acad. Sci. USA 76, 514-517; Raff, M. C., Miller, R. H., & Noble, M., 1983, Nature 303: 390-396]. Briefly, EBs are dissociated using 0.25% Trypsin/EDTA (5 min at 37° C.) and triturated to single cell suspensions. Suspended cells are plated in flasks containing SATO medium supplemented with 5% equine serum and 5% fetal calf serum (FCS). Following 4 days in culture, the flasks are gently shaken to suspend loosely adhering cells (primarily oligodendrocytes), while astrocytes are remained adhering to the flasks and further producing conditioned medium. Primary oligodendrocytes are transferred to new flasks containing SATO medium for additional two days. Following a total of 6 days in culture, oligospheres are either partially dissociated and resuspended in SATO medium for cell transplantation, or completely dissociated and a plated in an oligosphere-conditioned medium which is derived from the previous shaking step [Liu, S. et al., (2000). Embryonic stem cells differentiate into oligodendrocytes and myelinate in culture and after spinal cord transplantation. Proc. Natl. Acad. Sci. USA. 97: 6126-6131].

For mast cell differentiation, two-week-old EBs of the present invention are transferred to tissue culture dishes including DMEM medium supplemented with 10% FCS, 2 mM L-glutamine, 100 units/ml penicillin, 100 mg/ml streptomycin, 20% (v/v) WEHI-3 cell-conditioned medium and 50 ng/ml recombinant rat stem cell factor (rrSCF, Tsai, M. et al., 2000. In vivo immunological function of mast cells derived from embryonic stem cells: An approach for the rapid analysis of even embryonic lethal mutations in adult mice in vivo. Proc Natl Acad Sci USA. 97: 9186-9190). Cultures are expanded weekly by transferring the cells to new flasks and replacing half of the culture medium.

To generate hemato-lymphoid cells from the EBs of the present invention, 2-3 days-old EBs are transferred to gas-permeable culture dishes in the presence of 7.5% $CO_2$ and 5% $O_2$ using an incubator with adjustable oxygen content. Following 15 days of differentiation, cells are harvested and dissociated by gentle digestion with Collagenase (0.1 unit/mg) and Dispase (0.8 unit/mg), both are available from F.Hoffman-La Roche Ltd, Basel, Switzerland. CD45-positive cells are isolated using anti-CD45 monoclonal antibody (mAb) M1/9.3.4.HL.2 and paramagnetic microbeads (Miltenyi) conjugated to goat anti-rat immunoglobulin as described in Potocnik, A. J. et al., (Immunology Hemato-lymphoid in vivo reconstitution potential of subpopulations derived from in vitro differentiated embryonic stem cells. Proc. Natl. Acad. Sci. USA. 1997, 94: 10295-10300). The isolated CD45-positive cells can be further enriched using a single passage over a MACS column (Miltenyi).

It will be appreciated that the culturing conditions suitable for the differentiation and expansion of the isolated lineage specific cells include various tissue culture media, growth factors, antibiotic, amino acids and the like and it is within the capability of one skilled in the art to determine which conditions should be applied in order to expand and differentiate particular cell types and/or cell lineages.

Additionally or alternatively, lineage specific cells can be obtained by directly inducing the expanded, undifferentiated ESCs to culturing conditions suitable for the differentiation of specific cell lineage.

In addition to the lineage-specific primary cultures, EBs of the present invention can be used to generate lineage-specific cell lines which are capable of unlimited expansion in culture.

Cell lines of the present invention can be produced by immortalizing the EB-derived cells by methods known in the art, including, for example, expressing a telomerase gene in the cells (Wei, W. et al., 2003. Mol Cell Biol. 23: 2859-2870) or co-culturing the cells with NIH 3T3 hph-HOX11 retroviral producer cells (Hawley, R. G. et al., 1994. Oncogene 9: 1-12).

It will be appreciated that since the lineage-specific cells or cell lines obtained according to the teachings of the present invention are developed by differentiation processes similar to those naturally occurring in the human embryo they can be further used for human cell-based therapy and tissue regeneration.

Thus, the present invention envisages the use of the expanded and/or differentiated lineage-specific cells or cell lines of the present invention for treating a disorder requiring cell replacement therapy.

For example, oligodendrocyte precursors can be used to treat myelin disorders (Repair of myelin disease: Strategies and progress in animal models. Molecular Medicine Today. 1997. pp. 554-561), chondrocytes or mesenchymal cells can be used in treatment of bone and cartilage defects (U.S. Pat. No. 4,642,120) and cells of the epithelial lineage can be used in skin regeneration of a wound or burn (U.S. Pat. No. 5,716,411).

For certain disorders, such as genetic disorders in which a specific gene product is missing [e.g., lack of the CFTR gene-product in cystic fibrosis patients (Davies J C, 2002. New therapeutic approaches for cystic fibrosis lung disease. J. R. Soc. Med. 95 Suppl 41:58-67)], ESC-derived cells are preferably manipulated to over-express the mutated gene prior to their administration to the individual. It will be appreciated that for other disorders, the ESC-derived cells should be manipulated to exclude certain genes.

Over-expression or exclusion of genes can be effected using knock-in and/or knock-out constructs [see for example, Fukushige, S. and Ikeda, J. E.: Trapping of mammalian promoters by Cre-lox site-specific recombination. DNA Res 3 (1996) 73-50; Bedell, M. A., Jerkins, N. A. and Copeland, N. G.: Mouse models of human disease. Part I: Techniques and resources for genetic analysis in mice. Genes and Development 11 (1997) 1-11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751-62].

In addition to cell replacement therapy, the lineage specific cells of the present invention can also be utilized to prepare a cDNA library. mRNA is prepared by standard techniques from the lineage specific cells and is further reverse transcribed to form cDNA. The cDNA preparation can be subtracted with nucleotides from embryonic fibroblasts and other cells of undesired specificity, to produce a subtracted cDNA library by techniques known in the art.

The lineage specific cells of the present invention can be used to screen for factors (such as small molecule drugs, peptides, polynucleotides, and the like) or conditions (such as culture conditions or manipulation) that affect the differentiation of lineage precursor to terminally differentiated cells. For example, growth affecting substances, toxins or potential differentiation factors can be tested by their addition to the culture medium.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N. Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, CT (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Culturing Human Embryonic Stem Cell With a Medium Containing the IL-6-IL-6 Receptor (IL6RIL6) Chimera To optimize culturing conditions of hESCs on feeder-layer free culturing systems, the present inventors have tested various combinations of growth factors, as follows.

Materials and Experimental Methods hESC culture—Human embryonic stem cell (hESC) lines 1-6 and 1-3 [Amit & Itskovitz-Eldor, 2002] were cultured for 46 and 39 passages respectively, with inactivated mouse embryonic fibroblasts (MEFs) in an "hESC basic culture medium" consisting of 85% Ko-DMEM, supplemented with 15% serum replacement (SR), 2 mM L-glutamine, 0.1 mM β-mercaptoethanol, 1% non-essential amino acid stock, and 4 ng/ml bFGF (all Gibco Invitrogen Corporation products, Grand Island NY, USA).

To test various media combinations on feeder-layer free culturing systems, hESCs were transferred to 50 μg per 10 cm$^2$ fibronectin-covered plates (human plasma fibronectin, Chemicon International, Temecula CA, USA) in the presence of the "hESC basic culture medium" with the following combinations of cytokines:

(i) "CM6 medium"—0.3 ng/ml Interleukin-6 (IL6) and 0.5 ng/ml IL6 soluble receptor (both from R&D Systems Minneapolis MN, USA);

(ii) "IL-6-IL-6 receptor (IL6RIL6) chimera"—50 ng/ml, 100 ng/ml, 200 ng/ml or 300 ng/ml of IL6RIL6 chimera (Chebath J, et al., 1997 and WO 99/02552 to Revel M., et al. SEQ ID NO:31). When used with 100 ng/ml of the IL6RIL6 chimera, this medium is also called CM100.

(iii) Control medium—4 ng/ml bFGF (Gibco Invitrogen Corporation, Grand Island NY, USA).

Cells were passaged every four to six days using 1 mg/ml type IV collagenase (Gibco Invitrogen Corporation, Grand Island NY, USA). Cells were frozen in liquid nitrogen using a freezing solution consisting of 10% DMSO (Sigma, St Louis MO, USA), 15% SR (Chemicon International, Temecula CA, USA) and 75% Ko-DMEM (Gibco-Invitrogen Corporation, Grand Island NY, USA) [Amit et al, 2004].

Immunohistochemistry—Undifferentiated hESCs grown in the feeder-free culture system and differentiated cells dissociated using trypsin-EDTA from 14-day-old EBs were fixed with 4% paraformaldehyde and incubated overnight at 4° C. with 1:50 dilutions of the following primary antibodies: stage-specific embryonic antigen (SSEA) 1 (SSEA-1), 3 (SSEA-3) and 4 (SSEA-4) (Hybridoma Bank, Iowa, USA), tumor recognition antigen (TRA) 1-60 and TRA1-81 (Chemicon International, Temecula CA, USA) and Oct4 (Santa Cruse). Cys 3 conjugated antibodies (Chemicon International, Temecula CA, USA) were used as secondary antibodies at a 1:100 dilution.

Karyotype analysis—Karyotype analysis (G-banding) was performed on at least 20 cells from each sample, two samples per test, as previously described [Amit et al, 2003]. Karyotypes were analyzed and reported according to the "International System for Human Cytogenetic Nomenclature" (ISCN).

EB formation—For the formation of EBs, one to four confluent wells were used in a six-well plate (40 cm$^2$). ESCs were removed from their culture dish using 1 mg/ml type IV collagenase, further broken into small clumps using 1000 µGilson pipette tips, and cultured in suspension in 58 mm petri dishes (Greiner, Frickenhausen, Germany). EBs were grown in medium consisting of 80% Ko-DMEM, supplemented with 20% FBSd (HyClone, Utah, USA), 1 mM L-glutamine, 0.1 mM β-mercaptoethanol, and 1% non-essential amino acid stock (all but FBSd from Gibco Invitrogen Corporation, Grand Island NY, USA). 10 day-old EBs were harvested for RNA isolation and histological examination.

RT PCR analysis—Total RNA was isolated from hESCs grown for 10-15 passages in feeder-free conditions, or from 10 day-old EBs (formed from cells grown in the feeder-free system) using Tri-Reagent (Sigma, St. Louis MO, USA), according to the manufacturer's instructions. cDNA was synthesized from 1 µg total RNA using MMLV reverse transcriptase RNase H minus (Promega, Madison WI, USA). PCR reactions included denaturation for 5 minutes at 94° C. followed by repeated cycles of 94° C. for 30 seconds, annealing for 30 seconds at a temperature specified in Table 1, hereinbelow, and extension at 72° C. for 30 seconds. PCR primers and reaction conditions used are described in Table 1, hereinbelow. PCR products were size-fractionated using 2% agarose gel electrophoresis. DNA markers were used to confirm the size of the resultant fragments.

TABLE 1

RT-PCR primers and PCR conditions are provided along with the GenBank Accession numbers of the amplified transcripts.
RT-PCR conditions

| Gene product (Accession number) | Forward (F) and reverse (R) primers (SEQ ID NO:) | Reaction Condition | Size (bp) |
|---|---|---|---|
| Oct-4 (S81255) | F: 5'-GAGAACAATGAGAACCTTCAGGA (SEQ ID NO: 1)<br>R: 5'-TTCTGGCGCCGGTTACAGAACCA (SEQ ID NO: 2) | 30 cycles at 60° C. in 1.5 mM MgCl$_2$ | 219 |
| Albumin (AF542069) | F: 5'-TGCTTGAATGTGCTGATGACAGGG (SEQ ID NO: 3)<br>R: 5'-AAGGCAAGTCAGCAGCCATCTCAT (SEQ ID NO: 4) | 35 cycles at 60° C. in 1.5 mM MgCl$_2$ | 302 |
| α-fetoprotein (BC027881) | F: 5'-GCTGGATTGTCTGCAGGATGGGGAA (SEQ ID NO: 5)<br>R: 5'-TCCCCTGAAGAAAATTGGTTAAAAT (SEQ ID NO: 6) | 30 cycles at 60° C. in 1.5 mM MgCl$_2$ | 216 |
| NF-68KD (NFH (AY156690; X15307; X15309) | F: 5'-GAGTGAAATGGCACGATACCTA (SEQ ID NO: 7)<br>R: 5'-TTTCCTCTCCTTCTTCACCTTC (SEQ ID NO: 8) | 30 cycles at 60° C. in 2 mM MgCl$_2$ | 473 |
| α-cardiac actin (NM_005159) | F: 5'-GGAGTTATGGTGGGTATGGGTC (SEQ ID NO: 9)<br>R: 5'-AGTGGTGACAAAGGAGTAGCCA (SEQ ID NO: 10) | 35 cycles at 65° C. in 2 mM MgCl$_2$ | 486 |
| β-Actin (NM_001101) | F: 5'-ATCTGGCACCACACCTTCTACAATGAGCTGCG (SEQ ID NO: 11)<br>R: 5'-CGTCATACTCCTGCTTGCTGATCCACATCTGC (SEQ ID NO: 12) | 35 cycles at 62° C. in 1.5 mM MgCl$_2$ | 838 |
| Sox2 (Z31560) | 5' CCCCCGGCGGCAATAGCA (SEQ ID NO: 13)<br>3' TCGGCGCCGGGGAGATACAT (SEQ ID NO: 14) | 35 cycles at 60° C. in 1.5 mM MgCl$_2$ | 448 |
| Rex1 (AF450454) | 5' GCGTACGCAAATTAAAGTCCAGA (SEQ ID NO: 15)<br>3' CAGCATCCTAAACAGCTCGCAGAAT (SEQ ID NO: 16) | 35 cycles at 56° C. in 1.5 mM MgCl$_2$ | 306 |
| CX43 (NM_000165) | 5' TACCATGCGACCAGTGGTGCGCT (SEQ ID NO: 17)<br>3' GAATTCTGGTTATCATCGGGGAA (SEQ ID NO: 18) | 35 cycles at 61° C. in 1.5 mM MgCl$_2$ | 295 |

TABLE 1-continued

RT-PCR primers and PCR conditions are provided along with the GenBank
Accession numbers of the amplified transcripts.
RT-PCR conditions

| Gene product (Accession number) | Forward (F) and reverse (R) primers (SEQ ID NO:) | Reaction Condition | Size (bp) |
|---|---|---|---|
| FGF4 (NM_002007) | 5' CTACAACGCCTACGAGTCCTACA (SEQ ID NO: 19)<br>3' GTTGCACCAGAAAAGTCAGAGTTG (SEQ ID NO: 20) | 35 cycles at 52° C. in 1.5 mM MgCl$_2$ | 370 |
| Glucagon (X03991) | 5' CTCAGTGATCCTGATCAGATGAACG (SEQ ID NO: 21)<br>3' AGTCCCTGGCGGCAAGATTATCAAG (SEQ ID NO: 22) | 35 cycles at 65° C. in 1.5 mM MgCl$_2$ | 370 |
| β-globulin (V00499) | 5' ACCTGACTCCTGAGGAGAAGTCTGC (SEQ ID NO: 23)<br>3' TAGCCACACCAGCCACCACTTTCTG (SEQ ID NO: 24) | 35 cycles at 65° C. in 1.5 mM MgCl$_2$ | 410 |
| Flk1 (NM_002253) | 5' ATGCACGGCATCTGGGAATC (SEQ ID NO: 25)<br>3' GCTACTGTCCTGCAAGTTGCTGTC (SEQ ID NO: 26) | 35 cycles at 65° C. in 1.5 mM MgCl$_2$ | 537 |
| AC133 (NM_006017) | 5' CAGTCTGACCAGCGTGAAAA (SEQ ID NO: 27)<br>3' GGCCATCCAAATCTGTCCTA (SEQ ID NO: 28) | 35 cycles at 65° C. in 1.5 mM MgCl$_2$ | 200 |
| Nanog (NG_004095) | 5' ACTAACATGAGTGTGGATCC (SEQ ID NO: 29)<br>3' TCATCTTCACACGTCTTCAG (SEQ ID NO: 30) | 35 cycles at 61° C. in 1.5 mM MgCl$_2$ | 800 |

Experimental Results

Medium supplemented with a combination of 100 ng/ml IL6RIL6 chimera and 4 ng/ml bFGF is most suitable to support undifferentiated proliferation of hESCs on a feeder-free culture system—Several concentrations of the IL6RIL6 chimera were tested for the ability to support the feeder-layer free culture of hESCs. Initially, two measures were used to estimate the ability of the hESCs to grow in the feeder-free culture system, namely percentage of differentiation and rate of growth.

The medium supplemented with the combination of 100 ng/ml IL6RIL6 chimera and 4 ng/ml bFGF was found to be the most suitable to support undifferentiated feeder-layer free hESC proliferation. Culturing hESCs with a culture medium consisting of 4 ng/ml bFGF and the chimera components IL-6 and IL-6 soluble receptor failed to support hESC prolonged culture and resulted in differentiation of hESCs within 3-5 passages (data not shown). Although 70% of the hESCs remained in the undifferentiated stage in these conditions for a few passages, the proliferation rate was low and with each passage the number of surviving hESCs decreased. In addition, culturing of hESCs in a medium containing the IL6RIL6 chimera and serum replacement, in the absence of bFGF, resulted in low proliferation of cells and failure to maintain the hESCs beyond 1-2 passages (data not shown). However, in medium supplemented with either 100 ng/ml or 300 ng/ml IL6RIL6 chimera and 4 ng/ml bFGF, the hESCs could be cultured continuously in feeder-layer free conditions for at least 43 passages. hESCs cultured in these conditions (in the presence of the IL6RIL6 chimera medium) maintained their ESC features, including undifferentiated proliferation, karyotype stability and pluripotency as was tested following 28 passages. Based on morphology, the background spontaneous differentiation rates were about 15%, similar to those occurring in other feeder layer-free culture methods [Xu et al, 2001, 2005; Amit et al, 2004]. Examples of undifferentiated colonies cultured in feeder-layer free conditions are illustrated in FIGS. 1a-1f. Interestingly, when cultured in a medium supplemented with the IL6RIL6 chimera and bFGF using fibronectin as substrate for the feeder-free culture system, the cells differentiated at the periphery of the colonies and formed an outgrowth of feeder-like cells (FIG. 1a). In similar cultures, laminin did not induce such differentiation (FIG. 1c) but, human and mouse laminin matrices were found to be inconsistent in their ability to support hESC undifferentiated growth and, therefore, fibronectin appears preferable despite the formation of feeder-like cells. Former studies on feeder-layer free cultures of hESCs also reported the formation of feeder-like cells [Xu et al, 2001].

Feeder-free culture system in the presence of a culture medium containing the IL6RIL6 chimera supports hESCs with typical morphology—When compared to hESCs cultures on exogenous feeder layers, no morphological differences could be observed between colonies grown in the feeder layer-free culture system (a fibronectin matrix and a medium supplemented with IL6RIL6 chimera and bFGF) and those grown on MEFs (FIGS. 1a-1f and data not shown). Correspondingly, the morphological features at the single-cell level remained unchanged, the cells remained small and round, and exhibited high nucleus-to-cytoplasm ratio, with a notable presence of one to three nucleoli and with typical spacing between the cells (FIGS. 1a-1f. The hESC population doubling time was similar to that observed when grown on MEFs (about 36 hours), and in the present feeder-free conditions the cells could be passaged routinely every four to six days, at a ratio of 1/2 or 1/3, similar to the splitting ratio employed when the hESCs are cultured on MEFs. The cells were passaged at the same seeding efficiency as with MEF of about 1 million cells per 10 cm², with the same viability rate of over 90%. Using 15% SR and 10% DMSO, cells were successfully frozen and thawed.

The fibronectin feeder-layer free culture system supplemented with a medium containing the IL6RIL6 chimera supports hESCs with normal karyotype for at least 23 passages—Karyotype analysis by Giemsa banding was carried out on two separate cultures, representing the two medium conditions: medium supplemented with 4 ng/ml bFGF and either 100 ng/ml or 300 ng/ml IL6RIL6 chimera 23 passages after transferring the cells into the feeder-layer environment which is based on fibronectin. At least 20 cells were tested from each sample, 40 cells from each medium combination. All examined cells were found to sustain normal karyotype of 46, XX and 46,XY for cell lines 13 and 16, respectively. Examples of chromosomes from examined cells are illustrated in FIG. 2. Overall, these results demonstrate that the cells' karyotype remains stable in the fibronectin based feeder free culture system supplemented with the IL6RIL6 chimera medium, similarly to ESCs grown with MEFs.

hESCs cultured on fibronectin feeder free culture systems supplemented with the IL6RIL6 chimera medium express typical hESC markers of undifferentiated cells—Several surface markers typical of primate undifferentiated ES cells were examined using immunofluorescent staining as described elsewhere [Thomson et al, 1995, 1996, 1998]. hESCs cultured on the fibronectin feeder-free culture system for 27 passages in medium supplemented with 100 ng/ml or 300 ng/ml of the IL6RIL6 chimera were found to be strongly positive to surface markers TRA-1-60 (FIG. 3a) Oct4 (FIG. 3b), SSEA4 (FIG. 3c), and TRA-1-81 (data not shown). As in other primate ES cells, staining with SSEA3 was weak and negative for SSEA1 (data not shown).

The IL6RIL6 chimera medium is capable of supporting pluripotent hESCs as evident by the in vitro differentiation into embryoid bodies (EBs)—The developmental potential of the cells after prolonged culture in feeder layer-free conditions was examined in vitro by the formation of EBs. When cultured in suspension, after 7 passages in medium supplemented with either 100 ng/ml or 300 ng/ml IL6RIL6 chimera, hESCs formed EBs similar to those created by ES cells grown on MEFs. Within these EBs, stem cells differentiated into cell types representative of the three embryonic germ layers.

EBs formed from the hESCs cultured on the IL6RIL6 chimera expressed typical differentiation markers of all embryonic cell lineages—To further define the expression pattern of the undifferentiated hESCs grown on the fibronectin-based feeder free culture system in the presence of a medium containing the IL6RIL6 chimera, RT-PCR analysis was performed using primers specific to both differentiation and undifferentiated cells (primers employed are listed in Table 1, hereinabove). As is shown in FIGS. 4a-4l, while undifferentiated cells cultured on the fibronectin feeder free culture system using medium supplemented with the IL6RIL6 chimera expressed undifferentiated genetic markers such as Oct 4 (FIG. 4a), Nanog (data not shown), Sox2 (FIG. 4b), Rex1 (FIG. 4c), Cx43 (FIG. 4d) and FGF4 (FIG. 4e) [Bhattacharya et al, 2004], cells harvested from 10 day-old EBs expressed genes such as albumin (FIG. 4f) and glucagon (FIG. 4g) (typical of the embryonic endoderm), α-cardiac actin (FIG. 4i), β-globulin (FIG. 4h) and Flk1 (FIG. 4j) (typical of the embryonic mesoderm), and AC133 (FIG. 4k) and neurofilament (NFH; FIG. 4l) (typical of the embryonic ectoderm).

Altogether, these results demonstrate the identification of a defined medium based on the IL6RIL6 chimera which is suitable for maintaining hESCs in a pluripotent and undifferentiated state on a feeder-free culture system such as the fibronectin based feeder free system.

Analysis and Discussion

Human ESCs, like mouse ES cells, are traditionally cultured with MEFs, which may expose them to animal pathogens. In this study, the present inventors have demonstrated a defined medium and feeder layer-free culture system based on the use of Serum Replacement™, bFGF, IL6RIL6 chimera and human fibronectin as a matrix substitute.

Several concentrations of the IL6RIL6 chimera were tested for their ability to maintain hESCs in an undifferentiated state. The most suitable medium was that supplemented with 100 ng/ml of the IL6RIL6 chimera together with 4 ng/ml bFGF, in which the three transferred hESC lines continued to proliferate while retaining normal hESC features throughout the prolonged culture.

Cells cultured in these conditions maintained all characteristics of ES cells. After prolonged culture of up to 28 passages, the cells remained undifferentiated, as demonstrated by the colony and single cell morphology, and by the expression of surface markers typical of undifferentiated primate ESCs [Thomson et al, 1995, 1996, 1998; Reubinoff et al, 2000]. In addition, while cultured in these conditions, hESCs expressed specific markers for the undifferentiated stage such as Oct 4, Sox 2, Rex1 and FGF4, as demonstrated by immunofluorescence (for Oct4) and RT-PCR analyses (for Oct4, Sox 2, Rex1 and FGF4).

Karyotype analysis carried out on representative cell samples demonstrated that the hESCs' karyotype remained stable in the proposed conditions (after 23 passages at the tested conditions). None of the examined 40 cells exhibited karyotype abnormalities.

The cells' pluripotency was examined in vitro. Cells cultured in the feeder layer-free culture system for more than 10 passages, formed EBs similar to those created when grown on MEFs [Itskovitz-Eldor et al, 2000]. RT-PCR analysis demonstrated that cells within these EBs differentiated into different cell types representative of the three embryonic germ layers.

These results demonstrate that hESCs can be maintained as undifferentiated cells in defined feeder- and serum-free conditions which include the IL6RIL6 chimera while exhibiting hESC features.

The mechanism by which hESCs self-maintain is still not clear. In mouse ESCs the role of LIF and other members of the IL-6 family, acting through gp130 and the JAK/STAT3 pathway, in maintaining ESCs undifferentiated prolonged culture is well known [Smith et al, 1988; Williams et al, 1988; Rose et al, 1994; Conover et al, 1993; Niwa et al, 1998]. Furthermore, to date the only method for deriving new mouse ESC lines in feeder layer-free conditions is based on the addition of factors from the IL-6 family [Nichols et al, 1994]. The IL6RIL6 chimera was demonstrated as the most potent factor in supporting the feeder layer-free isolation of mouse ESC lines (Nichols et al, 1994). Previous studies did not demonstrate a significant effect of the IL-6 family, including a fusion protein of portions of IL-6 and the IL-6 receptor, on the self-maintenance of undifferentiated hESCs [Daheron et al, 2004; Humphrey et al, 2004; Sato et al, 2004]. The specific conditions for hESC cultures described here may explain why the IL6RIL6 chimera was effective in supporting the proliferation of hESC with minimal differentiation. One difference being the use of fibronectin substrate as a matrix (and not mouse laminin) and another being the precise schedule of hESC passaging. Further research is required to elucidate the underlying mechanisms of action of the IL6RIL6 chimera at the level of signal transduction, its time course and intensity at which different pathways (JAK/STAT, PI3 kinase, MAPK, see Hirano et al, 1997) are activated.

Future clinical uses of hESCs will require a reproducible, well-defined and xeno-free culture system. Although the serum replacement (SR) used in the present study is considered such, it contains "Albumax" which is a lipid-enriched bovine serum albumin and, therefore, is not animal-free. The well-defined conditioned media demonstrated in the present study are suitable for culturing hESCs and may be advantageous for undertaking research on the mechanisms of ESC self-maintenance, especially of the possible roles of the LIF/STAT3 pathway and various integrins as fibronectin receptors. Other studies using hESCs, such as the research on differentiation pathways and mechanisms, will benefit from the availability of a well-defined and reproducible culture system.

This culture system is a further step forward towards fully defined culture conditions for hESCs, and promotes the development of a xeno-free culture system for hESCs.

Example 2

Culturing Human Embryonic Stem Cell with a Medium Containing TGF-Beta Isoforms Devoid of Serum, Serum Replacement and Albumin Materials and Experimental Methods ESC culture—Human embryonic stem cell (hESC) lines 1-6, 14 and 1-3 [Amit & Itskovitz-Eldor, 2002] were cultured with inactivated mouse embryonic fibroblasts (MEFs) for 40-60 passages in a "basic hESC culture medium" consisting of 85% DMEM/F12 (Biological Industries, Biet Haemek, Israel) supplemented with 15% serum replacement (SR), 2 mM L-glutamine, 0.1 mM ⊕-mercaptoethanol, 1% non-essential amino acid stock, and 4 ng/ml basic fibroblast growth factor (bFGF) (all Gibco Invitrogen Corporation products, Grand Island NY, USA).

To test the ability of various culture media to support the growth of hESC in an undifferentiated yet pluripotent state the hESCs were transferred to several culture systems:
  (i) Fibronectin feeder-free culture system—50 µg per 10 cm² fibronectin-covered plates (human plasma fibronectin, Chemicon International, Temecula CA, USA);
  (ii) Matrigel™ feeder-free culture system—Matrigel™ (BD Biosciences, Bedfrod, MA, USA);
  (iii) MEFs—mouse embryonic fibroblast feeder layer system;
  (iv) Foreskins fibroblasts—foreskin fibroblasts feeder layer system.

Tested media—The tested medium were based on:
  (i) D1 medium—Mab ADCB medium (HyClone, Utah, USA) supplemented with 2 mM L-glutamine (Invitrogen Corporation products, Grand Island NY, USA), 0.12 ng/ml TGFβ$_1$ (from R&D Systems Minneapolis MN, USA), and 10 ng/ml bFGF (Invitrogen Corporation products, Grand Island NY, USA).
  (ii) D2 medium—Mab ADCB medium (HyClone, Utah, USA) supplemented with 2 mM L-glutamine (Invitrogen Corporation products, Grand Island NY, USA), 2 ng/ml TGFβ$_3$ and 10 ng/ml bFGF (Invitrogen Corporation products, Grand Island NY, USA).
  (iii) HA16 medium—96% DMEM/F12 (Biological Industries, Biet Haemek, Israel) supplemented with 1:1000 dilution of the ITS Premix [the ITS premix is a X1000 stock solution obtained from BD Biosciences, Bedford, MA, USA and consists of 12.5 mg Insulin, 12.5 mg Transferrin and 12.5 mg Selenius acid], 2 mM L-glutamine, 2 ng/ml TGFβ$_3$ (from R&D Systems Minneapolis MN, USA), 4 ng/ml bFGF, 500 ng/ml ascorbic acid (Sigma, Steinheim, Germany), and a 1:1000 dilution of a lipid mixture (Sigma Cat. No. L5146, Steinheim, Germany) (all but those otherwise specified were obtained from Gibco Invitrogen Corporation products, Grand Island NY, USA).
  (iv) HA19 medium—96% DMEM/F12 (Biological Industries, Beth Haemek, Israel) supplemented with 1:1000 dilution of the ITS premix (BD Biosciences, Bedford, MA, USA), 2 mM L-glutamine, 2 ng/ml TGFβ$_3$ (from R&D Systems Minneapolis MN, USA), 4 ng/ml bFGF, 500 ng/ml ascorbic acid (Sigma, Steinheim, Germany), a 1:1000 dilution of a lipid mixture (Sigma Cat. No. L5146, Steinheim, Germany) and a 1:100 dilution of Simfronic 68 (Pluronic F-68 solution, P5556 from Sigma, Steinheim, Germany, the stock is 10%, the F-68 in culture is provided at a concentration of 0.1%) (Sigma, Steinheim, Germany) (all but those otherwise specified were obtained from Gibco Invitrogen Corporation products, Grand Island NY, USA).
  (v) CM100F medium—85% DMEM/F12 (Biological Industries, Biet Haemek, Israel) supplemented with 15% serum replacement (SR), 2 mM L-glutamine, 0.1 mM β-mercaptoethanol, 1% non-essential amino acid stock, 4 ng/ml basic fibroblast growth factor (bFGF) and 100 ng/ml IL6RIL6 chimera (SEQ ID NO:31, a kind gift from Prof. Revel M, the Weizmann Inst. Rehovot, Israel) (all but those otherwise specified were obtained from Gibco Invitrogen Corporation products, Grand Island NY, USA). As a control, the same culture media was used with the removal of the growth factors (except for bFGF which remained in the control culture medium) and the IL6RIL6 chimera.
  (vi) "IL6-IL-6 receptor (IL6RIL6) chimera"—85% Ko-DMEM, supplemented with 15% serum replacement (SR), 2 mM L-glutamine, 0.1 mM 13-mercaptoethanol, 1% non-essential amino acid stock, 4 ng/ml bFGF and 50 ng/ml, 100 ng/ml, 200 ng/ml or 300 ng/ml of IL6RIL6 chimera (Chebath J, et al., 1997 and WO 99/02552 to Revel M., et al. SEQ ID NO:31) (all Gibco Invitrogen Corporation products, Grand Island NY, USA). When used with 100 ng/ml of the IL6RIL6 chimera, this medium is also called CM100.
  (vii) HACM100 medium—96% DMEM/F12 (Biological Industries, Biet Haemek, Israel) supplemented with a 1:1000 dilution of the ITS premix (BD Biosciences, Bedford, MA, USA), 2 mM L-glutamine, 4 ng/ml bFGF, 500 ng/ml ascorbic acid (Sigma, Steinheim, Germany), a 1:1000 dilution of a lipid mixture (Sigma Cat. No. L5146, Steinheim, Germany) and 100 ng/ml of IL6RIL6 chimera. Cells were passaged every four to six days using 1.5 mg/ml type IV collagenase (Worthington biochemical corporation, Lakewood, NJ, USA). Cells were frozen in liquid nitrogen using a freezing solution consisting of 10% DMSO (Sigma, St Louis MO, USA), 40% human serum (HyClone, Utah, USA) and 50% DMEM/F12 (Biological Industries, Beit Haemek, Israel).

Derivation of New hESC Lines

Blastocyst cultivation—Zygotes were donated by couples undergoing pre-implantation genetic diagnosis (PGD) or in vitro fertilization (IVF) at Cornell Medical College, NY, who signed informed consent forms. The couples underwent the traditional IVF procedure after ovarian stimulation with gonadotropins and oocyte retrieval. Zygotes were cultured to the blastocyst stage according to IVF laboratory standard protocol: under oil using specialized C1/C2 media for insemination, growth and blastocyst development (Cornell).

Derivation of hESC lines—After digestion of the zona pellucida by Tyrode's acidic solution (Sigma, St Louis MO, USA) or its mechanical removal, the exposed blastocysts were placed in whole on a mitotically inactivated foreskin fibroblasts feeder layer (line F21 which was cultured in an animal free medium since its derivation until used). For the derivation and initial passages, cells were grown in the D2 or HA16 culture medium. The cells were initially passaged mechanically every four to ten days.

Immunohistochemistry—Undifferentiated hESCs grown in the tested culture system were fixed with 4% paraformaldehyde and exposed to the primary antibodies (1:50) overnight at 4° C. Stage-specific embryonic antigen (SSEA) 1, 3 and 4 (Hybridoma Bank, Iowa, USA), tumor recognition antigen (TRA) 1-60 and TRA1-81 (Chemicon International, Temecula CA, USA) and Oct 4 (Santa Cruz Biotechnology, Santa Cruz, CA, USA) were used as primary antibodies. Cys 3 conjugated antibodies (Chemicon International, Temecula CA, USA) were used as secondary antibodies (1:200);

Karyotype analysis—Karyotype analysis (G-banding) was performed on at least 20 cells from each sample, two samples per test, as previously described [Amit et al, 2003]. Karyotypes were analyzed and reported according to the "International System for Human Cytogenetic Nomenclature" (ISCN).

EB formation—For the formation of EBs, one to three confluent wells were used in a six-well plate (30 cm$^2$). ESCs were removed from their culture dish using 1 mg/ml type IV collagenase, further broken into small clumps using 1000 μl Gilson pipette tips, and cultured in suspension in 58 mm petri dishes (Greiner, Frickenhausen, Germany). EBs were grown in differentiation medium consisting of 80% DMEM/F12 (Biological Industries, Beit Haemek, Israel), supplemented with 20% FBSd (HyClone, Utah, USA), and 1 mM L-glutamine (Invitrogen Corporation, Grand Island NY, USA).

RT PCR—Total RNA was isolated from hESCs grown for over 10 passages in feeder-free conditions, or from 10 day-old EBs (created from cells grown in the tested culture system for more then 10 passages) using Tri-Reagent (Sigma, St. Louis MO, USA), according to the manufacturer's instructions. cDNA was synthesized from 1 μg total RNA using MMLV reverse transcriptase RNase H minus (Promega, Madison WI, USA). PCR reaction included denaturation for 5 minutes at 94° C. followed by repeated cycles of 94° C. for 30 seconds, annealing for 30 seconds at a temperature as specified in Table 1 and extension at 72° C. for 30 seconds. PCR primers and reaction conditions used are described in Table 1 (see Example 1, hereinabove). PCR products were size-fractionated using 2% agarose gel electrophoresis. DNA markers were used to confirm the size of the resultant fragments.

Teratoma formation—For teratoma formation, cells cultured in the offered culture methods for more than 15 passages, were injected into the rear leg muscle of 4-week-old male SCID-beige mice (two mice for each tested culture system). Cell numbers ranged from $5 \times 10^6$ cells to $10^7$ cells per injection. Three to eight to 12 weeks after injection the mice were sacrificed and the resulting teratomas examined histologically.

Experimental Results

In this study the ability of few medium combinations, HA16, HA19, D1, D2, and CM100 to support undifferentiated and prolonged culture of hESCs in different culture conditions was examined. The basic medium, D1 or D2, is a commercial medium design for industrial and clinical proposes for the culture of hybridomas in suspension. The medium is free from animal, serum products and proteins. HA16 and HA19 are based on defined materials only.

The effect of two isoforms of TGFβ, TGFβ$_1$ and TGFβ$_3$, in supporting hESCs undifferentiated culture, was examined. Initially, two measures were used to estimate the ability of hESCs to grow in several culture systems, namely percentage of differentiation and rate of growth. The culture system used were: (1) feeder layer-free culture system based on fibronectin or Matrigel™ which are the most used matrices; (2) MEF, and (3) foreskin fibroblast. Based on these two parameters, the media supplemented with TGFβ$_3$, D2, HA16 and HA19, were found to be the most suitable to support undifferentiated hESC proliferation in all tested culture methods. Culture medium supplemented with 10 ng/ml bFGF only, failed to support hESC prolonged culture, in all the tested culture conditions. Although 60% of the hESCs remained at the undifferentiated stage in these conditions for a few passages, the proliferation rate was low and with each passage the number of surviving hESCs decreased and the percentage of background differentiation was increased.

D1 medium on a feeder layer-free system is capable of maintaining all hESCs features along with high proliferation rate—When cultured in the feeder layer-free systems in the presence of the D1 medium, which is supplemented with TGF131, the hESCs maintained all hESCs features including high proliferation rates. When cultured on the tested feeder layers in the presence of the D1 medium, the hESCs demonstrated a relatively high background differentiation rate of 20% and low proliferation abilities as compared to hESCs cultured at the same feeder layers systems with the D2 HA19 or HA16 medium.

D1, D2 and HA16 media in feeder layer-free are capable of maintaining hESCs in a proliferative, undifferentiated state, with chromosomal stability and pluripotency—Human ESCs grown in the presence of the D1, D2 or HA16 medium in feeder-layer free conditions were cultured continuously for up to 53, 24 or 10 passages, respectively, while maintaining their ESC features, including undifferentiated proliferation, chromosomal stability (as tested by karyotype analysis, not shown) and pluripotency. The background differentiation rates were found to be less than 10%, which is similar to the differentiation rates occurring when hESCs are cultured in the traditional culture system based on MEFs as the feeder layer and medium supplemented with serum replacement and 4 ng/ml bFGF [Amit et al, 2000]. Examples of undifferentiated colonies cultured with D1, D2 or HA16 medium in feeder-layer free conditions and with the D2 or HA16 medium with the tested feeder layers are illustrated in FIGS. 5a-5d.

hESCs cultured on feeder layer-free systems in the presence of the D1 or the D2 medium are devoid of autofeeder—Interestingly, when the hESCs were cultured in either the D1 or D2 medium on the feeder layer-free system the cells did not differentiate at the periphery of the colonies and did not form an outgrowth of feeder-like cells (also called "autofeeder") (FIG. 5d), as described in other reports on feeder layer-free culture methods for hESCs (Xu et al, 2001). No morphological differences could be observed between colonies grown in the feeder layer-free culture system and those grown with feeder layers (FIGS. 5a-5d). Correspondingly, morphological features remained unchanged on a single-cell level, rendering cells small and round, and exhibiting high nucleus-to-cytoplasm ratio, with a notable presence of one to three nucleoli and typical spacing between the cells (FIGS. 5a-5d).

The D1, D2 or HA16 media are capable of maintaining hESCs with normal population doubling—Similar to cells grown on MEFs, cells cultured with D2 or HA16 medium in all tested culture methods, and the D1 medium in the feeder layer-free systems, were passaged routinely every four to six days, at the same ratio of 1/2 or 1/3, indicating a similar population doubling time as of hESCs grown on MEFs. The cells were passage at the same seeding efficiency of about 1 million cells per 10 cm², with the same viability rate of over 95%. Using 40% human serum and 10% DMSO, cells were successfully frozen and thawed.

Karyotype analysis revealed normal karyotype of hESCs grown with the D1, D2, CM100 or HA16 media—15 passages and more after transferring the cells into the tested environments, karyotype analysis was performed by Giemsa banding on two separate cultures, representing the four medium conditions, D1, D2, CM100 and HA16 at the different culture methods. At least 20 cells were tested from each sample, 40 cells from each medium combination. All examined cells were found to sustain normal karyotype of 46,XX for cell lines 13 and 14 and 46,XY for cell line 16 (data not shown). Overall, these results suggest that the cells' karyotype remains stable in the tested conditions, similarly to ESCs grown with MEFs using traditional methods (Amit et al, 2000).

hESCs cultured with the D1, D2 or HA16 express typical cell surface markers—Several surface markers typical of primate undifferentiated ES cells were examined using immunofluorescent staining (Thomson et al, 1995, 1996, 1998). hESCs cultured with the D1, D2 or HA16 medium for more than 20 passages, while using the tested culture conditions, were found to be strongly positive to surface markers TRA-1-60 (FIG. 6a), SSEA4 (FIG. 6b), TRA-1-81 (FIG. 6c) and Oct 4 (data not shown). As in other primate ES cells, staining with SSEA3 was weak and negative for SSEA1 (data not shown).

hESCs cultured with the D1, D2 or HA16 medium are pluripotent as tested by EBs formation in vitro—The developmental potential of the cells after prolonged culture in the tested culture methods was examined in vitro by the formation of embryoid bodies (EBs). After more than 15, 20 and 30 passages in medium D1, D2 and HA16, respectively hESCs formed EBs similar to those created by hESCs grown on MEFs (not shown). Within these EBs, stem cells differentiated into cell types representative of the three embryonic germ layers as described for EBs formed from hESCs cultured on other culture systems (Itskovitz-Eldor et al, 2000).

EBs formed from the hESCs cultured on the D1, D2 or HA16 medium are capable of differentiating into the ectoderm, endoderm and mesoderm cell lineages—While undifferentiated cells cultured in the tested medium, feeder layers and matrices, expressed undifferentiated genetic markers such as Oct 4, Nanog, Sox2, Rex1, Cx43 and FGF4 (not shown) [Bhattacharya et al, 2004], cells harvested from 10 day-old EBs expressed genes such as albumin and glucagon (endoderm), α-cardiac actin, β-globulin and Flk1 (mesoderm), and AC133 and neurofilament (ectoderm) as demonstrated by RT-PCR analysis (data not shown).

hESCs cultured with the D1, D2 or HA16 medium are pluripotent as tested by teratomas formation in vivo—The cells pluripotency was also tested in vivo by teratomas formation. hESCs cultured for over 12 passages in the HA16, D1 or D2 medium, in the tested culture systems formed teratomas following their injection into SCID-Beige mice. Within these teratomas, hESCs differentiated to representative tissues of the three embryonic germ layers including; cartilage, muscle, bone and fat (mesoderm), stratified epithelium, melanin containing epithelium (ectoderm), and kidney like structure (endoderm and mesoderm), and epithelium of endoderm origin (data not shown). Teratomas formation rates of 90%, and the number of injected cells were identical to those demonstrated by cells cultured using traditional methods (Amit et al, 2000).

Altogether, these results demonstrate that hESCs cells subjected to prolonged culture in the tested culture systems demonstrated all hESCs features including; pluripotency, chromosomal stability, expression of specific genes and surface markers and indefinite proliferation as undifferentiated cells.

Example 3

Evaluation of the Capacity of the TGF/β-Containing Media Devoid of Serum, Serum Replacement and Albumin to Support Derivation of hESC Line on Foreskin Fibroblasts in a Complete Xeno-Free System Materials and Experimental Methods—as in Example 2, Hereinabove.
Experimental Results The HA16 and D2 media are suitable for derivation of hESC line on foreskin fibroblast feeder layers in a complete xeno-free system—The medium combinations of the present invention were also tested for the ability to support hESC line derivation. While using the HA16 or D2 medium on foreskin fibroblasts as a supportive layer, new hESC lines were successfully derived and maintained for at least 2 passages (in the presence of the D2 medium) or at least 18 passages (in the presence of the HA16 medium). The hESC line derived on foreskin in the presence of the HA16 culture medium demonstrated stem cells morphology at passage 18 (and the culture is still ongoing), normal XY karyotype and pluripotency as evidenced by the formation of EBs (FIGS. 3a-3b and data not shown). The growth and success rates were similar to those obtained while using traditional culture methods. Since the used foreskin fibroblasts line, F21, were derived without any animal products, this new hESC lines were derived under complete xeno-free conditions. Although the new hESC lines still need to be tested for additional hESCs features, their morphology and proliferation rates indicate a typical hESCs culture.

Example 4

TGF/β-Containing Medium Devoid of Serum, Serum Replacement and Albumin is Suitable for Expanding and Maintaining hESCs in Suspension To examine the possibility of using the TGFβ-containing media devoid of serum, serum replacement and protein carrier (albumin) for expanding and maintaining hESCs in an undifferentiated state, hESCs were cultured in suspension, as follows.

Materials and Experimental Methods

ESCs and culture media—ESC cultures and the tested media: D1 medium, D2 medium, HA16 medium, HA19 medium and HACM100 medium, which do not contain serum or serum replacement; and the CM100F medium which contains serum replacement, were as described in Example 2, hereinabove.

Culture in suspension—To examine the possibility of using the TGFβ-containing medium which is devoid of serum, serum replacement and albumin for scalable culture of hESCs in suspension, hESCs were cultured in suspension in 58 mm petri dishes (Greiner, Frickenhausen, Germany) in a cell density of $1.5 \times 10^6$ to $6 \times 10^6$. The HA16 medium was supplemented with 0.1% F68 (Sigma, St. Louis, MO, USA) for the suspended culture. The cells were passage every 5-7 days using either 30-60 minute incubation with 1.5 mg/ml type IV Collagenase (Worthington biochemical corporation, Lakewood, NJ, USA) or 25 minutes incubation with 1.5 mg/ml type IV Collagenase followed by five minutes incubation with 1 mg/ml Dispase (Invitrogen Corporation products, Grand Island NY, USA), and further broken into small clumps using 200 µl Gilson pipette tips. Alternatively, the cells were passaged mechanically using 27 g needles. The medium was changed on a daily basis. Following continuous culturing under these conditions the cells were tested for hESC characteristics. The basic media used for culturing hESCs in suspension (which can be further supplemented with the additive and growth factors as described hereinabove) were DMEM, ko-DMEM, DMEM/F12, MabADCB or NCTC medium.

Derivation of New hESC Lines in a Suspension Culture with the TGFβ-Containing Medium Devoid of Serum, Serum Replacement and Albumin Blastocyst cultivation—Zygotes were donated by couples undergoing PGD or in vitro fertilization (IVF) at Cornell Medical College, NY, who signed informed consent forms. The couples underwent the traditional IVF procedure after ovarian stimulation with gonadotropins and oocyte retrieval. Zygotes were cultured to the blastocyst stage according to IVF laboratory standard protocol: under oil using specialized C 1/C2 media for insemination, growth and blastocyst development (Cornell).

Derivation of hESC lines in a suspension culture—Following the removal of the zona pellucida using Tyrode's acidic solution (Sigma, St Louis MO, USA), the trophoblast layer is specifically removed either by immunosurgery or mechanically using 27 g needles. The exposed ICM is further cultured in suspension culture with a suitable culture medium (e.g., the CM100F, HA16 or D2) for 4-10 days. Initially, the cells are mechanically split using 27 g needles.

RT PCR analysis—Total RNA was isolated from hESCs grown for 10-15 passages in the suspension culture using Tri-Reagent (Sigma, St. Louis MO, USA), according to the manufacturer's instructions. cDNA was synthesized from 1 µg total RNA using MMLV reverse transcriptase RNase H minus (Promega, Madison WI, USA). PCR reactions included denaturation for 5 minutes at 94° C. followed by repeated cycles of 94° C. for 30 seconds, annealing for 30 seconds at an annealing temperature as specified in Table 1, hereinabove and extension at 72° C. for 30 seconds. PCR primers and reaction conditions used are described in Table 1, hereinbelow. PCR products were size-fractionated using 2% agarose gel electrophoresis. DNA markers were used to confirm the size of the resultant fragments.

EB formation from hESCs cultured in suspension—For the formation of EBs, one to three 58 mm petri dishes (Greiner, Frickenhausen, Germany) containing ESCs in suspension cultures were transferred to new 58 mm petri dishes containing EBs-differentiation medium consisting of 80% DMEM/F12 (Biological Industries, Beit Haemek, Israel), supplemented with 20% FBSd (HyClone, Utah, USA), and 1 mM L-glutamine (Invitrogen Corporation, Grand Island NY, USA). Alternatively, prior to their transfer to the EB-differentiation medium, the ESCs were subject to treatment with 1 mg/ml type IV collagenase and further broken into small clumps using 1000 µl Gilson pipette tips. 10 day-old EBs were harvested for RNA isolation and histological examination.

Immunohistochemistry, karyotype analysis and Teratoma formation—were performed as described in Example 2, hereinabove.

Experimental Results

The CM100F, HA16, DI, D2 and HA19 media are suitable for culturing hESCs in suspension—hESCs were cultured in suspension using the newly developed TGFβ-containing medium types which are devoid of serum, serum replacement and albumin. To date, the highest passage of hESCs grown in suspension in the tested medium types were 3 passages in the D1 medium, 7 passages in the D2 medium, 10 passages in the HA19 medium and 17 passages in the CM100F medium. All hESCs exhibited undifferentiated morphology at these passages and can be further cultured in these media and maintain hESCs features. Histological sections of the hESCs clumps formed in the suspension cultures illustrated homogeneous cell population, of round cells with large nucleus (FIGS. 9a-9g). In addition, when the cells were plated back on MEFs, they created colonies with typical hESCs morphology (FIGS. 9b-9e), and if returned to suspension cultures, they continued proliferation as undifferentiated cells (data not shown). When hESCs were cultured in a suspension culture in the presence of the serum or serum replacement-free, IL6RIL6-containing HACM100 medium, the cells were expanded and maintained in the undifferentiated state for at least 1-2 passages (data not shown).

hESCs cultured in suspension in the presence of the DI, D2, HA19 or CM100F media express markers of undifferentiated hESCs—Cells cultured in suspension in the presence of the D2 medium for 3 passages as small clumps of 200-1500 cells expressed stem cells markers such as Oct 4 (FIG. 8a), TRA-1-60 (FIG. 8b), TRA-1-81 (FIG. 8c) and SSEA4 (data not shown). Similar results were obtained with the CM100F, D1 or D2 medium at passage 5 (p-5) (data not shown). When cultured in suspension culture in the presence of the CM100F or the HA19 medium the cells expressed high levels of typical stem cells markers such as Oct 4 (FIG. 10a), Rex1 (FIG. 10b), Sox2 (FIG. 10c), Nanog (FIG. 10d) and FGF4 (data not shown) as demonstrated by RT-PCR analysis.

ESCs cultured in suspension are capable of forming EBs—When removed from the D1, D2 or HA16 medium and transferred to EBs medium (80% DMEM/F12 supplemented with 20% FBSd and 1 mM L-glutamine), the cells formed EBs containing representative tissues of three embryonic germ layers.

Rhesus ESCs can be also cultured in the suspension cultures of the present invention—Similar results with Rhesus ESCs (monkey embryonic stem cells, line R366.4, University of Wisconsin, primate center, Thomson lab, Madison, Wisconsin), which are regarded as good candidate for transgenic model to human diseases, were obtained when the Rhesus ESCs were cultured in suspension in the HA16, D1 and D2 TGFβ-containing culture media (data not shown).

Thus the new TGFβ-containing medium, which is devoid of serum, serum replacement and albumin, or the IL6RIL6-containing medium are capable of supporting the undifferentiated culture of hESCs, while maintaining hESCs characteristics, and provide methods for massive culture of these cells for industrial and clinical purposes.

Analysis and Discussion hESCs, like mouse ES cells, are traditionally cultured with MEFs, which may expose them to animal pathogens. In this study, the present inventors have demonstrated, for the first time, a defined animal, serum and feeder layer-free culture system for hESCs, based on the use of commercial medium supplemented with either $TGFβ_3$ or $TGFβ_1$ and bFGF, and human fibronectin matrix as substitute. This medium is designed for massive cultivation of cells in GMP for industrial or clinical purposes.

All medium types of the present invention (with $TGFβ_3$ or $TGFβ_1$), support hESCs culture. The culture medium with the TGFβ isoform 3 was superior of the culture medium with the $TGFβ_1$ isoform in terms of less background differentiation. All medium types of the present invention support the culture with feeders as good as with the regular serum containing media. Cells retained the same proliferation rates and the same background differentiation percentages as hESCs cultured with MEFs using traditional culture methods. Furthermore, the medium can also be used for massive suspended culture of undifferentiated hESCs.

Two isoforms of TGFβ, $TGFβ_3$ and $TGFβ_1$, were tested for their ability to maintain hESCs in an undifferentiated state using various culture conditions. $TGFβ_3$ (D2 and HA16 media) was found to be the most suitable medium supplement, supporting undifferentiated culture of hESCs while using all the tested culture possibilities. All hESCs, from three different cell lines, continued to proliferate while retaining normal hESC features throughout the prolonged culture. Medium supplemented with $TGFβ_1$ (D1 medium) on the contrary, was demonstrated to support undifferentiated hESC culture only while using feeder layer free culture systems.

Cells cultured while using these media (D1, D2, and HA16) maintained all the characteristics of ESCs. After prolonged culture of more than 20 passages, the cells remained undifferentiated, as demonstrated by the colony and single cell morphology, and by the expression of markers typical of undifferentiated primate ESCs [Thomson et al, 1995, 1996, 1998; Reubinoff et al, 2000]. In addition, while cultured in these conditions, hESCs expressed specific markers for the undifferentiated stage such as Oct 4, Sox 2, Rex1 and Nanog, as demonstrated by RT-PCR.

Karyotype analysis carried out on representative cell samples demonstrated that the hESCs' karyotype remained stable in the proposed conditions. None of the examined cells exhibited any karyotype abnormalities.

The cells' pluripotency was examined in vitro. Cells cultured in the tested culture systems for more than 10 passages, formed EBs similar to those created when grown on MEFs [Itskovitz-Eldor et al, 2000]. RT-PCR analysis demonstrated that cells within these EBs differentiated into different cell types representative of the three germ layers. Furthermore, following their injection to SCID-Beige mice, hESCs formed teratomas containing a multitude of tissues types (D1 and D2, HA16 in process). The teratoma formation rates were identical to those of cells cultured with MEFs. Thus, the pluripotency of the cells culture continuously in the tested culture methods remained intact.

Additionally, and most importantly, the same measurements were used to characterize cells cultured with the D1, D2 and HA16 medium in suspension. ESCs cultured under these conditions for more than 7 passages exhibited undifferentiated markers and when transferred to differentiation promoting conditions, demonstrated pluripotency. Thus, these media can enable massive culture of undifferentiated hESCs, and facilitate the development of control bioprocesses in industrial bioreactors.

These results demonstrate that hESCs can be maintained as undifferentiated cells in the proposed defined animal- and serum-free medium combination, without any feeder cells (D1, D2 and HA16) or alternatively, with commonly used acceptable feeder layers (D2 and HA16). Thus, these media can facilitate hESCs culture for research, industrial and clinical purposes. Moreover, these novel culture media were found to support suspended culture of undifferentiated hESCs, the first and primary step in developing a massive culture system for their growth and scale-up, a crucial step for any industrial and clinical uses.

The mechanism by which hESCs self-maintain is still unclear. Accumulating data suggest the involvement of TGFβ family members in hESCs renewal [Amit et al, 2004; Ludwig et al, 2006; James et al, 2005; Chen et al, 2006, Valdimarsdottir & Mummery, 2006]. Further complementary research is required to explain the underlying mechanisms of action of TGFβ at the level of signal transduction, and the fact that $TGFβ_3$ is more potent than $TGFβ_1$.

Future clinical uses of hESCs will require a reproducible, well-defined and xeno-free culture system. The culture method described in this study of fibronectin and D1, D2 or HA16 medium and foreskins fibroblast meet these needs. The well-defined media demonstrated in the present study are suitable for culturing hESCs and may be advantageous for undertaking research on the mechanisms of ESC self-maintenance, especially of the possible roles of the TGFβ pathway. Other studies using hESCs, such as the research on differentiation pathways and mechanisms, will benefit from the availability of a well-defined and reproducible culture system.

Thus, the present invention discloses for the first time:
1. A defined, xeno-free, serum, serum replacement or albumin-free system suitable for both culture and derivation of hESCs.
2. Defined medium combinations, highly effective in supporting hESCs culture in variety of culture conditions. Priority of $TGFβ_3$ over $TGFβ_1$. $TGFβ_3$ was never demonstrated to promote self-renewal of stem cells.
3. A culture system that allows hESC culturing in suspension as undifferentiated without a carrier (without substrate adherence).
4. A scalable culture system, suitable for developing control bioprocesses in industrial bioreactors.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Additional References are Cited in Text

1. Amit M, Carpenter M K, Inokuma M S, Chiu C-P, Harris C P, Waknitz M A, Itskovitz-Eldor J, Thomson J A. Clonally derived human embryonic stem cell lines maintain pluripotency and proliferative potential for prolonged periods of culture. Dev Biol 2000; 227:271-278.
2. Bhattacharya B, Miura T, Brandenberg R, Mejido J, Luo Y, Yang A X, Joshi B H, Irene G, Thies R S, Amit M, Lyons I, Condie B G, Iskovitz-Eldor J, Rao M S, Puri R K. "Gene expression in human embryonic stem cell lines: unique molecular signature". Blood 15; 103(8):2956-64, 2004.
3. Daheron L, Opitz S L, Zaehres H, Lensch W M, Andrews P W, Itskovitz-Eldor J, Daley G Q. LIF/STAT3 signaling fails to maintain self-renewal of human embryonic stem cells. Stem Cells. 2004; 22(5):770-8.
4. Humphrey R K, Beattie G M, Lopez A D, Bucay N, King C C, Firpo M T, Rose-John S, Hayek A. Maintenance of pluripotency in human embryonic stem cells is STAT3 independent. Stem Cells. 2004; 22(4):522-30.
5. Sato N, Meijer L, Skaltsounis L, Greengard P, Brivanlou A H. Maintenance of pluripotency in human and mouse embryonic stem cells through activation of Wnt signaling by a pharmacological GSK-3-specific inhibitor. Nat Med. 2004 January; 10(1):55-63.
6. Xu C, Inokuma M S, Denham J, Golds K, Kundu P, Gold J D, Carpenter M K. Feeder-free growth of undifferentiated human embryonic stem cells. Nat Biotechnol 2001; 19:971-974.
7. Richards M, Fong C Y, Chan W K, Wong P C, Bongso A. Human feeders support prolonged undifferentiated growth of human inner cell masses and embryonic stem cells. Nat Biotechnol 2002; 20:933-936.
8. Amit M, Margulets V, Segev H, Shariki C, Laevsky I, Coleman R, and Itskovitz-Eldor J. Human feeder layers for human embryonic stem cells. Biol Reprod 2003; 68:2150-2156.
9. Amit M, Shariki K, Margulets V, and Itskovitz-Eldor J. "Feeder and serum-free culture system for human embryonic stem cells". Biol Reprod 70:837-845, 2004.
10. Hovatta O, Mikkola M, Gertow K, Stromberg A M, Inzunza J, Hreinsson J, Rozell B, Blennow E, Andang M, Ahrlund-Richter L. A culture system using human foreskin fibroblasts as feeder cells allows production of human embryonic stem cells. Hum Reprod. 2003 July; 18(7):1404-9.
11. Williams R, Hilton D, Pease S, Wilson T, Stewart C, Gearing D, Wagner E, Metcal, D, Nicola N, Gough N. Myeloid leukemia inhibitory factor maintains the developmental potential of embryonic stem cells. Nature 1988; 336:684-687.
12. Niwa H, Burdon T, Chambers I, Smith A. Self-renewal of pluripotent embryonic stem cells is mediated via activation of STAT3. Genes Dev. 1998 Jul. 1; 12(13):2048-60.
13. Smith A G, Heath J K, Donaldson D D, Wong G G, Moreau J, Stahl M, Rogers D. Inhibition of pluripotential embryonic stem cell differentiation by purified polypeptides. Nature. 1988 336(6200):688-90.
14. Rose T M, Weiford D M, Gunderson N L, Bruce AG. Oncostatin M (OSM) inhibits the differentiation of pluripotent embryonic stem cells in vitro. Cytokine. 1994 6(1):48-54.
15. Conover J C, Ip N Y, Poueymirou W T, Bates B, Goldfarb M P, DeChiara T M, Yancopoulos G D. Ciliary neurotrophic factor maintains the pluripotentiality of embryonic stem cells. Development. 1993 119(3):559-65.
16. Nichols J, Chambers I, Smith A. Derivation of germline competent embryonic stem cells with a combination of interleukin-6 and soluble interleukin-6 receptor. Exp Cell Res. 1994 215(1):237-9.
17. Thomson J A, Itskovitz-Eldor, J, Shapiro S S, Waknitz M A, Swiergiel J J, Marshall V S, Jones J M. Embryonic stem cell lines derived from human blastocysts. Science 1998; 282:1145-1147 [erratum in Science 1998; 282: 1827].
18. Reubinoff B E, Pera M F, Fong C, Trounson A., Bongso A. Embryonic stem cell lines from human blastocysts: somatic differentiation in vitro. Nat Biotechnol 2000; 18:399-404.
19. Amit M. & Itskovitz-Eldor J. Derivation and spontaneous differentiation of human embryonic stem cells. J Anat. 2002; 200:225-232.
20. Thomson J A, Kalishman J, Golos T G, Durning M, Harris C P, Becker R A, Hearn J P. Isolation of a primate embryonic stem cell line. Proc Natl Acad Sci USA 1995; 92:7844-7848.
21. Thomson J A, Kalishman J, Golos T G, Durning M, Harris C P, Hearn J P. Pluripotent cell lines derived from common marmoset (Callithrix jacchus) blastocysts. Biol Reprod 1996; 55: 254-259.
22. Itskovitz-Eldor J, Schuldiner M, Karsenti D, Eden A, Yanuka O, Amit M, Soreq H, Benvenisty N. Differentiation of human embryonic stem cells into embryoid bodies comprising the three embryonic germ layers. Mol Med 2000; 6:88-95.
23. Xu R H, Peck R M, Li D S, Feng X, Ludwig T, Thomson J A. Basic FGF and suppression of BMP signaling sustain undifferentiated proliferation of human ES cells. Nat Methods. 2005; 2(3):185-190.

24. Xu C, Rosler E, Jiang J, Lebkowski J S, Gold J D, O'Sullivan C, Delavan-Boorsma K, Mok M, Bronstein A, Carpenter M K. Basic fibroblast growth factor supports undifferentiated human embryonic stem cell growth without conditioned medium. Stem Cells. 2005b; 23:315-23.
25. Chebath J, Fischer D, Kumar A, Oh J W, Kolett O, Lapidot T, Fischer M, Rose-John S, Nagler A, Slavin S, Revel M. Interleukin-6 receptor-interleukin-6 fusion proteins with enhanced interleukin-6 type pleiotropic activities. Eur Cytokine Netw. 1997; 8: 359-65.
26. Kollet O., Aviram R, Chebath J, ben-Hur H, Nagler A, Shultz L, Revel M and Lapidot T. The soluble Interleukin-6 (IL-6) Receptor/IL-6 fusion protein enhances in vitro maintenance and proliferation of human CD34+ CD38−/low cells capable of repopulating Severe Combined Immunodeficiency mice. BLOOD 1999; 94: 923-931.
27. Hirano T, Nakajima K, Hibi M. Signaling mechanisms through gp130: a model of the cytokine system. Cytokine Growth Factor Rev. 1997; 8:241-52.
28. James, D., Levine, A. J., Besser, D., Hemmati-Brivanlou, A., Development 2005, 132: 1273-82.

---

SEQUENCE LISTING

```
Sequence total quantity: 32
SEQ ID NO: 1            moltype = DNA  length = 23
FEATURE                 Location/Qualifiers
misc_feature            1..23
                        note = Single strand DNA oligonucleotide
source                  1..23
                        mol_type = other DNA
                        organism = synthetic construct
SEQUENCE: 1
gagaacaatg agaaccttca gga                                             23

SEQ ID NO: 2            moltype = DNA  length = 23
FEATURE                 Location/Qualifiers
misc_feature            1..23
                        note = Single strand DNA oligonucleotide
source                  1..23
                        mol_type = other DNA
                        organism = synthetic construct
SEQUENCE: 2
ttctggcgcc ggttacagaa cca                                             23

SEQ ID NO: 3            moltype = DNA  length = 24
FEATURE                 Location/Qualifiers
misc_feature            1..24
                        note = Single strand DNA oligonucleotide
source                  1..24
                        mol_type = other DNA
                        organism = synthetic construct
SEQUENCE: 3
tgcttgaatg tgctgatgac aggg                                            24

SEQ ID NO: 4            moltype = DNA  length = 24
FEATURE                 Location/Qualifiers
misc_feature            1..24
                        note = Single strand DNA oligonucleotide
source                  1..24
                        mol_type = other DNA
                        organism = synthetic construct
SEQUENCE: 4
aaggcaagtc agcagccatc tcat                                            24

SEQ ID NO: 5            moltype = DNA  length = 25
FEATURE                 Location/Qualifiers
misc_feature            1..25
                        note = Single strand DNA oligonucleotide
source                  1..25
                        mol_type = other DNA
                        organism = synthetic construct
SEQUENCE: 5
gctggattgt ctgcaggatg gggaa                                           25

SEQ ID NO: 6            moltype = DNA  length = 25
FEATURE                 Location/Qualifiers
misc_feature            1..25
                        note = Single strand DNA oligonucleotide
source                  1..25
                        mol_type = other DNA
                        organism = synthetic construct
SEQUENCE: 6
tcccctgaag aaaattggtt aaaat                                           25

SEQ ID NO: 7            moltype = DNA  length = 22
```

```
FEATURE                 Location/Qualifiers
misc_feature            1..22
                        note = Single strand DNA oligonucleotide
source                  1..22
                        mol_type = other DNA
                        organism = synthetic construct
SEQUENCE: 7
gagtgaaatg gcacgatacc ta                                              22

SEQ ID NO: 8            moltype = DNA  length = 22
FEATURE                 Location/Qualifiers
misc_feature            1..22
                        note = Single strand DNA oligonucleotide
source                  1..22
                        mol_type = other DNA
                        organism = synthetic construct
SEQUENCE: 8
tttcctctcc ttcttcacct tc                                              22

SEQ ID NO: 9            moltype = DNA  length = 22
FEATURE                 Location/Qualifiers
misc_feature            1..22
                        note = Single strand DNA oligonucleotide
source                  1..22
                        mol_type = other DNA
                        organism = synthetic construct
SEQUENCE: 9
ggagttatgg tgggtatggg tc                                              22

SEQ ID NO: 10           moltype = DNA  length = 22
FEATURE                 Location/Qualifiers
misc_feature            1..22
                        note = Single strand DNA oligonucleotide
source                  1..22
                        mol_type = other DNA
                        organism = synthetic construct
SEQUENCE: 10
agtggtgaca aaggagtagc ca                                              22

SEQ ID NO: 11           moltype = DNA  length = 32
FEATURE                 Location/Qualifiers
misc_feature            1..32
                        note = Single strand DNA oligonucleotide
source                  1..32
                        mol_type = other DNA
                        organism = synthetic construct
SEQUENCE: 11
atctggcacc acaccttcta caatgagctg cg                                   32

SEQ ID NO: 12           moltype = DNA  length = 32
FEATURE                 Location/Qualifiers
misc_feature            1..32
                        note = Single strand DNA oligonucleotide
source                  1..32
                        mol_type = other DNA
                        organism = synthetic construct
SEQUENCE: 12
cgtcatactc ctgcttgctg atccacatct gc                                   32

SEQ ID NO: 13           moltype = DNA  length = 18
FEATURE                 Location/Qualifiers
misc_feature            1..18
                        note = Single strand DNA oligonucleotide
source                  1..18
                        mol_type = other DNA
                        organism = synthetic construct
SEQUENCE: 13
cccccggcgg caatagca                                                   18

SEQ ID NO: 14           moltype = DNA  length = 20
FEATURE                 Location/Qualifiers
misc_feature            1..20
                        note = Single strand DNA oligonucleotide
source                  1..20
                        mol_type = other DNA
                        organism = synthetic construct
SEQUENCE: 14
tcggcgccgg ggagatacat                                                 20
```

```
SEQ ID NO: 15               moltype = DNA  length = 23
FEATURE                     Location/Qualifiers
misc_feature                1..23
                            note = Single strand DNA oligonucleotide
source                      1..23
                            mol_type = other DNA
                            organism = synthetic construct
SEQUENCE: 15
gcgtacgcaa attaaagtcc aga                                              23

SEQ ID NO: 16               moltype = DNA  length = 25
FEATURE                     Location/Qualifiers
misc_feature                1..25
                            note = Single strand DNA oligonucleotide
source                      1..25
                            mol_type = other DNA
                            organism = synthetic construct
SEQUENCE: 16
cagcatccta acagctcgc agaat                                             25

SEQ ID NO: 17               moltype = DNA  length = 23
FEATURE                     Location/Qualifiers
misc_feature                1..23
                            note = Single strand DNA oligonucleotide
source                      1..23
                            mol_type = other DNA
                            organism = synthetic construct
SEQUENCE: 17
taccatgcga ccagtggtgc gct                                              23

SEQ ID NO: 18               moltype = DNA  length = 23
FEATURE                     Location/Qualifiers
misc_feature                1..23
                            note = Single strand DNA oligonucleotide
source                      1..23
                            mol_type = other DNA
                            organism = synthetic construct
SEQUENCE: 18
gaattctggt tatcatcggg gaa                                              23

SEQ ID NO: 19               moltype = DNA  length = 23
FEATURE                     Location/Qualifiers
misc_feature                1..23
                            note = Single strand DNA oligonucleotide
source                      1..23
                            mol_type = other DNA
                            organism = synthetic construct
SEQUENCE: 19
ctacaacgcc tacgagtcct aca                                              23

SEQ ID NO: 20               moltype = DNA  length = 24
FEATURE                     Location/Qualifiers
misc_feature                1..24
                            note = Single strand DNA oligonucleotide
source                      1..24
                            mol_type = other DNA
                            organism = synthetic construct
SEQUENCE: 20
gttgcaccag aaaagtcaga gttg                                             24

SEQ ID NO: 21               moltype = DNA  length = 25
FEATURE                     Location/Qualifiers
misc_feature                1..25
                            note = Single strand DNA oligonucleotide
source                      1..25
                            mol_type = other DNA
                            organism = synthetic construct
SEQUENCE: 21
ctcagtgatc ctgatcagat gaacg                                            25

SEQ ID NO: 22               moltype = DNA  length = 25
FEATURE                     Location/Qualifiers
misc_feature                1..25
                            note = Single strand DNA oligonucleotide
source                      1..25
                            mol_type = other DNA
                            organism = synthetic construct
SEQUENCE: 22
agtccctggc ggcaagatta tcaag                                            25
```

```
SEQ ID NO: 23              moltype = DNA  length = 25
FEATURE                    Location/Qualifiers
misc_feature               1..25
                           note = Single strand DNA oligonucleotide
source                     1..25
                           mol_type = other DNA
                           organism = synthetic construct
SEQUENCE: 23
acctgactcc tgaggagaag tctgc                                            25

SEQ ID NO: 24              moltype = DNA  length = 25
FEATURE                    Location/Qualifiers
misc_feature               1..25
                           note = Single strand DNA oligonucleotide
source                     1..25
                           mol_type = other DNA
                           organism = synthetic construct
SEQUENCE: 24
tagccacacc agccaccact ttctg                                            25

SEQ ID NO: 25              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 25
atgcacggca tctgggaatc                                                  20

SEQ ID NO: 26              moltype = DNA  length = 24
FEATURE                    Location/Qualifiers
misc_feature               1..24
                           note = Single strand DNA oligonucleotide
source                     1..24
                           mol_type = other DNA
                           organism = synthetic construct
SEQUENCE: 26
gctactgtcc tgcaagttgc tgtc                                             24

SEQ ID NO: 27              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 27
cagtctgacc agcgtgaaaa                                                  20

SEQ ID NO: 28              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 28
ggccatccaa atctgtccta                                                  20

SEQ ID NO: 29              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 29
actaacatga gtgtggatcc                                                  20

SEQ ID NO: 30              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 30
```

```
                                              -continued
tcatcttcac acgtcttcag                                                   20

SEQ ID NO: 31           moltype = AA  length = 543
FEATURE                 Location/Qualifiers
REGION                  1..543
                        note = IL6R/IL6 chimeric protein
source                  1..543
                        mol_type = protein
                        organism = synthetic construct
SEQUENCE: 31
MLAVGCALLA ALLAAPGAAL APRRCPAQEV ARGVLTSLPG DSVTLTCPGV EPEDNATVHW   60
VLRKPAAGSH PSRWAGMGRR LLLRSVQLHD SGNYSCYRAG RPAGTVHLLV DVPPEEPQLS  120
CFRKSPLSNV VCEWGPRSTP SLTTKAVLLV RKFQNSPAED FQEPCQYSQE SQKFSCQLAV  180
PEGDSSFYIV SMCVASSVGS KFSKTQTFQG CGILQPDPPA NITVTAVARN PRWLSVTWQD  240
PHSWNSSFYR LRFELRYRAE RSKTFTTWMV KDLQHHCVIH DAWSGLRHVV QLRAQEEFGQ  300
GEWSEWSPEA MGTPWTESRS PPAENEVSTP MQALTTNKDD DNILFRDSAN ATSLPVEFMP  360
VPPGEDSKDV AAPHRQPLTS SERIDKQIRY ILDGISALRK ETCNKSNMCE SSKEALAENN  420
LNLPKMAEKD GCFQSGFNEE TCLVKIITGL LEFEVYLEYL QNRFESSEEQ ARAVQMSTKV  480
LIQFLQKKAK NLDAITTPDP TTNASLLTKL QAQNQWLQDM TTHLILRSFK EFLQSSLRAL  540
RQM                                                                543

SEQ ID NO: 32           moltype = AA  length = 365
FEATURE                 Location/Qualifiers
source                  1..365
                        mol_type = protein
                        organism = Homo sapiens
SEQUENCE: 32
MLAVGCALLA ALLAAPGAAL APRRCPAQEV ARGVLTSLPG DSVTLTCPGV EPEDNATVHW   60
VLRKPAAGSH PSRWAGMGRR LLLRSVQLHD SGNYSCYRAG RPAGTVHLLV DVPPEEPQLS  120
CFRKSPLSNV VCEWGPRSTP SLTTKAVLLV RKFQNSPAED FQEPCQYSQE SQKFSCQLAV  180
PEGDSSFYIV SMCVASSVGS KFSKTQTFQG CGILQPDPPA NITVTAVARN PRWLSVTWQD  240
PHSWNSSFYR LRFELRYRAE RSKTFTTWMV KDLQHHCVIH DAWSGLRHVV QLRAQEEFGQ  300
GEWSEWSPEA MGTPWTESRS PPAENEVSTP MQALTTNKDD DNILFRDSAN ATSLPGSRRR  360
GSCGL                                                              365
```

What is claimed is:

1. A method of generating lineage-specific cells from primate embryonic stem cells, the method comprising:
   (a) culturing the primate embryonic stem cells in a protein carrier-free culture medium comprising basic fibroblast growth factor (bFGF) and at least one factor selected from the group consisting of: transforming growth factor beta-3 (TGFβ3) isoform, transforming growth factor beta-1 (TGFβ1) isoform and IL6RIL6 chimera, wherein said IL6RIL6 chimera comprises amino acids 112-355 of SEQ ID NO: 32, to thereby obtain expanded, undifferentiated embryonic stem cells;
   (b) subjecting said expanded, undifferentiated primate embryonic stem cells to culturing conditions suitable for differentiating and/or expanding lineage specific cells;
   thereby generating the lineage-specific cells from the primate embryonic stem cells.

2. A method of generating embryoid bodies from primate embryonic stem cells, the method comprising:
   (a) culturing the primate embryonic stem cells in a protein carrier-free culture medium comprising basic fibroblast growth factor (bFGF) and at least one factor selected from the group consisting of: transforming growth factor beta-3 (TGFβ3) isoform, transforming growth factor beta-1 (TGFβ1) isoform and IL6RIL6 chimera, wherein said IL6RIL6 chimera comprises amino acids 112-355 of SEQ ID NO: 32, to thereby obtain expanded, undifferentiated embryonic stem cells; and
   (b) subjecting said expanded, undifferentiated embryonic stem cells to culturing conditions suitable for differentiating said primate embryonic stem cells to embryoid bodies;
   thereby generating the embryoid bodies from the primate embryonic stem cells.

3. A method of generating lineage-specific cells from primate embryonic stem cells, the method comprising:
   culturing the primate embryonic stem cells in a protein carrier-free culture medium comprising basic fibroblast growth factor (bFGF) and at least one factor selected from the group consisting of: transforming growth factor beta-3 (TGFβ3) isoform, transforming growth factor beta-1 (TGFβ1) isoform and IL6RIL6 chimera, wherein said IL6RIL6 chimera comprises amino acids 112-355 of SEQ ID NO: 32, to thereby obtain expanded, undifferentiated primate embryonic stem cells;
   (b) subjecting said expanded, undifferentiated primate embryonic stem cells to culturing conditions suitable for differentiating said expanded, undifferentiated embryonic stem cells to embryoid bodies; and
   (c) subjecting cells of said embryoid bodies to culturing conditions suitable for differentiating and/or expanding lineage specific cells;
   thereby generating the lineage-specific cells from the primate embryonic stem cells.

4. The method of claim 1, wherein said culture medium is serum-free.

5. The method of claim 1, wherein said culture medium further comprises insulin, transferrin, selenium and a lipid mixture.

6. The method of claim 1, wherein said culturing is effected in xeno-free culturing conditions.

7. The method of claim 1, wherein said culturing is effected in a suspension culture.

8. The method of claim 1, wherein said culturing is effected on a feeder-layer free matrix.

9. The method of claim 1, wherein said culturing is effected on feeder cells.

10. The method of claim 1, wherein said at least one factor is said TGFβ3 isoform, and wherein the culture medium which comprises said TGFβ3 isoform is serum-free, animal contaminant-free, feeder-free and protein carrier-free.

11. The method of claim 1, wherein said at least one factor is said IL6RIL6 chimera and wherein the culture medium which comprises said IL6RIL6 chimera further comprises ascorbic acid.

12. The method of claim 1, wherein said bFGF is at a concentration of at least 2 ng/ml.

13. The method of claim 1, wherein said at least one factor is said TGFβ3 isoform, and wherein said TGFβ3 is at a concentration of at least 0.5 ng/ml.

14. The method of claim 1, wherein said at least one factor is said TGFβ3 isoform, wherein said TGFβ3 is at a concentration of at least 0.5 ng/ml and wherein said bFGF is at a concentration of at least 2 ng/ml.

15. The method of claim 1, wherein said at least one factor is said IL6RIL6 chimera, and wherein said IL6RIL6 chimera is provided at a concentration of at least 25 ng/ml.

16. The method of claim 11, wherein said ascorbic acid is at a concentration of 500 ng/ml±10%.

17. The method of claim 1, wherein said primate embryonic stem cells are human embryonic stem cells.

\* \* \* \* \*